(12) United States Patent
Shepard et al.

(10) Patent No.: US 7,605,144 B2
(45) Date of Patent: *Oct. 20, 2009

(54) ENZYME CATALYZED THERAPEUTIC COMPOUNDS

(75) Inventors: H. Michael Shepard, Encinitas, CA (US); Ming Fai Chan, Encinitas, CA (US); Michael P. Groziak, Palo Alto, CA (US)

(73) Assignee: Celmed Oncology (USA), Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/681,418

(22) Filed: Oct. 7, 2003

(65) Prior Publication Data

US 2004/0077588 A1 Apr. 22, 2004

Related U.S. Application Data

(63) Continuation of application No. 09/856,127, filed as application No. PCT/US00/20008 on Jul. 21, 2000, now Pat. No. 6,683,061.

(60) Provisional application No. 60/191,315, filed on Mar. 21, 2000, provisional application No. 60/145,437, filed on Jul. 23, 1999, provisional application No. 60/145,356, filed on Jul. 22, 1999.

(51) Int. Cl.
*A61K 31/70* (2006.01)
*C07H 19/10* (2006.01)
*C12Q 1/66* (2006.01)
*C12P 29/00* (2006.01)
*C12P 31/00* (2006.01)

(52) U.S. Cl. ............................. 514/51; 536/26.8; 435/8; 435/63; 435/64

(58) Field of Classification Search .................. 514/50, 514/51; 536/26.8, 28.2, 28.54–55; 436/8, 436/63, 64; 435/8, 63, 64
See application file for complete search history.

(56) References Cited

U.S. PATENT DOCUMENTS

| | | | |
|---|---|---|---|
| 3,852,266 A * | 12/1974 | Kiyanagi et al. | ......... 536/28.55 |
| 4,247,544 A | 1/1981 | Bergstrom et al. | |
| 4,267,171 A | 5/1981 | Bergstrom et al. | |
| 4,542,210 A | 9/1985 | Sakata et al. | |
| 4,668,777 A | 5/1987 | Caruthers et al. | |
| 4,816,570 A | 3/1989 | Farquhar | |
| 4,948,882 A | 8/1990 | Ruth | |
| 4,963,263 A | 10/1990 | Kauver | |
| 4,963,533 A | 10/1990 | De Clercq et al. | |
| 4,975,278 A | 12/1990 | Senter et al. | |
| 5,070,082 A * | 12/1991 | Murdock et al. | ............ 514/105 |
| 5,077,282 A * | 12/1991 | Murdock et al. | ............ 514/80 |
| 5,077,283 A * | 12/1991 | Murdock et al. | ............ 514/94 |
| 5,085,983 A | 2/1992 | Scanlon | |
| 5,116,822 A | 5/1992 | De Clercq et al. | |
| 5,116,827 A * | 5/1992 | Murdock et al. | ............... 514/82 |
| 5,133,866 A | 7/1992 | Kauver | |
| 5,137,724 A | 8/1992 | Balzarini et al. | |
| 5,212,161 A * | 5/1993 | Moriniere et al. | ............. 514/50 |
| 5,212,291 A * | 5/1993 | Murdock et al. | ............. 536/6.4 |
| 5,217,869 A | 6/1993 | Kauver | |
| 5,233,031 A | 8/1993 | Borch et al. | |
| 5,264,618 A | 11/1993 | Felgner et al. | |
| 5,300,425 A | 4/1994 | Kauver | |
| 5,338,659 A | 8/1994 | Kauver et al. | |
| 5,430,148 A | 7/1995 | Webber et al. | |
| 5,433,955 A | 7/1995 | Bredehorst et al. | |
| 5,457,187 A * | 10/1995 | Gmeiner et al. | ............. 536/25.5 |
| 5,459,127 A | 10/1995 | Felgner et al. | |
| 5,516,631 A | 5/1996 | Frisch | |
| 5,521,161 A | 5/1996 | Malley et al. | |
| 5,527,900 A | 6/1996 | Balzarini et al. | |
| 5,596,018 A | 1/1997 | Baba et al. | |
| 5,616,564 A * | 4/1997 | Rapaport et al. | ............... 514/44 |
| 5,627,165 A | 5/1997 | Glazier | |
| 5,645,988 A | 7/1997 | Vande Woude et al. | |
| 5,663,321 A | 9/1997 | Gmeiner et al. | |
| 5,733,896 A | 3/1998 | Holý et al. | |
| 5,798,340 A | 8/1998 | Bischofberger et al. | |
| 5,968,910 A | 10/1999 | Balzarini | |
| 5,981,507 A | 11/1999 | Josephson et al. | |
| 6,057,305 A | 5/2000 | Holý et al. | |
| 6,245,750 B1 * | 6/2001 | Shepard | ....................... 514/51 |
| 6,339,151 B1 * | 1/2002 | Shepard et al. | ............. 536/26.8 |
| 6,495,553 B1 * | 12/2002 | Shepard | ....................... 514/256 |
| 6,589,941 B1 | 7/2003 | Fahrig et al. | |
| 6,599,499 B1 | 7/2003 | Rosen et al. | |
| 6,677,314 B2 | 1/2004 | Klecker et al. | |
| 6,677,315 B2 | 1/2004 | Klecker et al. | |
| 6,682,715 B2 | 1/2004 | Klecker et al. | |
| 6,683,045 B2 | 1/2004 | Klecker et al. | |

(Continued)

FOREIGN PATENT DOCUMENTS

DE 32 29 169 A1 2/1984

(Continued)

OTHER PUBLICATIONS

Hakimelahi et al., "Design, Synthesis, and Structure-Activity Relationship of Novel Dinucleotide Analogs as Agents Against Herpes and Human Immunodeficiency Viruses," *Journal of Medicinal Chemistry*, 38(23), 4648-4659 (Nov. 10, 1995).*

(Continued)

*Primary Examiner*—Shaojia Anna Jiang
*Assistant Examiner*—L. E. Crane
(74) *Attorney, Agent, or Firm*—Antoinette F. Konski, Esq.; Foley & Lardner LLP

(57) ABSTRACT

This invention provides novel compounds selected from the group consisting of a 1,5-substituted pyrimidine derivative or analog and substituted furano-pyrimidone analogs. The compounds are useful to treat or prevent diseases such as cancer.

20 Claims, 6 Drawing Sheets

U.S. PATENT DOCUMENTS

| | | | |
|---|---|---|---|
| 6,683,061 B1 * | 1/2004 | Shepard et al. | 514/50 |
| 6,703,374 B1 | 3/2004 | Klecker et al. | |
| 2001/0034440 A1 * | 10/2001 | Shepard et al. | 536/26.8 |
| 2002/0147175 A1 * | 10/2002 | Shepard et al. | 514/49 |
| 2002/0151519 A1 * | 10/2002 | Shepard et al. | 514/50 |

FOREIGN PATENT DOCUMENTS

| | | |
|---|---|---|
| EP | 0 311 107 A2 | 4/1989 |
| EP | 0 311 108 A2 | 4/1989 |
| EP | 0 316 592 | 5/1989 |
| GB | 982776 * | 2/1965 |
| RO | 88451 | 1/1986 |
| WO | WO 89/05817 | 6/1989 |
| WO | WO 90/03978 | 4/1990 |
| WO | WO 91/17424 | 11/1991 |
| WO | WO 92/19767 | 11/1992 |
| WO | WO 93/06120 | 4/1993 |
| WO | WO 94/03467 | 2/1994 |
| WO | WO 94/22483 A2 * | 10/1994 |
| WO | WO 95/01806 | 1/1995 |
| WO | WO 95/08556 A1 * | 3/1995 |
| WO | WO 95/09865 | 4/1995 |
| WO | WO 95/12678 | 5/1995 |
| WO | WO 96/03151 A2 * | 2/1996 |
| WO | WO 96/07431 A1 * | 3/1996 |
| WO | WO 96/07413 | 4/1996 |
| WO | WO 96/10030 | 4/1996 |
| WO | WO 96/10300 A1 * | 4/1996 |
| WO | WO 96/23506 | 8/1996 |
| WO | WO 96/29336 | 9/1996 |
| WO | WO 96/33168 | 10/1996 |
| WO | WO 96/40088 | 12/1996 |
| WO | WO 96/40708 A1 * | 12/1996 |
| WO | WO 96/40739 | 12/1996 |
| WO | WO 97/25342 | 7/1997 |
| WO | WO 97/28179 A1 * | 8/1997 |
| WO | WO 97/49717 | 12/1997 |
| WO | WO 98/49177 | 11/1998 |
| WO | WO 99/06072 | 2/1999 |
| WO | WO 99/08110 A1 * | 2/1999 |
| WO | WO 99/20741 A1 * | 4/1999 |
| WO | WO 99/23104 | 5/1999 |
| WO | WO 99/37753 A1 * | 7/1999 |
| WO | WO 00/18755 | 4/2000 |
| WO | WO 00/33888 | 6/2000 |
| WO | WO 01/07088 | 2/2001 |
| WO | WO 01/07454 A1 * | 2/2001 |
| WO | WO 01/83501 | 11/2001 |
| WO | WO 01/85749 | 11/2001 |

OTHER PUBLICATIONS (RA) Barr et al., "Inhibition of Thymidylate Synthetase by 5-Alkynyl-2'-deoxyuridylates," Journal of Medicinal Chemistry, 24(12), 1385-1388(1981).*

(SA) Bergstrom et al., "Synthesis of (E)-5-(3,3,3-Trifluoro-1-propenyl)-2'-deoxyuridine and Related Analogues: Potent and Unusually Selective Antiviral Activity . . . ," Journal of Medicinal Chemistry, 27(3), 279-284 (1984).*

(TA) Bigge et al., "Palladium-Catalyzed Coupling Reactions of Uracil Nucleosides and Nucleotides," J. American Chemical Society, 102(6), 2033-2038 (Mar. 12, 1980).*

(UA) Cho et al., "(E)-5-(3-Oxopropen-1-yl)-2'-deoxyuridine and (E)-5-(Oxopropen-1-yl)-2i,3'-dideoxyuridine; New Antiviral Agents: Syntheses and Biological Activity," Tetrahedron Letters, 35(8), 1149-1152 (1994).*

(VA) Crisp, G. T., "Synthesis of 5-Alkenyl-2'-deoxyuridines via Organostannanes," Synthetic Communications, 19(11&12), 2117-2123 (1989).*

(WA) Fries et al., "Synthesis and Biological Evaluation of 5-Fluoro-2'-deoxyuridine Phosphoramidate Analogs," Journal of Medicinal Chemistry, 38(14), 2672-2680 (1995).*

(YA) Hobbs, F. W., Jr., "Palladium Catalyzed Synthesis of Alkynylamino Nucleosides. A Universal Linker for Nucleic Acids," Journal of Organic Chemistry, 54(14), 3420-3422 (1989).*

(ZA) Hsiao et al., "Synthesis of 5'-Thymidinyl Bis(1-aziridinyl)phosphonates as Antineoplastic Agents," Journal of Medicinal Chemistry, 24(7), 887-889 (1981).*

(RB) Krajewska et al., "Pyrimidine Ribonucleoside Phosphorylase Activity vs 5-and/or 6-Substituted Uracil and Uridine Analogues, Including Conformational Aspects," Biochemical Pharmacology, 31(6), 1097-1102 (1982).*

(SB) McIntee et al., "Probing the Mechanism of Action and Decomposition of Amino Acid Phosphoramidates of Antiviral Nucleoside Prodrugs," Journal of Medicinal Chemistry, 40(21), 3323-3331 (1997); published in Advance ACS Abstracts, Sep. 15, 1997).*

(TB) Robins et al. (I), "Nucleic Acid Related Compounds. 31. Smooth and Efficient Palladium-Copper Catalyzed Coupling of Terminal Alkynes with 5-Iodouracil Nucleosides," Tetrahedron Letters, 22, 421-424 (1981).*

(UB) Robins et al. (II), "Nucleic Acid Related Compounds. 39. Efficient Conversion of 5-Iodo to 5-Alkynyl and Derived 5-Substituted Uracil Bases and Nucleosides," Journal of Organic Chemistry, 48(11), 1854-1862 (1983).*

(VB) Ruth et al., "C-5 Substituted Pyrimidine Nucleosides. 1. Synthesis of C-5 Allyl, Propyl, and Propenyl Uracil and Cytosine Nucleosides via Organopalladium Intermediates," Journal of Organic Chemistry, 43(14), 2870-2876 (1978).*

(WB) Griengl et al., "Phosphonoformate and Phosphonoacetate Derivatives of 5-Substituted 2Ö-Deoxyuridines: Synthesis and Antiviral Activity," Journal of Medicinal Chemistry, 31(9), 1831-1839 (1988).*

(XB) Gonen et al., "Thymidylate Synthase Expression in Hepatic Tumors Is a Predictor of Survival and Progression in Patients With Resectable Hetastatic Colorectal Cancer," Journal of Clinical Oncology, 21(3), 406-412 (Feb. 1, 2003).*

(YB) Rahman et al., "Elevated Levels of Thymidylate Synthase Linked to Cancer Etiology," Cancer Cell, 5, 341-351 (2004); summarized in CCR/Frontiers in Science, 4, 6-7 (Mar. 2005).*

Firestone et al., "A Comparison of the Effects of Antitumor Agents Upon Normal Human Epidermal Keratinocytes and Human Squamous Cell Carcinoma," *Journal of Investigative Dermatology*, 94(5), 657-661 (May 1990).*

Dagle et al., "Targeted Degradation of mRNA in *Xenopus* oocytes and Embryos Directed by Modified Oligonucleotides: Studies of An2 and Cyclin in Embryogenesis," *Nucleic Acids Research*, 18(16), 4751-4757 (Aug. 25, 1990).*

Hakimelahi et al., "Design, Synthesis, and Structure-Activity Relationship of Novel Dinucleotide Analogs as Agents Against Herpes and Human Immunodeficiency Viruses," *Journal of Medicinal Chemistry*, 38(23), 4648-4659 (Nov. 10, 1995).*

Naesens et al., "Anti-HIV Activity and Metabolism of Phosphoramidate Derivatives of D4T-MP with Variations in the Amino Acid Moiety," Poster Session 1, *The Tenth International Conference on Antiviral Research*, Hotel Nikko, Atlanta, GA, Apr. 6-11, 1997; published in *Antiviral Research*, 34(2), p. A54 (Abstract 40), (Apr. 1997).*

Evrard et al., "An in vitro Nucleoside Analog Screening Method for Cancer Gene Therapy," *Cell Biology and Toxicology*, 12, 345-350 (1996).*

Berkow et al. (eds.), *The Merck Manual of Diagnosis and Therapy, 16th Ed.*, Merck & Co., Rahway, NJ, May, 1992, only p. 1278 supplied.*

Morrison & Boyd (eds.), *Organic Chemistry*, Allyn & Bacon, Inc., Boston, MA, 1973, only pp. 1170-1180 supplied.*

L. B. Townsend (ed.), *Chemistry of Nucleosides and Nucleotides*, vol. 3, Plenum Press, New York, NY, 1974, only Table of Contents, Bibliography pp. 529-535, and Index pp. 537-552 supplied.*

*The American Heritage College Dictionary, Third Edition*, Houghton Mifflin Co., New York, NY, 1997, only p. 668 supplied.*

Barr et al., "Inhibition of Thymidylate Synthetase by 5-Alkynyl-2'-deoxyuridylates," *Journal of Medicinal Chemistry*, 24(12), 1385-1388 (1981).*

Bergstrom et al., "Synthesis of (*E*)-5-(3,3,3-Trifluyoro-1-propenyl)-2'-deoxyuridine and Related Analogues: Potent and Unusually Selective Antiviral Activity of (*E*)-5-(3,3,3-Trifluoro-1-propenyl)-2'-deoxyuridine Against Herpes Simplex Virus Type 1," *Journal of Medicinal Chemistry*, 27(3), 279-284 (1984).*

Bigge et al., "Palladium-Catalyzed Coupling Reactions of Uracil Nucleosides and Nucleotides," *J. American Chemical Society*, 102(6), 2033-2038 (Mar.12, 1980).*

Cho et al., "(*E*)-5-(3-Oxopropen-1-yl)-2'-deoxyuridine and (*E*)-5-(Oxopropen-1-yl)-2',3'-dideoxyuridine; New Antiviral Agents: Syntheses and Biological Activity," *Tetrahedron Letters*, 35(8), 1149-1152 (1994).*

Crisp, G. T., "Synthesis of 5-Alkenyl-2'-deoxyuridines via Organostannanes," *Synthetic Communications*, 19(11&12), 2117-2123 (1989).*

Fries et al., "Synthesis and Biological Evaluation of 5-Fluoro-2'-deoxyuridine Phosphoramidate Analogs," *Journal of Medicinal Chemistry*, 38(14), 2672-2680 (1995).*

Hobbs, F. W., Jr., "Palladium Catalyzed Synthesis of Alkynylamino Nucleosides. A Universal Linker for Nucleic Acids," *Journal of Organic Chemistry*, 54(14), 3420-3422 (1989).*

Hsiao et al., "Synthesis of 5'-Thymidinyl Bis(1-aziridinyl)phosphonates as Antineoplastic Agents," *Journal of Medicinal Chemistry*, 24(7), 887-889 (1981).*

Krajewska et al., "Pyrimidine Ribonucleoside Phosphorylase Activity vs 5-and/or 6-Substituted Uracil and Uridine Analogues, Including Conformational Aspects," *Biochemical Pharmacology*, 31(6), 1097-1102 (1982).*

McIntee et al., "Probing the Mechanism of Action and Decomposition of Amino Acid Phosphoramidates of Antiviral Nucleoside Prodrugs," *Journal of Medicinal Chemistry*, 40(21), 3323-3331 (1997); published in *Advance ACS Abstracts*, Sep. 15, 1997).*

Robins et al. (I), "Nucleic Acid Related Compounds. 31. Smooth and Efficient Palladium-Copper Catalyzed Coupling of Terminal Alkynes with 5-Iodouracil Nucleosides," *Tetrahedron Letters*, 22, 421-424 (1981).*

Robins et al. (II), "Nucleic Acid Related Compounds. 39. Efficient Conversion of 5-Iodo to 5-Alkynyl and Derived 5-Substituted Uracil Bases and Nucleosides," *Journal of Organic Chemistry*, 48(11), 1854-1862 (1983).*

Ruth et al., "C-5 Substituted Pyrimidine Nucleosides. 1. Synthesis of C-5 Allyl, Propyl, and Propenyl Uracil and Cytosine Nucleosides via Organopalladium Intermediates," *Journal of Organic Chemistry*, 43(14), 2870-2876 (1978).*

Griengl et al.,"Phosphonoformate and Phosphonoacetate Derivatives of 5-Substituted 2'-Deoxyuridines: Synthesis and Antiviral Activity," *Journal of Medicinal Chemistry*, 31(9), 1831-1839 (1988).*

Gonen et al., "Thymidylate Synthase Expression in Hepatic Tumors Is a Predictor of Survival and Progression in Patients With Resectable Hetastatic Colorectal Cancer," *Journal of Clinical Oncology*, 21(3), 406-412 (Feb. 1, 2003).*

Rahman et al., "Elevated Levels of Thymidylate Synthase Linked to Cancer Etiology," *Cancer Cell*, 5, 341-351 (2004); summarized in *CCR/Frontiers in Science*, 4, 6-7 (Mar. 2005).*

Abraham et al. "Synthesis and biological activity of aromatic amino acid phosphoramidates of 5-fluoro-2'-deoxyuridine and 1-β-arabinofuranosylcytosine: Evidence of phosphoramidase activity" *J. Med. Chem.* (1996) 39:4569-4575.

Akdas et al. "Glutathione S-transferase and multidrug-resistant phenotype in transitional cell carcinoma of the bladder" *Eur. Urol.* (1996) 29(4):483-486.

Almasan et al. "Deficiency of retinoblastoma protein leads to inappropriate S-phase entry, activation of E2F-responsive genes, and apoptosis" PNAS, USA (Jun. 1995) 92:5436-5440.

Almasan et al. "Genetic instability as a consequence of inappropriate entry into and progression through S-phase" *Cancer Metast. Rev.* (1995) 14:59-73.

Anglada et al. "N,N-cyclization of carbodiimides with 2-(bromomethyl)acrylic acid. A direct entry to the system 5-methylene-6*H*-pyrimidine-2,4-dione, A new class of thymine analogues" *J. Heterocyclic Chem.* (Jul.-Aug. 1996) 33:1259-1270.

Antelman et al. "Inhibition of tumor cell proliferation in vitro and in vivo by exogenous p110 $^{RB}$, the retinoblastoma tumor suppressor protein" *Oncogene* (1995) 10:697-704.

Asakura and Robins, "Cerium(IV) catalyzed iodination at C5 of uracil nucleosides" *Tetrahedron Lett.* (1988) 29(23):2855-2858.

Asakura et al. "Cerium(IV)-mediated halogenation at C-5 of uracil derivatives" *J. Org. Chem.* (1990) 55:4928-4933.

Aschele et al. "Immunohistochemical quantitation of thymidylate synthase expression in colorectal cancer metastases predicts for clinical outcome to fluorouracil-based chemotherapy" *J. Clin. Oncol.* (Jun. 1999) 17(6):1760-1770.

Bagshawe, K.D. "Antibody-directed enzyme prodrug therapy: A review", *Drug Develop. Res.* (1995) 34(2):220-230.

Bajetta et al. "A pilot safety study of capecitabine, a new oral fluoropyrimidine, in patients with advanced neoplastic disease" *Tumori* (1996) 82:450-452.

Balzarini et al. "Incorporation of 5-substituted pyrimidine nucleoside analogues into DNA of a thymidylate synthetase-deficient murine FM3A carcinoma cell line" *Meth. Find. Exp. Clin. Pharmacol.* (1985) 7(1):19-28.

Balzarini et al. "The cytostatic activity of 5-(1-azidovinyl)-2'-deoxyuridine (AzVDU) against herpes simplex virus thymidine kinase gene-transfected FM3A cells is due to inhibition of thymidylate synthase and enhanced by UV light (λ = 254 nm) exposure" *FEBS Lett.* (1995) 373:41-44.

Balzarini et al. "Mechanism of anti-HIV action of masked alaninyl d4T-MP derivatives" *PNAS USA* (Jul. 1996) 93:7295-7299.

Banerjee et al. "Molecular mechanisms of resistance to antifolates, a review" *Acta Biochim. Pol.* (1995) 42(4):457-464.

Banerjee et al. "Role of E2F-1 in chemosensitivity" *Cancer Res.* (Oct. 1, 1998) 58:4292-4296.

Barbato et al. "Synthesis of bridged pyrimidine nucleosides and triazo [4, 3-c] pyrimidine nucleoside analogues" *Nucleos. Nucleot.* (1989) 8(4):515-528.

Barbour et al. "A naturally occurring tyrosine to histidine replacement at residue 33 of human thymidylate synthase confers resistance to 5-fluoro-2'-deoxyuridine in mammalian and bacterial cells" *Mol. Pharmacol.* (1992) 42:242-248.

Barr et al. "Reaction of 5-ethynyl-2'-deoxyuridylate with thiols and thymidylate synthetase" *Biochemestry* (1983) 22:1696-1703.

Barrett "Trapping of the C5 methylene intermediate in thymidylate synthase" *J. Am. Chem. Soc.* (1998) 120:449-450.

Benzaria et al. "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" *J. Med. Chem.* (1996) 39:4958-4965.

Bertino et al. "Resistance mechanisms to methotrexate in tumors" *Stem Cells* (1996) 14:5-9.

Budavari (Jul. 1996) (Ed.), *The Merck Index, 12$^{th}$ Edition*, Doxifluridine, p. 3493.

Budavari (Jul. 1996) (Ed.), *The Merck Index,12$^{th}$ Edition*, Floxuridine, p. 4148.

Budavari (Jul. 1996) (Ed.), *The Merck Index, 12$^{th}$ Edition*, Idoxuridine, p. 4934.

Callahan et al. "Rhenium-188 for therapeutic applications from an alumina-based tungsten-188/rhenium-188 radionuclide generator" *Nuc-Compact* (Jan. 1989) 20:3-6.

Carreras and Santi "The catalytic mechanism and structure of thymidylate synthase" *Annu. Rev. Biochem.* (1995) 64:721-762.

Carter et al. "Humanization of an anti-p185$^{HER2}$ antibody for human cancer therapy" *PNAS USA* (May 1992) 89:4285-4289.

Cass et al. "Recent advances in the molecular biology of nucleoside transporters of mammalian cells" *Biochem. Cell Biol.* (1998) 76(5):761-770.

Catucci et al. "Development and significance of the HIV-1 reverse transcriptase M184V mutation during combination therapy with lamivudine, zidovudine, and protease inhibitors" *J. Acquir. Immune Defic. Syndr.* (Jul. 1999) 21(3):203-208.

Chaudhuri and Kool "Very high affinity DNA recognition by bicyclic and cross-linked oligonucleotides" *J. Am. Chem. Soc.* (1995) 117:10434-10442.

Chen et al. "Sensitization of human breast cancer cells to cyclophosphamide and ifosfamide by transfer of a liver cytochrome P450 gene" *Cancer Res.* (Mar. 15, 1996) 56:1331-1340.

Clarke "Animal models of breast cancer: Their diversity and role in biomedical research" *Breast Cancer Res. Tr.* (1996) 39:1-6.

Cobleigh et al. "Multinational study of the efficacy and safety of humanized anti-HER2 monoclonal antibody in women who have HER2-overexpressing metastatic breast cancer that has progressed after chemotherapy for metastatic disease" *J. Clin. Oncol.* (Sep. 1999) 17(9):2639-2648.

Coderre et al. "Mechanism of action of 2',5-difluoro-1-arabinosyluracil" *J. Med. Chem.* (1983) 26(8):1149-1152.

Connors and Knox "Prodrugs in cancer chemotherapy" *Stem Cells* (1995) 13:501-511.

Copur et al. "Thymidylate synthase gene amplification in human colon cancer cell lines resistant to 5-fluorouracil" *Biochem. Pharmacol.* (1995) 49(10):1419-1426.

Costi et al. "Phthalein derivatives as a new tool for selectivity in thymidylate synthase inhibition" *J. Med. Chem.* (1999) 42(12):2112-2124.

Cruickshank et al. "Oligonucleotide labelling: A concise synthesis of a modified thymidine phoporamidite" *Tetrahedron Lett.* (1988) 29(41):5221-5224.

Dale et al. "The synthesis and enzymatic polymerization of nucleotides containing mercury: Potential tools for nucleic acid sequencing and structural analysis" *PNAS USA* (Aug. 1973) 70(8):2238-2242.

DeClercq et al. "Antiviral Activity of Novel Deoxyuridine Derivatives" *Current Chemotherapy: Proceedings of the International Congress of Chemotherapy* published in *Virology* (Sep. 18, 1978) 1:352-354.

DeClercq et al. "Nucleic acid related compounds. 40. Synthesis and biological activities of 5-alkynyluracil nucleosides" *J. Med. Chem.* (1983) 26:661-666.

DeClercq "Antiviral Activity Spectrum and Target of Action of Different Classes of Nucleoside Analogues" *Nucleos. Nucleot.* (1994) 13(6&7):1271-1295.

Dicker et al. "Methotrexate resistance in an in vivo mouse tumor due to a non-active-site dihydrofolate reductase mutation" *PNAS USA* (Dec. 1993) 90:11797-11801.

Dirvin et al. "The role of human glutathione S-transferase isoenzymes in the formation of glutathione conjugates of the alkylating cytostatic drug thiotepa" *Cancer Res.* (Apr. 15, 1995) 55:1701-1706.

Dorr and von Hoff "PALA" *In: Cancer Chemotherapy Handbook*, 2nd Edition, Appleton & Lange, Norwalk, Connecticut (1994) pp. 768-773.

Dunn et al. "Solution of the conformation and alignment tensors for the binding of trimethoprim and its analogs to dihydrofolate reductase: 3D-quantitative structure-activity relationship study using molecular shape analysis, 3-way partial least-squares regression, and 3-way factor analysis" *J. Med. Chem.* (1996) 39:4825-4832.

Dyer et al. *"Nucleic Acids Chemistry: Improved and new synthetic procedures, methods, and techniques"* Townsend, L. B. & Tipson, R. S., eds. (Wiley-Interscience, New York, NY) (1991) 4:79-83.

Edler et al. "Immunohistochemically detected thymidylate synthase in colorectal cancer: An independent prognostic factor of survival" *Clinical Cancer Research* (Feb. 2000) 6:488-492.

Fan and Bertino "Functional roles of E2F in cell cycle regulation" *Oncogene* (1997) 14:1191-1200.

Farquhar et al. "Synthesis and antitumor evaluation of bis[(pivaloyloxy)methyl] 2'-deoxy-5-fluorouridine 5'-monophosphate (FdUMP): A strategy to introduce nucleotides into cells" *J. Med. Chem.* (1994) 37:3902-3909.

Farquhar et al. "5'-[4-pivaloyloxy)-1,3,2-dioxaphosphorinan-2-yl]-2'-deoxy-5-fluorouridine: A membrane-permeating prodrug of 5-fluoro-2'-deoxyuridylic acid (FdUMP)" *J. Med. Chem.* (1995) 38:488-495.

Farrow et al. "Synthesis and biological properties of novel phosphotriesters: A new approach to the introduction of biologically active nucleotides into cells" *J. Med. Chem.* (1990) 33(5):1400-1406.

Felmingham and Washington "Trends in the antimicrobial susceptibility of bacterial respiratory tract pathogens—findings of the Alexander Project 1992-1996" *J. Chemotherapy* (1999) 11(Suppl 1):5-21.

Freed et al. "Evidence for acyloxymethyl esters of pyrimidine 5'-deoxyribonucleotides as extracellular sources of active 5'-deoxyribonucleotides in cultured cells" *Biochem. Pharmacol.* (1989) 38(19):3193-3198.

Freemantle et al. "Molecular characterisation of two cell lines selected for resistance to the folate-based thymidylate synthase inhibitor, ZD1694" *Briti. J. Cancer* (1995) 71:925-930.

Funk "Cancer cell cycle control" *Anticancer Research* (1999) 19:4772-4780.

Goldstein and Brown "Genetic aspects of disease" *In: Harrison's Principles of Internal Medicine*, 12th Edition, McGraw-Hill, Inc., New York, NY (1991) pp. 21-76.

Goodwin et al. "Incorporation of alkylthiol chains at C-5 of deoxyuridine" *Tetrahedron Lett.* (1993) 34(35):5549-5552.

Gottesmann et al. "Genetic analysis of the multidrug transporter" *Annu. Rev. Genet.* (1995) 29:607-649.

Graham et al. "DNA duplexes stabilized by modified monomer residues: Synthesis and stability" *J. Chem. Soc. Perkin Trans.* (1998) 1:1131-1138.

Hooker et al. "An in vivo mutation from leucine to tryptophan at position 210 in human immunodeficiency virus type 1 reverse transcriptase contributes to high-level resistance to 3'-azido-3'-deoxythymidine" *J. Virol.* (Nov. 1996) 70(11):8010-8018.

Hostetler et al. "Enhanced oral absorption and antiviral activity of 1-O-octadecyl-sn-glycero-3-phospho-acyclovir and related compounds in hepatitis B virus infection, in vitro" *Biochem. Pharmacol.* (1997) 53:1815-1822.

Houze, et al. "Detection of thymidylate synthase gene expression levels in formalin-fixed paraffin embedded tissue by semiquantitative, nonradioactive reverse transcriptase polymerase chain reaction" *Tumor Biol.* (1997) 18:53-68.

Hudziak et al. "Amplified expression of the HER2/ERBB2 oncogene induces resistance to tumor necrosis factor α in NIH 3T3 cells" *PNAS USA* (Jul. 1988) 85:5102-5106.

Husain et al. "Elevation of topoisomerase I messenger RNA, protein, and catalytic activity in human tumors: Demonstration of tumor-type specificity and implications for cancer chemotherapy" *Cancer. Research* (Jan. 15, 1994) 54:539-546.

Jackman and Calvert "Folate-based thymidylate synthase Inhibitors as anticancer drugs" *Ann. Oncol.* (1995) 6(9):871-881.

Jackman et al. "Quinazoline-based thymidylate synthase inhibitors: Relationship between structural modifications and polyglutamation" *Anti-Cancer Drug Design* (1995) 10:573-589.

Johnston et al. "Thymidylate synthase gene and protein expression correlate and are associated with response to 5-fluorouracil in human colorectal and gastric tumors" *Cancer Res.* (Apr. 1, 1995) 55:1407-1412.

Jones and Mann "New methods of synthesis of β-aminoethylpyrazoles" *J. Am. Cancer Soc.* (Aug. 20, 1953) 75:4048-4052.

Kashani-Sabet et al. "Detection of drug resistance in human tumors by in vitro enzymatic amplification" *Cancer Res.* (Oct. 15, 1988) 48:5775-5778.

Kobayashi et al. "Effect of hammerhead ribozyme against human thymidylate synthase on the cytotoxicity of thymidylate synthase inhibitors" *Jpn. J. Cancer Res.* (Nov. 1995) 86:1014-1018.

Komaki et al. "Difference in thymidylate synthetase activity in involved nodes compared with primary tumor in breast cancer patients" *Breast Cancer Res. Tr.* (1995) 35(2):157-162.

Kwong et al. "Hepatitis C virus NS3/4A protease" *Antivir. Res.* (1999) 41:67-84.

Lasic "Doxorubicin in sterically stabilized liposomes" *Nature* (Apr. 11, 1996) 380:561-562.

Lee et al. "Inhibition of mouse thymidylate synthase promoter activity by the wild-type p53 tumor suppressor protein" *Exp. Cell Res.* (1997) 234:270-276.

Lenz et al. "p53 and thymidylate synthase expression in untreated stage II colon cancer: associations with recurrence, survival, and site" *Clinical Cancer Research* (May 1998) 4:1227-1234.

Leś et al. "Modeling of reaction steps relevant to deoxyuridylate (dUMP) enzymatic methylation and thymidylate synthase mechanism-based inhibition" *Journal of Biomolecular Structure & Dynamics* (1998) 15(4):703-715.

Lewis et al. "Differential responses of human tumor cell lines to anti-p185$^{HER2}$ monoclonal antibodies" *Cancer Immuno. Immunother.* (1993) 37(4):255-263.

Lewis et al. "A serum-resistant cytofection for cellular delivery of antisense oligodeoxynucleotides and plasmid DNA" *PNAS USA.* (Apr. 1996) 93:3176-3181.

Lin et al., "Rhenium188 hydroxyethylidene diphosphonate: a new generator-produced radiotherapeutic drug of potential value for the treatment of bone metastases" *Eur. J. Nucl. Med.* 24(6):590-595 (Jun. 1997).

Livak et al. "Detection of single base differences using biotinylated nucleotides with very long linker arms" *Nucl. Acids Res.* (1992) 20(18):4831-4837.

Livingston et al. "Studies with tetrahydrohomofolate and thymidylate synthetase from amethopterin-resistant mouse leukemia cells" *Biochemistry* (Aug. 1968) 7(8):2814-2818.

Lönn et al. "Higher frequency of gene amplification in breast cancer patients who received adjuvant chemotherapy" *Cancer* (Jan. 1, 1996) 77(1):107-112.

Look et al. "Increased thymidine kinase and thymidylate synthase activities in human epithelial ovarian carcinoma" *Anticancer Res.* (1997) 17:2353-2356.

Lovejoy et al. "Animal models and the molecular pathology of cancer" *J. Pathol.* (1997) 181:130-135.

Madec et al. "Some characteristics of fetal and adult isoenzymes of thymidine kinase in human breast cancers" *Bull. Cancer* (1998) 75:187-194.

Mader et al. "Resistance to 5-fluorouracil" *Gen. Pharma.* (1998) 31(5):661-666.

Mahalingam et al. "Structural and kinetic analysis of drug resistant mutants of HIV-1 protease" *Eur. J. Biochem.* (1999) 263:238-245.

McGuigan et al. "Certain phosphoramidate derivatives of dideoxy uridine (ddU) are active against HIV and successfully by-pass thymidine kinase" *Febs Let* (1994) 351:11-14.

Mead et al. "Pharmacologic aspects of homofolate derivatives in relation to amethopterin-resistant murine leukemia" *Cancer Res.* (Nov. 1966) 26(1):2374-2379.

Meier et al. "ADA-bypass by lipophilic *cyclosal*-ddAMP pronucleotides a second example of the efficiency of the cyclosal-concept" *Bioorg. Med. Chem. Lett.* (1997) 7(12):1577-1582.

Meier et al. "Cyclic saligenyl phosphotriesters of 2',3'-dideoxy-2',3'-didehydrothymidine (d4T)—a new pro-nucleotide approach" *Bioorg. Med. Chem. Lett.* (1997) 7(2):99-104.

Meier et al. "CycloSal-pro-nucleotides: The design and biological evaluation of a new class of lipophilic nucleotide prodrugs" *Int'l. Antiviral News* (1997) 5(10):183-185.

Melton et al. "Antibody-directed enzyme prodrug therapy (ADEPT). Review article" *Drugs of the Future* (1996) 21(2):167-181.

Melton and Sherwood "Antibody-enzyme conjugates for cancer therapy" *J. Natl. Cancer Inst.* (Feb. 21, 1996) 88(3/4):153-165.

Mobashery and Johnston "Reactions of *Escherichia coli* TEM β-lactamase with cephalothin and with Co$_{10}$-dipeptidyl cephalosporin esters" *J. Biol. Chem.* (Jun. 15, 1986) 261(17):7879-7887.

Mobashery et al. "Conscripting β-lactamase for use in drug delivery. Synthesis and biological activity of a cephalosporin C$_{10}$-ester of an antibiotic dipeptide" *J. Am. Chem. Soc.* (1986) 108:1685-1686.

Morgan et al. "Tumor efficacy and bone marrow-sparing properties of TER286, a cytotoxin activated by glutathione S-transferase" *Cancer Res.* (Jun. 15, 1998) 58:2568-2575.

Mulder et al. "Thymidylate synthase levels in tumor biopsies from patients with colorectal cancer" *Anticancer Res.* (1994) 14(6B):2677-2680.

Murray "Antibiotic resistance" *Adv. Internal. Med.* (1997) 42:339-367.

Nagata et al. "The role of HBV DNA quantitative PCR in monitoring the response to Interferon treatment in chronic hepatitis B virus infection" *J. Hepatol.* (1999) 30:965-969.

Negishi et al. "Enhancement of N$^4$-aminocytidine-induced mutagenesis by Ni$^{++}$ion" *Nucl. Acids Symposium* (1996) 35:137-138.

Nichol and Hakala "Comparative growth-inhibitory activity of homofolic aid against cell lines sensitive and resistant to amethopterin" *Biochem. Pharmacol.* (Oct. 1966) 15(10):1621-1623.

Niculescu-Duvaz and Springer "Gene-directed enzyme prodrug therapy: A review of enzyme/prodrug combinations" *Expert Opin. Invest. Drugs* (1997) 6(6):685-703.

Palmer et al. "Highly drug-resistant HIV-1 clinical isolates are cross-resistant to many antiretroviral compounds in current clinical development" *AIDS* (1999) 13(6):661-667.

Paradiso et al. "Thymidilate synthase and p53 primary tumour expression as predictive factors for advanced colorectal cancer patients" *Brit. J. Cancer* (2000) 82(3):560-567.

Patterson et al. "Thymidine phosphorylase moderates thymidine-dependent rescue after exposure to the thymidylate synthase inhibitor ZD1694 (tomudex) in vitro" *Cancer Res.* (Jul. 1, 1998) 58:2737-2740.

Pedersen-Lane et al. "High-level expression of human thymidylate synthase" *Protein Expression and Purification* (1997) 10:256-262.

Pegram et al. "The effect of HER-2/*neu* overexpression on chemotherapeutic drug sensitivity in human breast and ovarian cancer cells" *Oncogene* (1997) 15:537-547.

Pestalozzi et al. "Prognostic importance of thyrnidylate synthase expression in early breast cancer" *J. Clin. Oncol.* (May 1997) 15(5):1923-1931.

Phelps et al. "Synthesis and biological activity of 5-fluoro-2'-deoxyuridine 5'-phosphorodiamidates" *J. Med. Chem.* (1980) 23:1229-1232.

Pluta et al., "Synthesis and biological properties of 4-hydroxy, 4-thio-5-pyrimidine derivatives" *Boll. Chim. Farmaceutico* (Gennaio 1999) 138(1):30-33.

Robins et al. "Nucleic acid related compounds. 38. Smooth and high-yield iodination and chlorination at C-5 of uracil bases and *p*-toluyl-protected nucleosides" *Can. J. Chem.* (1982) 60:554-557.

Rode "Specificity of thymidylate synthase inactivation by 4,5-bisubstituted dUMP analogues" *M. Nencki Inst. Exp. Biol., Acta Biochimica Polonica* (1993) 40(3):363-368.

Romain et al. "Prognostic value of cytosolic thymidine kinase activity as a marker of proliferation in breast cancer" *Int. J. Cancer* (1995) 61:7-12.

Roth et al. "p53 tumor suppressor gene therapy for cancer" *Oncology* (1999) 13(10)(5):148-154.

Saboulard et al. "Characterization of the activation pathway of phosphoramidate triester prodrugs of stavudine and zidouvdine" *Mol. Pharmacol.* (1999) 56:693-704.

Santi "Perspectives on the design and biochemical pharmacology of inhibitors of thymidylate synthetase" *J. Med. Chem.* (Feb. 1980) 23(2):103-111.

Sastry et al. "Membrane-permeable dideoxyuridine 5'-monophosphate analogue inhibits human immunodeficiency virus infection" *Mol. Pharmacol.* (1992) 41:441-445.

Satyam et al. "Design, synthesis, and evaluation of latent alkylating agents activated by glutathione S-transferase" *J. Med. Chem.* (1996) 39:1736-1747.

Shafer and Vuitton "Highly active antiretroviral therapy (HAART) for the treatment of infection with human immunodeficiency virus type 1" *Biomed. & Pharamcother.* (1999) 53:73-86.

Shepard and Lewis "Resistance of tumor cells to tumor necrosis factor" *J. Clin. Immunol.* (1988) 8(5):333-341.

Simon and Schindler "Cell biological mechanisms of multidrug resistance in tumors" *PNAS USA* (Apr. 1994) 91:3497-3504.

Smith et al. "Response to doxorubicin of cultured normal and cancerous human mammary epithelial cells" *JNCI* (Feb. 1985) 74(2):341-347.

Smith et al. "Preliminary correlations of clinical outcome with in vitro chemosensitivity of second passage human breast cancer cells" *Cancer Res.* (May 15, 1990) 50(10):2943-2948.

Smith et al. "Regulation and mechanisms of gene amplification" *Phil. Trans. R. Soc. Lond. B* (1995) 347:49-56.

Stühlinger et al. "Clinical therapy and HER-2 oncogene amplification in breast cancer: Chemo vs radiotherapy" *J. Steroid Biochem. Molec. Biol.* (1994) 49(1):39-42.

Sugarman et al. "Recombinant human tumor necrosis factor-α: Effects on proliferation of normal and transformed cells in vitro" *Science* (Nov. 22, 1985) 230(4728):943-945.

Suki et al. "Risk classification for large cell lymphoma using lactate dehydrogenase, beta-2 microglobulin, and thymidine kinase" *Leukemia and Lymphoma* (1995) 18:87-92.

Tannock "Treatment of cancer with radiation and drugs" *J. Clin. Oncol.* (Dec. 1996) 14(12):3156-3174.

Teh et al. "Tumor suppressor genes (TSG)" *Anticancer Research* (1999) 19:4715-4728.

Tolstikov et al. "Synthesis and DNA duplex stabilities of oligonucleotides containing C-5-(3-methoxypropynyl)-2'-deoxyuridine residues" *Nucleos. Nucleot.* (1997) 16(3):215-225.

Touroutoglou and Pazdar "Thymidylate synthase inhibitors" *Clin. Cancer Res.* (Feb. 1996) 2(2)227-243.

Troutner "Chemical and physical properties of radionuclides" *Nucl. Med. Biol.* (1987) 14(3):171-176.

Turner and Summers "Structural biology of HIV" *J. Mol. Biol.* (1999) 285:1-32.

Valette et al. "Decomposition pathways and in vitro HIV inhibitory effects of isoddA pronucleotides: Toward a rational approach for intracellular delivery of nucleoside 5'-monophosphates" *J. Med. Chem.* (1996) 39:1981-1990.

van Laar "Therapeutic efficacy of fluoropyrimidines depends on the duration of thymidylate synthase inhibition in the murine colon 26-B carcinoma tumor model" *Clin. Cancer Res.* (Aug. 1996) 2(8):1327-1333.

van Triest et al. "Thymidylate synthase level as the main predictive parameter for sensitivity to 5-fluorouracil, but not for folate-based thymidylate synthase inhibitors, in 13 nonselected colon cancer cell lines" *Clin. Cancer Res.* (Mar. 1999) 5(3):643-654.

Wahba and Friedkin "Direct spectrophotometric evidence for the oxidation of tetrahydrofolate during the enzymatic synthesis of thymidylate" *J. Biol. Chem.* (Mar. 1961) 236(3):C11-C12.

Wallis et al. "Synthesis and anti-HIV activity of C4-modified pyrimidine nucleosides" *II Farmaco* (1999) 54:83-89.

Wang "Protease Inhibitors as potential anti-viral agents for the treatment of picornaviral infections" *Prog. Drug Res.* (1999) 52:197-219.

Wataya et al. "trans-5-(3,3,3-trifluoro-1-propenyl)-2'-deoxyuridylate: A mechanism-based inhibitor of thymidylate synthetase" *J. Med. Chem.* (Apr. 1979) 22(4):339-340.

Wataya et al. "Interaction of thymidylate synthetase with 5-nitro-2'-deoxyuridylate" *J. Biol. Chem.* (Jun. 25, 1980) 255(12):5538-5544.

Wettergren et al. "Drug-specific rearrangements of chromosome 12 in hydroxyurea-resistant mouse SEWA cells: Support for chromosomal breakage model of gene amplification" *Somat. Cell Molec. Gen.* (1994) 20(4):267-285.

Whalen and Boyer "Human glutathione S-transferases" *Seminars in Liver Disease* (1998) 18(4):345-358.

Wildner et al. "Enzyme prodrug gene therapy: Synergistic use of the herpes simplex virus-cellular thymidine kinase/ganciclovir system and thymidylate snythase inhibitors for the treatment of colon cancer" *Cancer Res.* (Oct. 15, 1999) 59(20):5233-5238.

Wolfe et al. "Antibody-directed enzyme prodrug therapy with the T268G mutant of human carboxypeptidase A1: in vitro and in vivo studies with prodrugs of methotrexate and the thymidylate synthase inhibitors GW1031 and GW1843" *Bioconjugate Chem.* (1999) 10(1):38-48.

Yen et al. "Characterization of a hydroxyurea-resistant human KB cell line with supersensitivity to 6-thioguanine" *Cancer Res.* (Jul. 15, 1994) 54:3686-3691.

Zeid et al. "Synthesis of new thiolated acyclonucleosides with potential anti-HBV activity" *Nucleos. Nucleot.* (1999) 18(1):95-111.

Andersen et al. "Detection of C-ERBB-2 related protein in sera from breast cancer patients" *Acta Oncol.* (1995) 34(4):499-504.

Ayisi et al. "Comparison of the antiviral effects of 5-methoxymethyldeoxyuridine-5'-monophosphate with adenine arabinoside-5'-monophosphate" *Antivir. Res.* (1983) 3:161-174.

Balzarini et al. "Thymidylate synthase is the principal target enzyme for the cytostatic activity of (E)-5-(2-bromovinyl)-2'-deoxyuridine against murine mammary carcinoma (FM3A) cells transformed with the herpes simplex virus type 1 or type 2 thymidine kinase gene" *Mol. Pharmacol.* (1987) 32:410-416.

Balzarini et al. "Differential mechanism of cytostatic effect of (E)-5-(2-bromovinyl)-2'-deoxyuridine, 9-(1,3-dihydroxy-2-propoxymethyl)guanine, and other antiherpetic drugs on tumor cells transfected by the thymidine kinase gene of herpes simplex virus type 1 or type 2" *J. Biol. Chem.* (1993) 268(9):6332-6337, (Mar. 25, 1993).

Balzarini et al. "Anti-HIV and anti-HBV activity and resistance profile of 2',3'-dideoxy-3'-thiacytidine (3TC) and its arylphosphoramidate derivative CF 1109" *Biochem. Biophy. Res. Co.* (1996) 225:363-369.

Balzarini et al. "Conversion of 2',3'-dideoxyadenosine (ddA) and 2',3'-didehydro-2',3'-dideoxyadenosine (d4A) to their corresponding aryloxyphosphoramidate derivatives markedly potentiates their activity against human immunodeficiency virus and hepatitis B virus" *FEBS Lett.* (1997) 410:324-328.

Barr et al. "Thymidylate synthetase-catalyzed conversions of E-5-(2-bromovinyl)-2'-deoxyuridylate" *J. Biol. Chem.* (1983) 258(22):13627-13631.

Bergstrom et al. "C-5-substituted pyrimidine nucleosides. 3. Reaction of allylic chlorides, alcohols, and acetates with pyrimidine nucleoside derived organopalladium intermediates" *J. Org. Chem.* (1981) 46(7):1432-1441.

Bosslet et al. "A novel one-step tumor-selective prodrug activation system" *Tumor Targeting* (1995) 1:45-50.

Bosslet et al. "Elucidation of the mechanism enabling tumor selective prodrug monotherapy" *Cancer Res.* (Mar. 15, 1998) 58:1195-1201.

Brison "Gene amplification and tumor progression" *Biochim. Biophys. Acta* (1993) 1155:25-41.

Carl et al. "Protease-activated 'prodrugs' for cancer chemotherapy" *PNAS USA* (Apr. 1980) 77(4):2224-2228.

Cava and Levinson "Thionation reactions of Lawesson's reagents" *Tetrahedron* (1985) 41(22):5061-5087.

Chakravarty et al. "Plasmin-activated prodrugs for cancer chemotherapy. 2. Synthesis and biological activity of peptidyl derivatives of doxorubicin" *J. Med. Chem.* (1983) 26(5):638-644.

Colacino "Mechanisms for the anti-hepatitis B virus activity and mitochondrial toxicity of fialuridine (FIAU)" *Antivir. Res.* (1996) 29:125-139.

Collins et al. "Suicide prodrugs activated by Thymidylate synthase: Rationale for treatment and noninvasive imaging of tumors with deoxyuridine analogues" *Clin. Cancer Res.* (Aug. 1999) 5:1976-1981.

Connors "Prodrugs in cancer chemotherapy" *Xenobiotica* (1986) 16(10/11):975-988.

Connors "Is there a future for cancer chemotherapy?" *Ann. Oncol.* (1996) 7:445-452.

Davisson et al. "Expression of human thymidylate synthase in *Escherichia coli*" *J. Biol. Chem.* (1989) 264(16):9145-9148.

Davisson et al. "Expression of human thymidylate synthase in *Escherichia coli*. (Additions and corrections)" *J. Biol. Chem.* (Dec. 2, 1994) 269(48):30740.

DeClercq "In search of a selective antiviral chemotherapy" *Clin. Microbiol. Rev.* (Oct. 1997) 10(4):674-693.

Drake et al. "Resistance to Tomudex (ZD1694): Multifactorial in Human Breast and Colon Carcinoma Cell Lines" *Biochem. Pharmacol.* (1996) 51(10):1349-1355.

Eccles et al. "Significance of the c-*erbB* family of receptor tyrosine kinases in metastatic cancer and their potential as targets for immunotherapy" *Invasion Metastasis* (1994-95) 14(1-6):337-348.

Eisenbrand et al. "An approach towards more selective anticancer agents" *J. Synthetic Organic Chem.* (1996) 10:1246-1258.

Evard et al. "An in vitro nucleoside analog screening method for cancer gene therapy" *Chem. Abstracts* (1996) 126:Abstract No. 26514.

Felip et al. "Overexpression of c-*erbB*-2 in epithelial ovarian cancer" *Cancer* (Apr. 15, 1995) 75(8):2147-2152.

Finch "Radiation Injury" In: Harrison's Principles of Internal Medicine, 12th Edition, McGraw-Hill, Inc., New York, NY (1991) 2204-2208.

Finer-Moore et al. "Refined structures of substrate-bound and phosphate-bound thymidylate synthase from Lactobacillus casei" J. Mol. Biol. (1993) 232:1101-1116.

Finer-Moore et al. "Crystal structure of thymidylate synthase from T4 phage: Component of a deoxynucleoside triphosphate-synthesizing complex" Biochemestry (1994) 33:15459-15468.

Firestone et al. "A comparison of the effects of antitumor agents upon normal human epidermal keratinocytes and human squamous cell carcinoma" Chem Abstracts (1990) 113:Abstract No. 254.

Garrett et al. "Thymidylate synthetase. Catalysis of dehalogenation of 5-bromo-and 5-iodo-2'-deoxyuridylate" Biochemistry (1979) 18(13):2798-2804.

Goldberg et al. "Novel cell imaging techniques show induction of apoptosis and proliferation in mesothelial cells by asbestos" Am. J. Respir. Cell Mol. Biol. (1997) 17:265-271.

Gros et al. "Isolation and expression of a complementary DNA that confers mutidrug resistance" Nature (Oct. 1986) 323:728-731.

Gros et al. "Mammalian multidrug resistance gene: Complete cDNA sequence indicates strong homology to bacterial transport proteins" Cell (Nov. 7, 1986) 47:371-380.

Gros et al. "Isolation and characterization of DNA sequences amplified in multidrug-resistant hamster cells" PNAS USA (Jan. 1986) 83:337-341.

Gudkov et al. "Cloning and characterization of DNA sequences amplified in multidrug-resistant djungarian hamster and mouse cells" Somat. Cell Mol. Genet. (1987) 13(6):609-619.

Hardy et al. "Atomic structure of thymidylate synthase: Target for rational drug design" Science (Jan. 23, 1987) 235:448-455.

Harris et al. "Adenovirus-mediated p53 gene transfer inhibits growth of human tumor cells expressing mutant p53 protein" Cancer Gene Ther. (1996) 3(2):121-130.

Hashimoto et al. "Simple separation of tritiated water and [$^3$H]deoxyuridine from [5-$^3$H]deoxyuridine 5'-monophosphate in the thymidylate synthase assay" Anal. Biochem. (1987) 167:340-346.

Hengstschläger et al. "The role of p16 in the E2F-dependent thymidine kinase regulation" Oncogene (1996) 12:1635-1643.

Holý et al. "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base" J. Med. Chem. (1999) 42(12):2064-2086.

Horikoshi et al. "Quantitation of thymidylate synthase, dihydrofloate reductase, and DT-diaphorase gene expression in human tumors using the polymerase chain reaction" Cancer Res. (Jan. 1, 1992) 52:108-116.

Horn et al. "Fialuridine is phosphorylated and inhibits DNA synthesis in isolated rat hepatic mitochondria" Antivir. Res. (1997) 34:71-74.

Huang and Santi "Active site general catalysts are not necessary for some proton transfer reactions of thymidylate synthase" Biochemistry (1997) 36:1869-1873.

Hudziak et al. "Selection for transformation and met protooncogene amplification in NIH 3T3 fibroblasts using tumor necrosis factor α" Cell Growth & Differentiation (1990) 1:129-134.

Husak et al. "Pseudotumour of the tongue caused by herpes simplex virus type 2 in an HIV-1 infected immunosuppressed patient" Brit. J. Dermatol. (1998) 139:118-121.

Imai et al. "Studies on phosphorylation. IV. Selective phosphorylation of the primary hydroxyl group in nucleosides" J. Org. Chem. (Jun. 1969) 34(6):1547-1550.

Johnston et al. "Production and characterization of monoclonal antibodies that localize human thymidylate synthase in the cytoplasm of human cells and tissue" Cancer Res. (Dec. 15, 1991) 51:6668-6676.

Johnston et al., "The role of thymidylate synthase expression in prognosis and outcome of adjuvant chemotherapy in patients with rectal cancer" J. Clin. Oncol. (Dec. 1994) 12(12):2640-2647.

Kamb "Cyclin-dependent kinase inhibitors and human cancer" Curr. Top. Microbiol. Immunol. (1998) 227:139-148.

Katki et al. "Prodrugs activated by thymidylate synthase: Treatment of tumors with deoxyuridine analogs" Proc. Amer. Assoc. Cancer Res. (Mar. 1998) 39:Abstract No. 1275.

Klecker et al. "Toxicity, metabolism, DNA incorporation with lack of repair, and lactate production for 1-(2'-fluoro-2'-deoxy- β - D-arabinofuranosyl)-5-iodouracil in U-937 and MOLT-4 cells" Mol. Pharmacol. (1994) 46:1204-1209.

Knighton et al. "Structure of and kinetic channelling in bifunctional dihydrofolate reductase-thymidylate synthase" Nature Struct. Biol. (Mar. 1994) 1(3):186-194.

Kodama et al. "Evaluation of antiherpetic compounds using a gastric cancer cell line: Pronounced activity of BVDU against herpes simplex virus replication" Microbiol. Immunol. (1996) 40(5):359-363.

Kumar et al. "Synthesis and biological evaluation of some cyclic phosphoramidate nucleoside derivatives" J. Med. Chem. (Sep. 1990) 33(9):2368-2374.

Kundu et al. "Synthesis and biological activities of [E]-5-(2-acylvinyl) uracils" Eur. J. Med. Chem. (1993) 28:473-479.

Kuroboshi and Hiyama "A facile synthesis of difluoromethylene compounds by oxidative fluorodesulfurization of dithioacetals using tetrabutylammonium dihydrogentrifluoride and N-halo compounds" SYNLETT (Dec. 1991) pp. 909-910.

Kuroboshi and Hiyama "A facile synthesis of α,α-difluoroalkyl ethers and carbonyl fluoride acetals by oxidative desulfurization-fluorination" SYNLETT (Apr. 1994) pp. 251-252.

Lam "Application of combinatorial library methods in cancer research and drug discovery" Anti-Cancer Drug Design (1997) 12:145-167.

Larsson et al. "Thymidylate synthase in advanced gastrointestinal and breast cancers" Acta Oncologica (1996) 35(4):469-472.

Li et al. "Lack of functional retinoblastoma protein mediates increased resistance to antimetabolites in human sarcoma cell lines" PNAS USA (Oct. 1995) 92:10436-10440.

Livingstone et al. "Altered cell cycle arrest and gene amplification potential accompany loss of wild- type p53" Cell (Sept. 18, 1992) 70:923-935.

Masters and Altardi "The nucleotide sequence of the cDNA coding for the human dihydrofolic acid reductase" Gene (1983) 21:59-63.

McGuigan "Aryl phosphate derivatives of AZT retain activity against HIV1 in cell lines which are resistant to the action of AZT" Antivir. Res. (1992) 17:311-321.

McGuigan "Intracellular delivery of bioactive ATZ nucleotides by aryl phosphate derivatives of AZT" J. Med. Chem. (1993) 36:1048-1052.

McGuigan "Aryl phosphoramidate derivatives of d4T have improved anti-HIV efficacy in tissue culture and may act by the generation of a novel intracellular metabolite" J. Med. Chem. (1996) 39:1748-1753.

McGuigan et al. "Synthesis and evaluation of some masked phosphate esters of the anti-herpetic drug 882C (netivudine) as potential antiviral agents" Antivir. Chem. Chemoth. (1998) 9:187-197.

McKay et al. "Broad spectrum aminoglycoside phosphotransferase type III from Enterococcus: Overexpression, purification, and substrate specificity" Biochemistry (1994) 33:6936-6944.

Meden et al. "Elevated serum levels of a c-erbB-2 oncogene product in ovarian cancer patients and in pregnancy" J. Cancer Res. Clin. Oncol. (1994) 120:378-381.

Montfort and Weichsel "Thymidylate synthase: Structure, inhibition, and strained conformations during catalysis" Pharmacol. Ther. (1997) 76(1-3):29-43.

Montgomery et al., "Phosphonate analogue of 2'-deoxy-5-fluorouridylic acid" J. Med. Chem. (1979) 22(1):109-111.

Murakami and Sekiya "Accumulation of genetic alterations and their significance in each primary human cancer and cell line" Mutat Res. (1998) 400(1-2):421-437.

Nakano et al., "Critical role of phenylalanine 34 of human dihydrofolate reductase in substrate and Inhibitor binding and in catalysis" Biochemistry (1994) 33:9945-9952.

Nooter and Stoter "Molecular mechanisms of multidrug resistance in cancer chemotherapy" Path. Res. Pract. (1996) 192:768-780.

Osaki et al. "5-fluorouracil (5-FU) induced apoptosis in gastric cancer cell lines: Role of the p53 gene" Apoptosis (1997) 2:221-226.

Oshiro et al. "Genotoxic properties of (E)-5-(2-bromovinyl)-2'-deoxyuridine (BVDU)" Fundam. Appl. Toxicol. (1992) 18:491-498.

Park et al. "Chemotherapy efficacy of E-5-(2-bromovinyl)-2'-deoxyuridine for orofacial infection with herpes simplex virus type 1 in mice" *J. Infectious Diseases* (Jun. 1982) 145(6):909-913.

Perry et al. "Plastic adaptation toward mutations in proteins: Structural comparison of thymidylate synthases" *Proteins* (1990) 8:315-333.

Peters et al. "Thymidylate synthase and drug resistance" *Eur. J. Can.* (1995) 31A(7/8):1299-1305.

Roberts "An isotopic assay for thymidylate synthetase" *Biochemistry* (Nov. 1966) 5(11):3546-3548.

Rogulski et al. "Glioma cells transduced with an *Escherichia coil* CD/HSV-1 TK fusion gene exhibit enhanced metabolic suicide and radiosensitivity" *Hum. Gene Ther.* (Jan. 1, 1997) 8:73-85.

Roninson et al. "Amplification of specific DNA sequences correlates with multi-drug resistance in Chinese hamster cells" *Nature* (Jun. 14, 1984) 309:626-628.

Sauter et al. "Heterogeneity of *erb*B-2 gene amplification in bladder cancer" *Cancer Res.* (May 15, 1993) 53:2199-2203.

Schiffer et al. "Crystal structure of human thymidylate synthase: A structural mechanism for guiding substrates into the active site" *Biochemistry* (1995) 34:16279-16287.

Schimke "Gene amplification in cultured cells" *J. Biol.Chem.* (May 5,1988) 263(13):5989-5992.

Segovia "*Leishmania* gene amplification: A mechanism of drug resistance" *Ann. Trop. Med. Parasit.* (1994) 88(2)123-130.

Singh et al. "Studies on the preparation and isomeric composition of $^{186}$Re- and $^{188}$Re-pentavalent rhenium dimercaptosuccinic acid complex" *Nucl. Med. Commun.* (1993)14:197-203.

Slamon et al. "Human breast cancer: Correlation of relapse and survival with amplification of the HER-2/*neu* oncogene" *Science* (Jan. 9, 1987) 235:177-182.

Slamon et al. "Studies of the HER-2/*neu* proto-oncogene in human breast and ovarian cancer" *Science* (May 12, 1989) 244:707-712.

Snydman et al. "Analysis of trends in antimicrobial resistance patterns among clinical isolates of Bacteroides fragilis group species from 1990 to 1994" *Clin. Infect. Dis.* (1996) 23(Suppl. 1):S54-S65.

Staschke et al. "The in vitro anti-hepatitis B virus activity of FIAU [1-(2'-deoxy-2'-fluro-1-β-D-arabinofuranosyl-5-iodo)uracil] is selective, reversible, and determined, at least in part, by the host cell" *Antiviral Res.* (1994) 23:45-61.

Stout et al. "Structure-based design of inhibitors specific for bacterial thymidylate synthase" *Biochemistry* (1999) 38:1607-1617.

Sukumar and Barbacid "Specific patterns of oncogene activation in transplacentally induced tumors" *PNAS USA* (Jan. 1990) 87:718-722.

Takeishi et al. "Nucleotide sequence of a functional cDNA for human thymidylate synthase" *Nucl. Acid Res.* (1985) 13(6):2035-2043.

Tennant et al. "Antiviral activity and toxicity of fialuridine in the woodchuck model of hepatitis B virus infection" *Hepatology* (Jul. 1998) 28(1):179-191.

Ubeda and Habener "The large subunit of the DNA replication complex C (DSEB/RF-C140) cleaved and inactivated by Caspace-3 (CPP32/YAMA) during fas-induced apoptosis" *J. Biol. Chem.* (Aug. 1, 1997) 272(31):19562-19568.

van de Vijver et al. "Amplification of the *neu* (c-*erb*B-2)oncogene in human mammary tumors is relatively frequent and is often accompanied by amplification of the linked c-*erb*A oncogene" *Mol. Cell. Biol.* (May 1987) 7(5):2019-2023.

Volm et al. "Relationship of inherent resistance to doxorubicin, proliferative activity and expression of P-glycoprotein 170, and glutathione S-transferase-π in human lung tumors" *Cancer* (Aug. 15, 1992) 70(4):764-769.

Wang et al. "Identification and characterization of Ich-3, a member of the interleukin-1β converting enzyme (ICE)/Ced-3 family and an upstream regulator of ICE" *J. Biol. Chem.* (Aug. 23, 1996) 271(34):20580-20587.

Yin et al. "Wild-type p53 restores cell cycle control and inhibits gene amplification in cells with mutant p53 alleles" *Cell* (Sept. 18, 1992) 70:937-948.

Zhou et al. "Target protease specificity of the viral serpin CrmA" *J. Biol. Chem.* (Mar. 21, 1997) 272(12):7797-7800.

Bathe et al. "Increased thymidylate synthase gene expression in liver metastases from colorectal carcinoma: Implications for chemotherapeutic options and survival" *Cancer J. Sci. Am.* (1999) 5(1):34-40.

Belt et al. "Nucleoside Transport in Normal and Neoplastic Cells" *Advan. Enzyme Regul.* (1993) 33:235-252.

Bible et al. "Cytotoxic synergy between flavopiridol (NSC 649890, L86-8275) and various antineoplastic agents: the importance of sequence of administration" *Cancer Res.* (Aug. 15, 1997) 57(16):3375-80.

Chou and Talalay, "Quantitative analysis of dose-effect relationships: the combined effects of multiple drugs or enzyme inhibitors" *Adv. Enzyme Regul.* (1984) 22:27-55.

Curt "Cancer drug development: new targets for cancer treatment" *Oncologist* (1996) 1(3):II-III.

Curtin et al. "Mechanism of Cell Death following Thymidylate Synthase Inhibition: 2'-Deoxyuridine-5'-triphosphate Accumulation, DNA Damage, and Growth Inhibition following Exposure to CB3717 and Dipyridamole" *Cancer Res.* (May 1, 1991) 51:2346-2352.

Goel et al. "Selective Intraperitoneal Biochemical Modulation of Methotrexate by Dipyridamole" *J. Clin. Oncol.* (Feb. 1989) 7(2):262-269.

Gorlick et al. "Drug Resistance in Colon Cancer" *Semin. Oncol.* (Dec. 1999) 26(6):606-611.

Grem "Biochemical modulation of fluorouracil by dipyridamole: preclinical and clinical experience" *Semin Oncol.* (Apr. 1992) 19(2 Suppl 3):56-65.

Griffith et al. "Differential Inhibition of Nucleoside Transport Systems in Mammalian Cells by a New Series of Compounds Related to Lidoflazine and Mioflazine" *Biochem. Pharmacol.* (1990) 40(10):2297-2303.

Kraupp et al. "Membrane Transport of Nucleobases: Interaction with Inhibitors" *Gen. Pharmacol.* (1995) 26(6):1185-1190.

Lackey et al. "Enzyme-catalyzed therapeutic agent (ECTA) design: activation of the antitumor ECTA compound NB1011 by thymidylate synthase" Biochem. Pharmacol. (2001) 61:179-189.

Lehman et al. "Modulation of RTX cytotoxicity by thymidine and dipyridamole in vitro: implications for chemotherapy" Cancer Chemother. Pharmacol. (2000) 45:142-148.

Leichman et al. "Quantitation of Intratumoral Thymidylate Synthase Expression Predicts for Disseminated Colorectal Cancer Response and Resistance to Protracted-Infusion Fluorouracil and Weekly Leucovorin" J. Clin. Oncol. (Oct. 1997) 15(10):3223-3229.

Leichman "Thymidylate synthase as a predictor of response" Oncol. (Aug. 1998) 12(8Suppl.6):43-47.

Lenz et al. "Rapid quantitative PCR for determination of relative gene expressions in tissue specimens" PCR Methods Appl. (1995) 4:305-308.

Mahony et al. "Dipyridamole Kinetics" *Clin. Pharmacol. Ther.* (Mar. 1982) 31(3):330-338.

Nelson et al. "Potentiation of Methotrexate Toxicity by Dipyridamole" *Cancer Res.* (Jun. 1984) 44:2493-2496.

Ramu et al. "Circumvention of Adriamycin Resistance by Dipyridamole Analogues: A structure-activity relationship Study" *Int. J. Cancer* (' 1989) 43:487-491.

Tsavaris et al. "Multimodal biochemical modulation of 5-fluorouracil activity in advanced colorectal cancer with allopurinol, folinic acid and dipyridamol" *J. Chemother.* (1990) 2(2):123-126.

Wolff et al. "Antibody-directed enzyme prodrug therapy with the T268G mutant of human carboxypeptidase A1: in vitro and in vivo studies with prodrugs of methotrexate and the thymidylate synthase" *Bioconjugate Chemistry* (1999) 10(1):38-48.

Balzarini et al. "Marked inhibitory activity of masked aryloxy aminoacyl phosphoramidate derivatives of dideoxynucleoside analogues against visna virus Infection" *Journal Acquired Immune Deficiency Syndromes and Human Retrovirology* (1998) 17:296-302.

Balzarini et al., "Increased sensitivity of thymidine kinase-deficient (TK-) tumor cell lines to the cell growth inhibitory effects of (E)-5-(2-bromovinyl)-2'-deoxyuridine (BVDU) and related compounds", Anticancer Research, vol. 6, 1986, pp. 1077-1084, Belgium, 1986.

Balzarini et al. "Anti-HIV and anti-HBV activity and resistance profile of 2',3'-dideoxy-3'-thiacytidine (3TC) and its arylphosphoramidate derivative CF 1109" *Biochemical and Biophysical Research Communication* (1996) 225:363-369.

Libra et al. (2004) Thymidylate synthase mRNA levels are increased in liver metastases of colorectal cancer patients resistant to fluoropyrimidine-based chemotherapy, BMC Cancer 4:11.

Pardo et al. (1987) "The incorporation of deoxyuridine monophosphate in DNA increases the sister-chromatid exchange yield," *Exp Cell Res.* 168:507-517.

Pupa et al. (1993) "The extracellular domain of the c-erbB-2 oncoprotein is released from tumor cells by proteolytic cleavage," Oncogene 8:2917-2923.

* cited by examiner

How to find a TS lead molecule:
D sign of th High Throughput Screen
e.g., Using Thymidylat Synthase as
the Target Enzyme How to find a TS lead molecule:
Replacement of two enzymes,
e.g., Thymidylate Synthase (TS)
and Thymidine Kinase (TK)

ENZYME CATALYZED THERAPEUTIC COMPOUNDS

CROSS-REFERENCE TO RELATED APPLICATIONS

This is a continuation application of U.S. Ser. No. 09/856,127, filed Oct. 10, 2001, now U.S. Pat. No. 6,683,061, issued Jan. 27, 2004, which is the National Stage of International Application No. PCT/US00/20008, filed Jul. 21, 2000, which in turn claims the benefit under 35 U.S.C. § 119(e) to the following U.S. provisional applications, U.S. Ser. Nos. 60/145,356; 60/145,437; and 60/191,315, filed Jul. 22, 1999; Jul. 23, 1999 and Mar. 21, 2000, respectively, the contents of which are hereby incorporated by reference into the present disclosure.

TECHNICAL FIELD

The present invention relates to the field of drug discovery and specifically, the design of prodrugs that are substrates for endogenous intracellular enzymes that are overexpressed in pathological cells.

BACKGROUND OF THE INVENTION

Throughout and within this disclosure, various publications are referenced by first author and date, patent number or publication number. The full bibliographic citation for each reference can be found within the specification or at the end of this application, immediately preceding the claims. The disclosures of these publications are hereby incorporated by reference into this disclosure to more fully describe the state of the art to which this invention pertains.

Cancer is one of the most commonly fatal human diseases worldwide. Treatment with anticancer drugs is an option of steadily increasing importance, especially for systemic malignancies or for metastatic cancers that have passed the state of surgical curability. Unfortunately, the subset of human cancer types that are amenable to curative treatment today is still rather small (Haskell, C. M. (1995)) resulting in about 600,000 deaths per year. See, Cancer Facts & Figures, 1999 American Cancer Society. Progress in the development of drugs that can cure human cancer is slow, with success limited to a few hematological malignancies and fewer solid tumor types (Dorr and Van Hoff (1994)). Progress in discovering therapies that are based upon disease mechanism offers opportunities for future success. (Cobleigh, M. A. et al. (1999); and Roth, J. A. et al. (1999)).

The heterogeneity of malignant tumors with respect to their genetics, biology and biochemistry as well as primary or treatment-induced resistance to therapy mitigate against curative treatment. Moreover, many anticancer drugs display only a low degree of selectivity, causing often severe or even life threatening toxic side effects, thus preventing the application of doses high enough to kill all cancer cells. Searching for anti-neoplastic agents with improved selectivity to treatment-resistant pathological, malignant cells remains therefore a central task for drug development.

Cancer cells are characterized by uncontrolled growth, de-differentiation and genetic instability. The instability expresses itself as aberrant chromosome number, chromosome deletions, rearrangements, loss or duplication beyond the normal diploid number. (Wilson, J. D. et al. (1991)). This genomic instability may be caused by several factors. One of the best characterized is the enhanced genomic plasticity which occurs upon loss of tumor suppressor gene function (e.g., Almasan, A. et al. (1995a) and Almasan, A. et al. (1995b)). The genomic plasticity lends itself to adaptability of tumor cells to their changing environment, and may allow for the more frequent mutation, amplification of genes, and the formation of extrachromosomal elements (Smith, K. A. et al. (1995) and Wilson, J. D. et al. (1991)). These characteristics provide for mechanisms resulting in more aggressive malignancy because it allows the tumors to rapidly develop resistance to natural host defense mechanisms, biologic therapies (see, Wilson, J. D. et al. (1991) and Shepard, H. M. et al. (1988)), as well as to chemotherapeutics (see, Almasan, A. et al. (1995a); and Almasan, A. et al. (1995b)).

In addition, the clinical usefulness of a chemotherapeutic agent may be severely limited by the emergence of malignant cells resistant to that drug. A number of cellular mechanisms are probably involved in drug resistance, e.g., altered metabolism of the drugs, impermeability of the cell to the active compound or accelerated drug elimination from the cell, altered specificity of an inhibited enzyme, increased production of a target molecule, increased repair of cytotoxic lesions, or the bypassing of an inhibited reaction by alternative biochemical pathways. In some cases, resistance to one drug may confer resistance to other, biochemically distinct drugs. An alternative mechanism of resistance to cancer chemotherapeutics occurs via the functional loss of tumor suppressor genes. The best characterized of these are p53, RB and p16. (Funk, J. O. 1999; and Teh, B. T. (1999)). Loss of function of these gene products leads to depressed expression of enzymes commonly targeted by anti-cancer drugs (e.g., 5-fluorouridyl ("5FU")/thymidylate synthase and methotrexate/dihydrofolate reductase). (Lee, V. et al. (1997); Lenz, H. J. et al. (1998); and Fan, J. and Bertino, J. (1987)). Amplification of certain genes is involved in resistance to biologic and chemotherapy. Amplification of the gene encoding dihydrofolate reductase is related to resistance to methotrexate, while overexpression/amplification of the gene encoding thymidylate synthase is related to resistance to treatment with 5-fluoropyrimidines. (Smith, K. A. et al. (1995)). Table 1 summarizes some prominent enzymes in resistance to biologic and chemotherapy.

TABLE 1

Enzymes Overexpressed in Resistance to Cancer Chemotherapy

| Enzyme | Biologic or Chemotherapy | Referenced (Examples) |
| --- | --- | --- |
| Thymidylate synthase | Uracil-based | Lönn, U. et al. (1996) |
|  | Folate-based | Kobayashi, H. et al. (1995) |
|  | Quinazoline-based | Jackman, A.L. et al. (1995a) |
| Dihydrofolate reductase | Folate-based | Banerjee, D. et al. (1995) |
|  |  | Bertino, J.R.. et al. (1996) |

TABLE 1-continued

Enzymes Overexpressed in Resistance to Cancer Chemotherapy

| Enzyme | Biologic or Chemotherapy | Referenced (Examples) |
|---|---|---|
| Tyrosine kinases | TNF-alpha | Hudziak, R.M. et al. (1988) |
|  | Multidrug resistance | Stühlinger, M. et al. (1994) |
| MDR-associated proteins (ABC P-gp proteins) | Multidrug resistance | Simon, S.M. and Schindler, M. (1994) Gottesman, M.M. et al. (1995) |
| CAD* | PALLA** | Smith, K.A. et. Al. (1995) Dorr, R.T. and Von Hoff, D.D., eds. (1994) |
| Topoisomerase I (Colon & Prostate Cancers) | Camptothecin | Husain et al. (1994) |
| Ribonucleotide reductase | Hydroxyurea | Wettergren, Y. et al. (1994) Yen, Y. et al. (1994) |

*CAD = carbamyl-P synthase, aspartate transcarbamylase, dihydroorotase
**PALA = N-(phosphonacetyl)-L-aspartate The poor selectivity of anticancer agents has been recognized for a long time and attempts to improve selectivity and allow greater doses to be administered have been numerous. One approach has been the development of prodrugs. Prodrugs are compounds that are toxicologically benign but which may be converted in vivo to therapeutically active products. In some cases, the activation occurs through the action of a non-endogenous enzyme delivered to the target cell by antibody ("ADEPT" or antibody-dependent enzyme prodrug therapy (U.S. Pat. No. 4,975,278)) or gene targeting ("GDEPT" or gene dependent enzyme-prodrug therapy (Melton, R. G. and Sherwood, R. E. (1996)). These technologies have severe limitations with respect to their ability to exit the blood and penetrate tumors. See, Connors, T. A. and Knox, R. J. (1995).

A number of nucleotide and nucleoside analogs have been developed and tested as both anti-tumor and anti-viral agents. For example 5-flurouracil (5FU) and 5-fluoro-deoxyuridine (5FUdR) have been widely used as chemotherapeutic agents based on their ability to be converted intracellularly into inhibitors of the thymidylate synthase (TS) enzyme. As with many other enzyme inhibitory chemotherapeutic agents, cancer therapy using 5FU frequently leads to selection for aggressive drug resistant tumor cells which are refractory to further treatment with this drug. (Aschele, C. et al. (1994); Mader, R. M. et al. (1998); Lönn, U. et al. (1996); Paradiso, A. et al. (2000); and Edler, D. et al. (2000)).

Particular attention has also been paid to halogenated nucleoside analogs such as (E)-5-(2-Bromovinyl)-2'-deoxyuridine (BVdU). These types of compounds were originally developed as anti-viral agents based on the observation that they required phosphorylation to the monophosphate nucleotide form in order to elicit cytotoxic responses and this phosphorylation was preferentially accomplished by herpes virus thymidine kinase (TK) enzymes. BVdU and related compounds have consistently shown limited toxicity to normal mammalian cells, while they have been effective at killing virally infected cells. (DeClerq, E. et al. (1997)).

Throughout the extensive testing of nucleoside analogs such as BVDU as anti-viral and anti-cancer agents, they have consistently been reported to have minimal toxicity to both normal and cancer cells. These observations have been supported by results demonstrating the preferential phosphorylation of such compounds by viral thymidine kinase enzymes, which explains the low toxicity of these compounds for mammalian cells. Thus, BVdU and related nucleoside analogs have not been developed as anti-cancer therapeutic agents. (De Clerq, E. et al. (1997)).

DISCLOSURE OF THE INVENTION

This invention provides novel compounds that selectively inhibit the proliferation of pathological cells, for example, pathological cells that endogenously overexpress a target enzyme that confers resistance to biologic and chemotherapeutic agents. The enzyme acts on a prodrug compound of this invention to 1) convert it to a cellular toxin and/or 2) release a toxic byproduct. In another aspect of this invention, the product of an initial reaction with a resistance enzyme, is subsequently fully activated by a common cellular enzyme such as an acylase, phosphatase or other "housekeeping" enzyme (Voet, et al. (1995)) or common cellular constituent (e.g., water) to release the toxic byproduct from the prodrug.

In one embodiment, the activity of the target enzyme has been greatly enhanced in a target cell as a result of loss of tumor suppressor function and/or selection resulting from previous exposure to chemotherapy. In another embodiment, the pathological cell contains a target enzyme that is an expression product of an infectious agent in the cell. The expression product can confer antibiotic resistance.

Another aspect of this invention includes assays for screening for new prodrugs that can be activated by target enzymes. Kits to perform such assays containing the reagents and instructions necessary to complete the assay and analyze the results are also provided by this invention.

Further provided by this invention is a method for treating a subject by delivering to the subject a prodrug as described herein. The prodrugs of this invention may be used alone or in combination with other chemotherapeutics or alternative anti-cancer therapies such as radiation.

A further aspect of this invention is the preparation of a medicament for use in treating a subject suffering from a pathology characterized by cells expressing a target enzyme.

A still further aspect of this invention is a method for identifying the optimal therapeutic for a subject, by isolating cells expressing a target enzyme and contacting the cells with at least one of the prodrugs of this invention, and then identifying which of the one or more prodrugs inhibits the proliferation or kills the cells, thereby identifying the optimal therapeutic for the subject.

The prodrugs of this invention have the following structure:

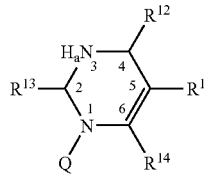

or tautomers thereof;

wherein $R^{12}$ or $R^{13}$ may be the same or different and are selected from the group consisting of oxo, OH or $NHNH_2$;

wherein if a is 0 or 1, providing that if a is 0 and $R^{13}$ is oxo, then a double bond exits between position 3 and 4 and $R^{12}$ is $NHNH_2$ or if a is 0 and $R^{12}$ is oxo, then a double bond exists between position 2 and 3 and $R^{13}$ is $NHNH_2$; or if a is 1, then $R^{12}$ and $R^{13}$ are both oxo;

wherein $R^1$ is a substituent having the formula:

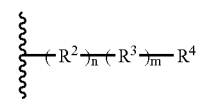

wherein $R^2$ and $R^3$ are independently an unsaturated or a saturated hydrocarbyl group;

wherein n is 0 or an integer from 1 to 10 and m is 0 or 1; and wherein $R^4$ is selected from the group consisting of F, Cl, Br, I, CN, $SO_3H$, $CO_2H$, $CO_2CH_2CH_3$, $CO_2CH_3$, $SI(CH_3)_3$, CHO, $NO_2$, $CF_3$, $CCl_3$, $CH=C(R^{15})_2$ or a substituent having the structure:

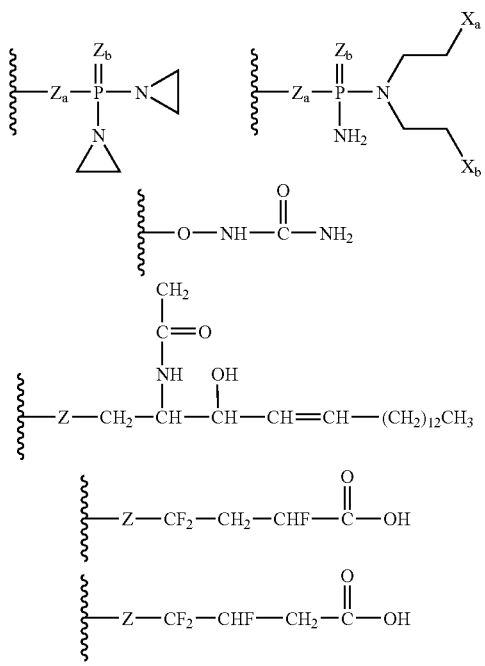

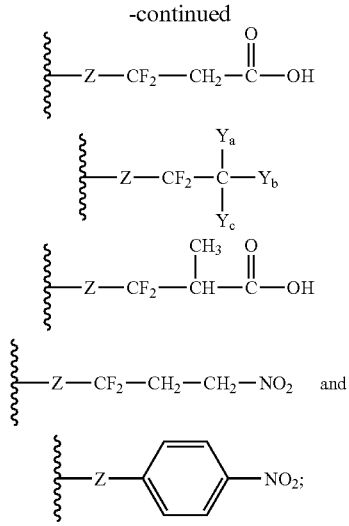

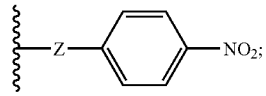

wherein $X_a$ and $X_b$ are independently the same or different and are selected from the group consisting of Cl, Br, I, and a potent leaving group;

wherein $Y_a$, $Y_b$ or $Y_c$ are independently the same or different and are H or F;

wherein Z, $Z_a$ and $Z_b$ are independently the same or different and are O or S; and wherein $R^{14}$ is H or F, providing if $R^{14}$ is F, then a is 1 and $R^{12}$ and $R^{13}$ are both oxo; and wherein Q is selected from the group consisting of a sugar, a carbocyclic, and an acyclic compound, or a masked phosphate derivative or phosphoramidate derivative thereof.

BRIEF DESCRIPTION OF THE FIGURES

The concepts described herein are displayed graphically in FIGS. 1A and 1B using the example of the thymidylate synthase enzyme and the compound NB1011™.

MODES FOR CARRYING OUT THE INVENTION

Figure 1A:
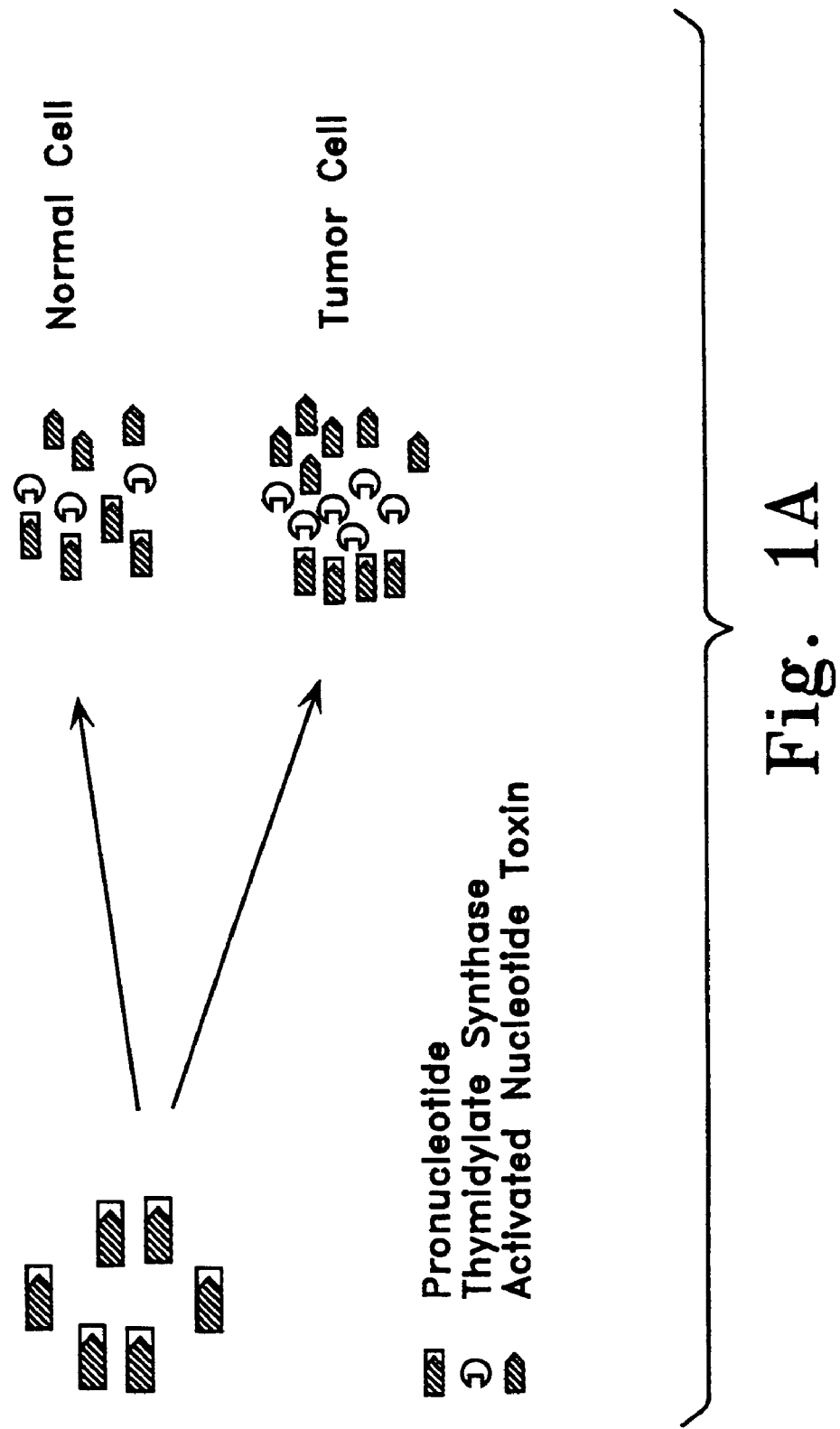
FIG. 1A shows how higher levels of TS in tumor cells can lead to preferential generation of toxin.

The practice of the present invention will employ, unless otherwise indicated, conventional techniques of molecular biology, microbiology, cell biology, organic chemistry, medicinal chemistry and recombinant DNA, which are within the skill of the art. See, e.g., Sambrook et al., MOLECULAR CLONING: A LABORATORY MANUAL, $2^{nd}$ edition (1989); CURRENT PROTOCOLS IN MOLECULAR BIOLOGY, F. M. Ausubel et al. eds., (1987); the series METHODS IN ENZYMOLOGY, Academic Press, Inc.; PCR 2: A PRACTICAL APPROACH, M. J. MacPherson et al., eds. (1995); Spector, D. L. et al. (1998) CELLS: A LABO- RATORY MANUAL, Vols I to III, Cold Spring Harbor Press; and ANIMAL CELL CULTURE, R. I. Freshney, ed. (1987).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "overexpression" shall mean at least 2 fold, preferably 3 fold, and more preferably 4 fold and most preferably 5 fold or more expression over normal levels or levels measured from normal or non-pathological cells.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

"target" or "pathological" cells include hyperproliferative cells that are de-differentiated, immortalize neoplastic, malignant, metastatic or transformed. Examples include, but are not limited to cancer cells such as sarcoma cells, leukemia cells, carcinoma cells, or adenocarcinoma cells. Specified cancers include, but are not limited to breast cancer cells, hepatoma cells, liver cancer cells, pancreatic carcinoma cells, oesophageal carcinoma cells, bladder cancer cells, gastrointestinal cancer cells, ovarian cancer cells, skin cancer cells, prostate cancer cells, and gastric cancer cells.

Target or pathological cells overexpress an intracellular enzyme that is related to any of a loss of tumor suppressor gene product function, drug resistance or genetic instability. Alternatively, resistance to one drug may confer resistance to other, biochemically distinct drugs. Unlike prior art therapies directed to creating more potent inhibitors of endogenous, intracellular enzymes, this invention exploits the higher enzyme activity associated with therapy-resistant diseased cells and tissues versus normal cells and tissues and does not rely on inhibiting the enzyme. The term "target enzyme" is used herein to define enzymes having one or more of the above noted characteristics.

Gene products activated or overexpressed and related to drug resistance include, but are not limited to thymidylate synthase (TS) (Lönn, U. et al. (1996); Kobayashi, H. et al. (1995); and Jackman, A. L. et al. (1995b)), dihydrofolate reductase (Baneoee, D. et al. (1995) and Bertino, J. R. et al. (1996)), tyrosine kinases (TNF-α, Hudziak, R. M. et al. (1988)) and multidrug resistance (Stühlinger, M. et al. (1994)); Akdas, A. et al. (1996); and (Tannock, I. F. (1996)); and ATP-dependent multidrug resistance associated proteins (Simon, S. M. and Schindler, M. (1994)) and, in some diseases including colon and prostate cancer, topoisomerase I (Husain et al. (1994)).

Amplification of dihydrofolate reductase (DHFR) is related to resistance to methotrexate while amplification of the gene encoding thymidylate synthase is related to resistance to tumor treatment with 5-fluoropyrimidine. Amplification of genes associated with drug resistance can be detected and monitored by a modified polymerase chain reaction (PCR) as described in Kashini-Sabet, et al. (1988), U.S. Pat. No. 5,085,983, or the method described herein. Acquired drug resistance can be monitored by the detection of cytogenetic abnormalities, such as homogeneous chromosome staining regions and double minute chromosomes both of which are associated with gene amplification. Alternative assays include direct or indirect enzyme activity assays and each of which are associated with gene amplification (e.g., Carreras and Santi (1995)); other methodologies (e.g. polymerase chain reaction, Houze, T. A. et al. (1997) or immunohistochemistry (Johnson, P. G. et al. (1997)).

The enzyme glutathione-S-transferase has been shown to be occasionally elevated in some human tumors (Morgan, A. S. et al. (1998)), but nevertheless is excluded from "target enzyme" as used herein because it is a member of a gene family encoding enzymes with overlapping specificities.

In sum, the prodrugs of the subject invention are distinguishable from conventional therapeutics on the basis that the target enzymes of this invention are commonly overexpressed, over-accumulated or activated in pathological cells versus normal cells. The most important principles that distinguishes the current invention from other approaches are:

(1) This invention describes the synthesis of substrates for enzymes like thymidylate synthase. The overexpressed enzyme will convert prodrugs to toxin, preferentially in diseased cells. Previous approaches have mostly relied on inhibitors of these enzymes. The inhibitors lead to amplified expression of the enzyme, and subsequent resistance to treatment (see, e.g., Lönn, U. et al. (1996); Paradiso, A. et al. (2000); and Edler, D. (2000)).

(2) The current approach is also distinguishable from other "substrate-prodrug" approaches, e.g., the glutathione-S-transferase enzymes (see, e.g., Morgan, A. S. et al. (1998)). The enzymes of the GST family are expressed at increased levels in response to toxic insult to the cell. The GST family of enzymes has overlapping substrate specificities, which makes it difficult to design a substrate reactive with only a single species of enzyme with elevated expression in a cancer cell (Morgan, A. S. et al. (1998)). Because the target enzymes of the current invention (e.g., thymidylate synthase, dihydrofolate reductase and thymidine kinase) are unique with respect to its structure and substrate specificity, it is facile to design unique substrates. Several examples of substrates for thymidylate synthase are provided infra.

(3) In some cases the gene encoding the target enzyme (e.g., thymidylate synthase) may have undergone mutation to give resistance to inhibitors, (Barbour, K. W. et al. (1992) and Dicken, A. P. et al. (1993)) but will still be capable of carrying out reaction with non-inhibitor substrate prodrugs.

(4) An advantage of this approach is that loss of tumor suppressor function is critical to development of malignancy. The majority of tumor cells have lost one of the p53, RB or p16 tumor suppressor functions. (Funk, J. O. (1999); Banerjee, D. (1998); and Teh, B. T. et al. (1999)). Such a loss results in increased expression of resistances enzymes (e.g., thymidylate synthase), independent of previous exposure to chemotherapy. The prodrugs described herein will be useful in treating early stages of malignancy, as well as disease previously treated with chemotherapy. Substrates for enzymes like GST include many compounds unrelated to chemotherapy. (Whalen and Boyer (1998)).

Figure 1B:
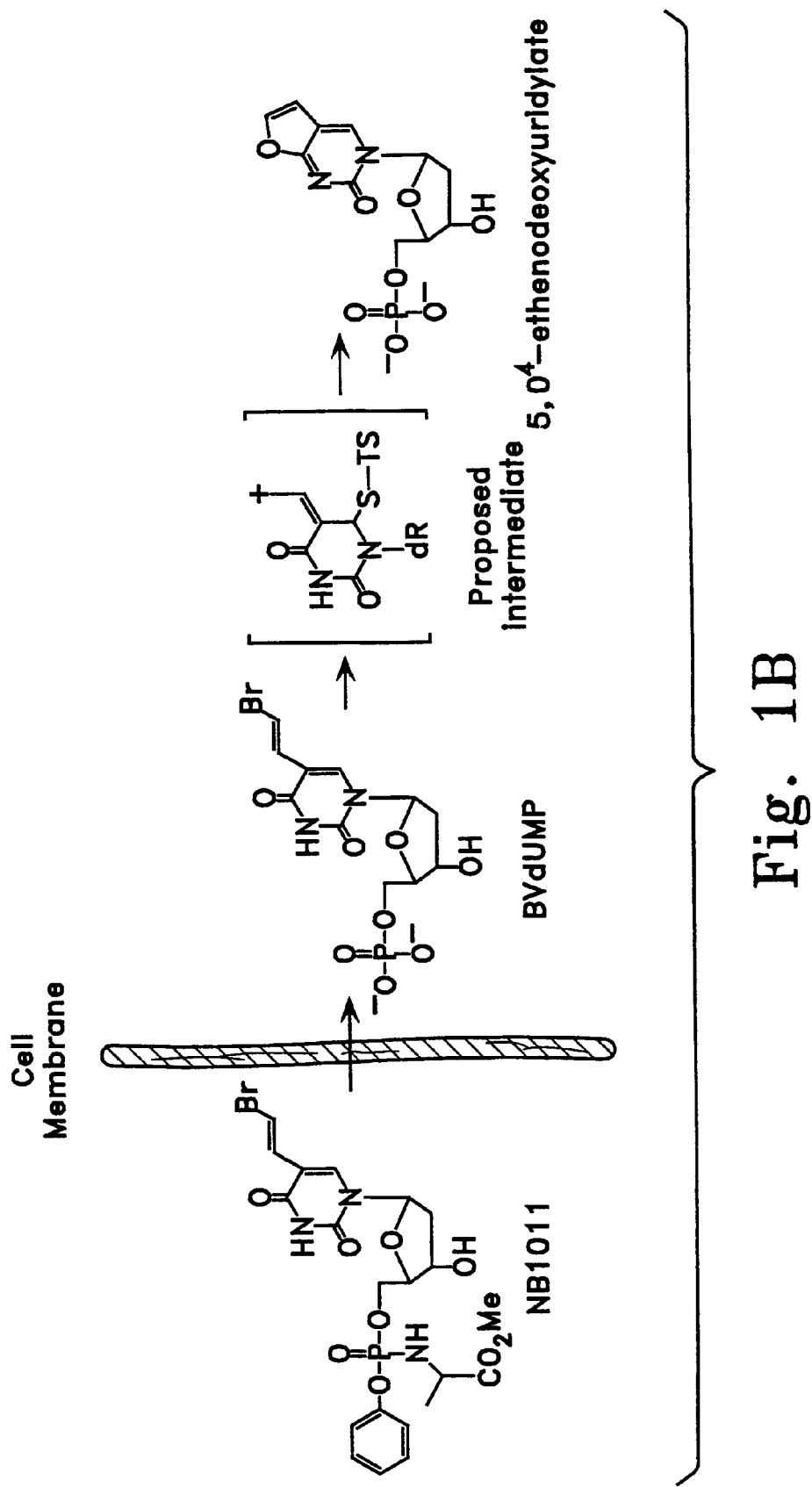
FIG. 1B shows the conversion of NB1011™ to BVdUMP, and subsequent interaction with TS to generate nucleotide toxin.

The concepts described above are displayed graphically in FIG. 1A and 1B using the example of the thymidylate synthase enzyme and the compound NB1011™.

In an alternative embodiment, the target cell is defined by its resistance to a drug or compound unrelated to cancer. In this case, the cell is infected with a microorganism that confers resistance to an antibiotic, e.g. beta-lactamase. Organisms include bacteria, yeast and parasites, such as trypanosomes. Table 2 provides a list of enzymes targeted by this approach in infectious disease.

TABLE 2

Enzymes Overexpressed in Infectious Disease, and which Contribute to Drug Resistance

| Enzyme | Provides increased Resistance to: |
| --- | --- |
| Beta-lactamases | Penicillin and other beta-lactam containing antibiotics |
| Aminoglycosidase, or aminoglycoside midifying enzymes | Aminoglycoside antibiotics (e.g., streptomycin, gentamycin) |
| Chloramphenicol transacetylase | Chloramphenicol |
| Dihydrofolate reductase | Trimethoprim |

Reference: Mechanisms of Microbial Disease, 2$^{nd}$ Ed., M. Schaechter, G. Medloff, B.I. Eisenstein, Editor TS Satterfield. Publ. Williams and Wilkins, p. 973 (1993).

The prodrugs of this invention are selected from the group consisting of the L and D isomers of compounds having the structures:

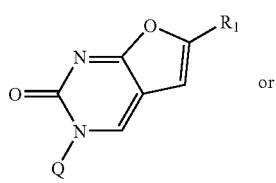

I.

or

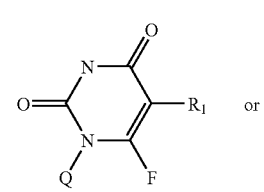

II.

or

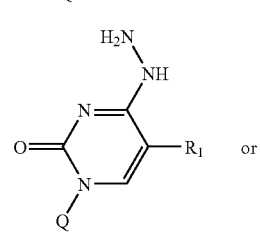

III.

or

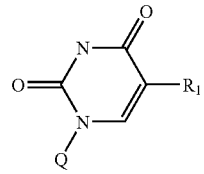

IV.

wherein:

$R^1$ is a moiety of the formula:

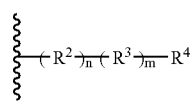

with the proviso that in compound I, n can be 0.

$R^2$ is a divalent electron conduit moiety selected from the group consisting of an unsaturated hydrocarbyl group; an aromatic hydrocarbyl group comprising one or more unsaturated hydrocarbyl groups; and, a heteroaromatic group comprising one or more unsaturated hydrocarbyl groups;

$R^3$ is selected from the group consisting of:

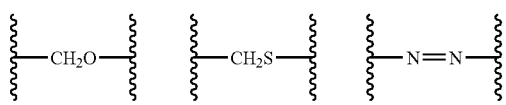

$R^5$ may be the same or different and is independently a linear or branched alkyl group having from 1 to 10 carbon atoms, or a cycloalkyl group having from 3 to 10 carbon atoms, or a halogen (e.g., F, Cl, Br, I);

or the group:

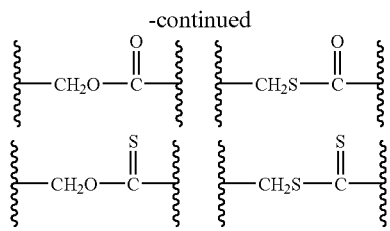

or the group:

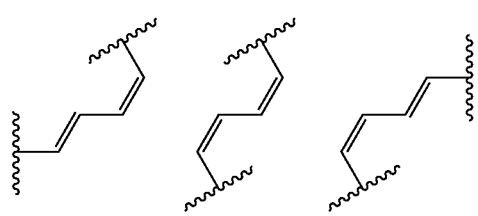

wherein n is 0 or an integer from 1 to 10 and m is 0 or 1;
wherein $R^4$ can be a substituent selected from the group consisting of

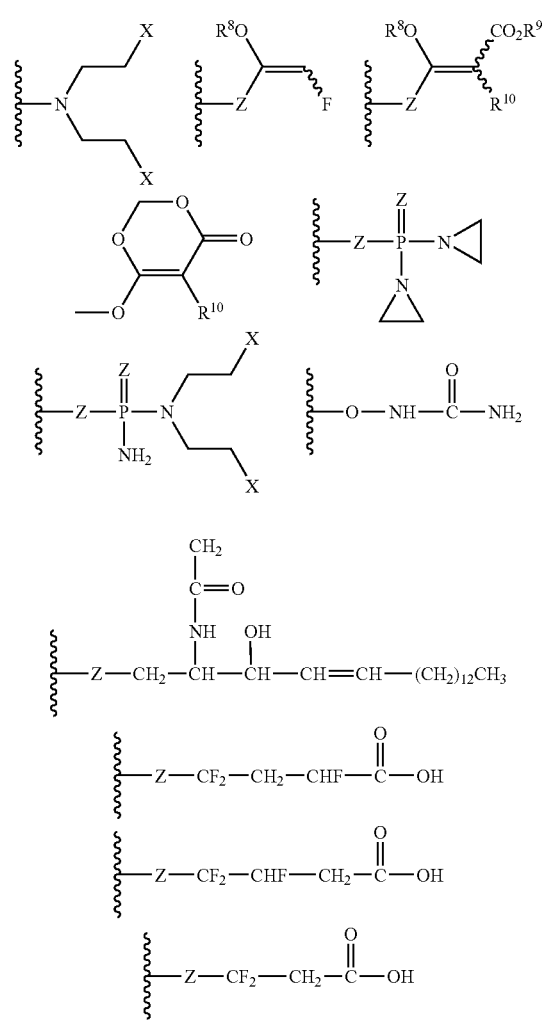

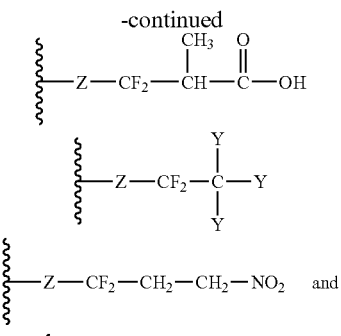

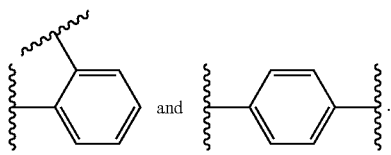

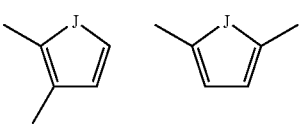

wherein $R^8$ and $R^9$ are lower alkyls and $R^{10}$ is H or $CH_3$ and each X substituent is independently the same or different from the other and is —Cl, —Br, —I, or other potent leaving group, with the proviso that when $R^7$ is —H, and m is zero, then $R^4$ is not a halogen or when m is zero and n is zero, then $R^4$ is not a halogen;

wherein each Y substituent is independently the same or different from the other and is independently —H or —F and each Z substituent is independently the same or different from the other and is —O— or —S—.

In one aspect, m is 0 and $R^2$ is an aromatic hydrocarbyl group selected from the group consisting of:

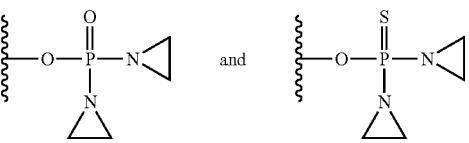

In an alternative aspect, m is 0 and $R^2$ is a heteroaromatic group selected from the group consisting of:

wherein J is selected from the group consisting of —O—, —S—, —Se—, —NH—, and —NR$^{ALK}$— and wherein R$^{ALK}$ is a linear or branched alkyl having 1 to 10 carbon atoms or a cycloalkyl group having 3 to 10 carbon atoms.

In one specific aspect, $R^4$ is selected from the group consisting of:

Q is a selected from the group consisting of a sugar, a carbocylic, an acyclic compound and masked phosphate or phosphoramidate derivatives thereof The masked phosphate or phosphoramidate derivation is attached to Q at the 5′ position of the compound, shown in more detail below. For example, Q is a moiety selected from the group consisting of:

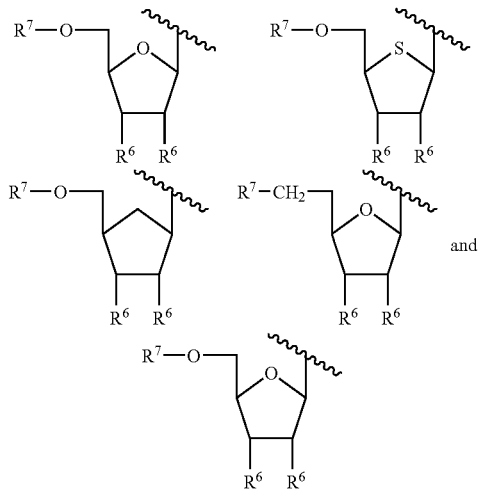

wherein each $R^6$ is independently the same or different from the other and is selected from the group consisting of —H, —OH, —OC(=O)CH$_3$, F, and other protected hydroxyl group; and, $R^7$ is hydrogen, a phosphate group, a phosphodiester group, or a phosphoramidate group attached to Q at the 5′ position.

It should be understood, although not explicitly stated that any of the prodrugs of this invention may be in any enantiomeric, diasteriomeric, or stereoisomeric form, including, D-form, L-form, α-anomeric form, and β-anomeric form.

In one embodiment, $R^4$ is or contains a chemical entity selected from the group consisting of —Br, —I, —O-alkyl, —O-aryl, O-heteroaryl, —S-alkyl, —S-aryl, —S-heteroaryl, —CN, —OCN, —SCN, —NH$_2$, —NH-alkyl, —N(alkyl)$_2$, —NHCHO, —NHOH, —NHO-alkyl, NH$_2$CONHO—, NHNH$_2$, —N$_3$, and a derivative of cis-platin, such as:

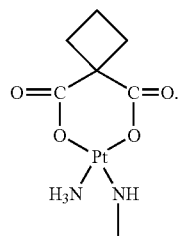

In one embodiment, Q is:

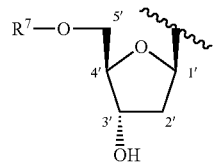

wherein $R^7$ is as described above, or more specifically, a structure such as:

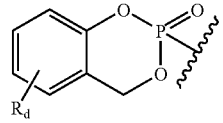

or a compound having the structure:

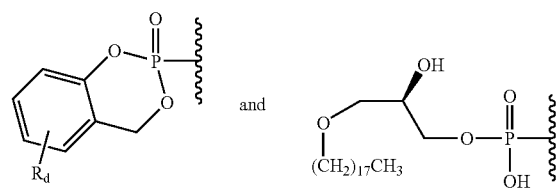

wherein $R_d$ is an aromatic substituent.

In an alternative embodiment, $R^7$ is a phosphoramidate group derived from an amino acid, including, for example, the twenty naturally occurring amino acids. In one embodiment, $R^7$ is a phosphoramidate group derived from alanine. In one embodiment, $R^7$ is or contains a group having the structure:

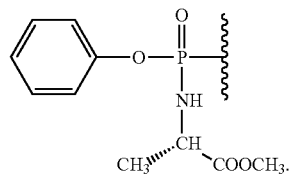

The above group, and methods for its preparation, are described in McGuigan, et al. (1993), and McGuigan, et al. (1996).

This invention also provides an L- or D-isomer of the compound having the structure:

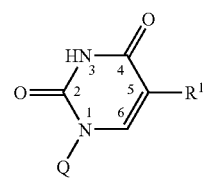

or tautomers thereof,
wherein $R^1$ is a substitutent having the formula:

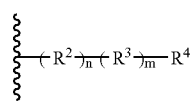

wherein $R^2$ and $R^3$ are the same or different and are independently an unsaturated or a saturated hydrocarbyl group; wherein $R^4$ is selected from the group consisting of F, Cl, Br, I, CN, SO$_3$H, CO$_2$H, CO$_2$CH$_2$CH$_3$, SI(CH$_3$)$_3$, CHO, NO$_2$, CF$_3$, CCl$_3$, C(R$^5$)$_2$; wherein $R^5$ is selected from the group consisting of F, Cl, Br, and I; wherein n is 0 or an integer from 1 to 10 and m is 0 or 1; and Q is as defined above.

In one aspect, m is 0 and $R^2$ is selected from the group consisting of:

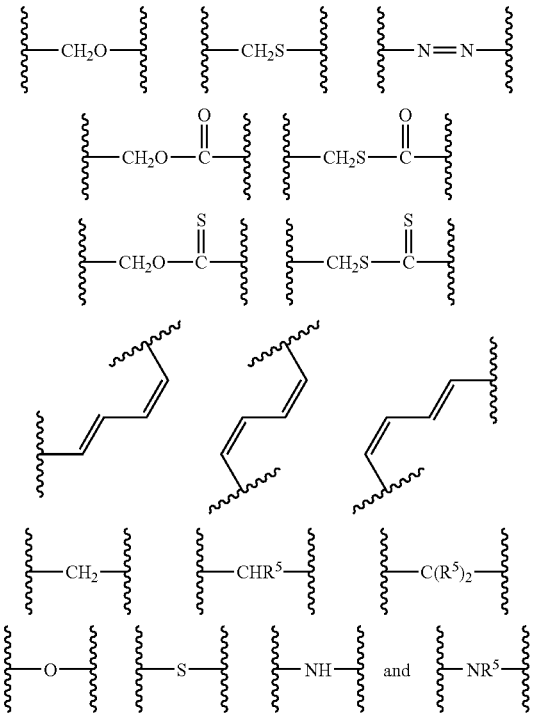

wherein $R^5$ is independently the same or different and is selected from the group consisting of a linear or branched alkyl group having from 1 to 10 carbon atoms, a cycloalkyl group having from 3 to 10 carbon atoms, CN and a halogen.

In another aspect, $R^2$ and $R^3$ taken together is an alkenyl or alkynyl and is selected from the group consisting of:

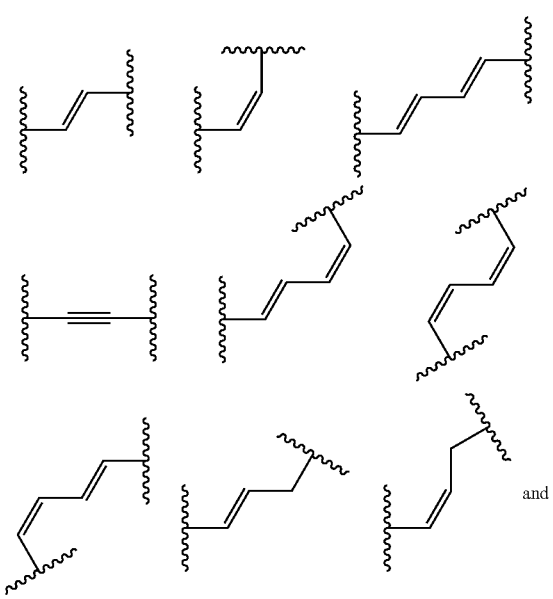

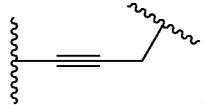

In another aspect, m is 0 and $R^2$ is an aromatic hydrocarbyl group selected from the group consisting of:

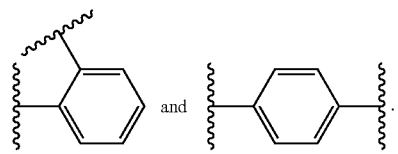

In a further aspect, m is 0 and $R^2$ is a heteroaromatic group selected from the group consisting of:

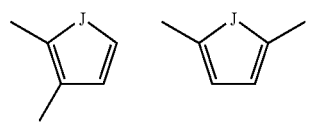

wherein J is selected from the group consisting of —O—, —S—, —Se—, —NH—, and —NR$^{ALK}$— and wherein R$^{ALK}$ is a linear or branched alkyl having 1 to 10 carbon atoms or a cycloalkyl group having 3 to 10 carbon atoms.

For these embodiment, $R^7$ is as described above.

In a specific embodiment, $R^7$ is:

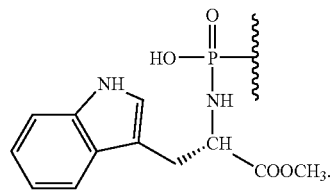

The above group, and methods for its preparation, are described in Abraham, et al. (1996).

In one embodiment, $R^7$ is a phosphate group or is or contains a group having a structure selected from the group consisting of:

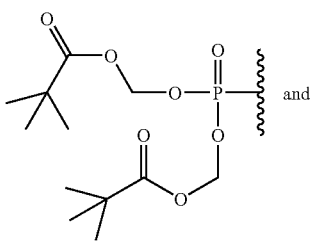

-continued

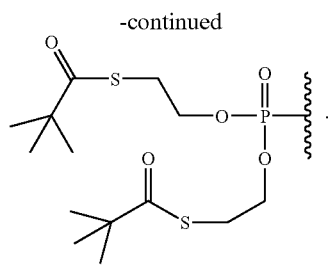

The first of the two above groups, and methods for its preparation, are described in Freed, et al. (1989); Sastry, et al., (1992); Farquhar, et al. (1994), and Farquhar, et al. (1995). The second of the two above groups, and methods for its preparation, are described in Valette, et al. (1996); and Benzaria, et al. (1996).

In one embodiment, $R^7$ is or contains a group having a structure selected from the group consisting of:

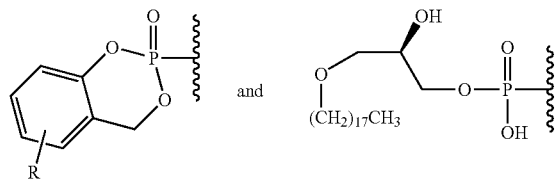

where R is an aromatic substituent the first of the two above groups, and methods for its preparation, are described in Meier, et al. (1997). The second of the two above groups, and methods for its preparation, are described in Hostetler, et al. (1997); and Hostetler, et al., published International Patent Application No. WO 96/40088 (1996).

In one embodiment, the $R^7$ forms a cyclic group within Q. One such embodiment, and a method for its preparation, is shown below (where DMTr is 4,4'-dimethoxytrityl, Boc is t-butyloxycarbonyl, DCC is 1,3-dicyclohexylcarbodiimide, and 4-DMAP is 4-dimethylaminopyridine):

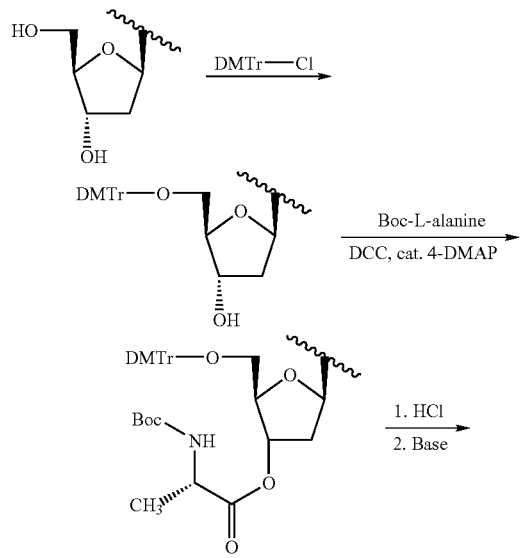

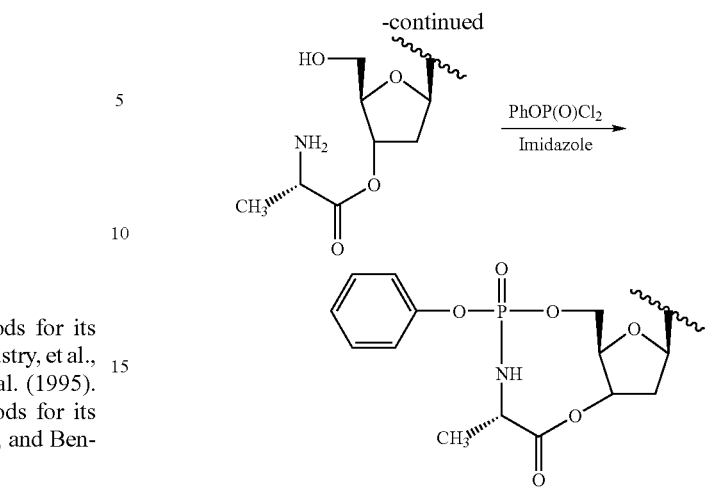

In one embodiment, the compound may be in a salt form, or in a protected or prodrug form, or a combination thereof, for example, as a salt, an ether, or an ester.

In a separate embodiment, the above structures are further modified to possess thiophosphodiaziridine instead of phosphodiaziridine groups, using the methods described below.

Synthesis of the above noted 5-substituted pyrimidine derivatives can be accomplished by methods that are well-known in the art. For example, treatment of 5-chloromercuri-2'-deoxyuridine with haloalkyl compounds, haloacetates or haloalkenes in the presence of $Li_2PdCl_4$ results in the formation, through an organopalladium intermediate, of the 5-alkyl, 5-acetyl or 5-alkene derivative, respectively. Wataya, et al. (1979) and Bergstrom, et al. (1981). Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of $Li_2PdCl_4$. Bigge, et al. (1980).

Pyrimidine deoxyribonucleoside triphosphates were derivatized with mercury at the 5 position of the pyrimidine ring by treatment with mercuric acetate in acetate buffer at 50° for 3 hours. Dale, et al. (1973). Such treatment also would be expected to be effective for modification of monophosphates; alternatively, a modified triphosphate could be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines, see for example, U.S. Pat. Nos. 4,247,544; 4,267,171; and 4,948,882; and Bergstrom, et al. (1981). The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of a 5-position substituent is the halovinyl group, e.g. E-5-(2-bromovinyl)-2'-deoxyuridylate. Barr, P. J. et al. (1983).

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, though the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

The structures at the 5-position of uracil are referred to as the tethers because they connect the proposed leaving group (toxophore) to the heterocycle. Upon activation of the heterocycle by reaction with the Cys residue in the active site of a human enz, TS, for example, a negative charge is conducted from the 6-position of uracil into the tether. This mechanism has been described for the 5'-monophosphorylated versions of (E)-5-(bromovinyl)-2'-deoxyuridine (BVdU) by Barr, P. J. et al. (1983) and of (E)-5-(3,3,3-trifluoro-1-propenyl)-2'-deoxyuridine (TFPe-dUrd) by Wataya, et al. (1979), Santi (1980); and Bergstrom, et al. (1984).

The tether "spacer" between the toxin and dNMP must be unsaturated so that it can conduct the toxin-labilizing negative charge supplied by the TS-Cys-sulfhydryl attack. Of the many unsaturated organic functionalities available for this purpose, the vinyl, allyl, and propargyl units are simple, small, and readily accessible synthetically. The vinyl and allyl units have the advantage that they can be prepared in either of two non-interconvertible geometric isomeric forms. Thus, they can be used as "probes" of prodrug accommodation by the enzyme active site. On the other hand, the propargyl unit has the advantage of being cylindrically symmetrical, so that enz-catalyzed toxin release from this type of tether does not depend upon its orientation with respect to dUMP's uracil ring, as is the case with the vinyl and allyl molecules.

Two distinct approaches have been taken to design of some of the nucleotide-based prodrugs of this invention. One is based on the structure of BVdU monophosphate and features a leaving group/toxin directly attached to the terminus of a (poly)vinyl substituent at C5 of dUMP. This is the vinyl tether approach. The other is based on the structure of TFPe-dUMP and is similar to the first but has a methylene unit separating the leaving group/toxin and the unsaturated unit and thus contains an allyl or propargyl unit. This is the allyl tether approach.

The mechanism of activation of a propargyl version of the allyl tether approach has a precedent in the interaction of both 5-ethynyl-2'-deoxyuridine 5'-monophosphate (EdUMP) and 5-(3-hydroxy-1-propynyl)-2'-deoxyuridine 5'-monophosphate (HOPdUMP) with TS (Barr, et al. (1981); Barr and Robins 1983). EdUMP is a potent inhibitor of TS (Ki=0.1 TM), and likely forms an allene-based species at the active site. HOPdUMP (Ki=3.0 TM) shows unusual inhibition kinetics, which might be due to formation of a cumulene-based species at the active site.

5-Alkylidenated 5,6-dihydrouracils similar in structure to the intermediate common to both the vinyl and allyl tether approach mechanisms have been synthesized recently (Anglada et al. 1996). These were shown to be highly electrophilic. Their ready reaction with ethanol to generate 5-(ethoxymethyl)uracil is a precedent for the water addition that regenerates catalytically competent TS. Even more recently, the existence of the long-elusive C5 methylene intermediate produced by TS was demonstrated by trapping studies (Barrett, et al. (1998)).

Particular embodiments include the compounds having the L or D structures shown below. Compounds are identified by structure and a numerical designation.

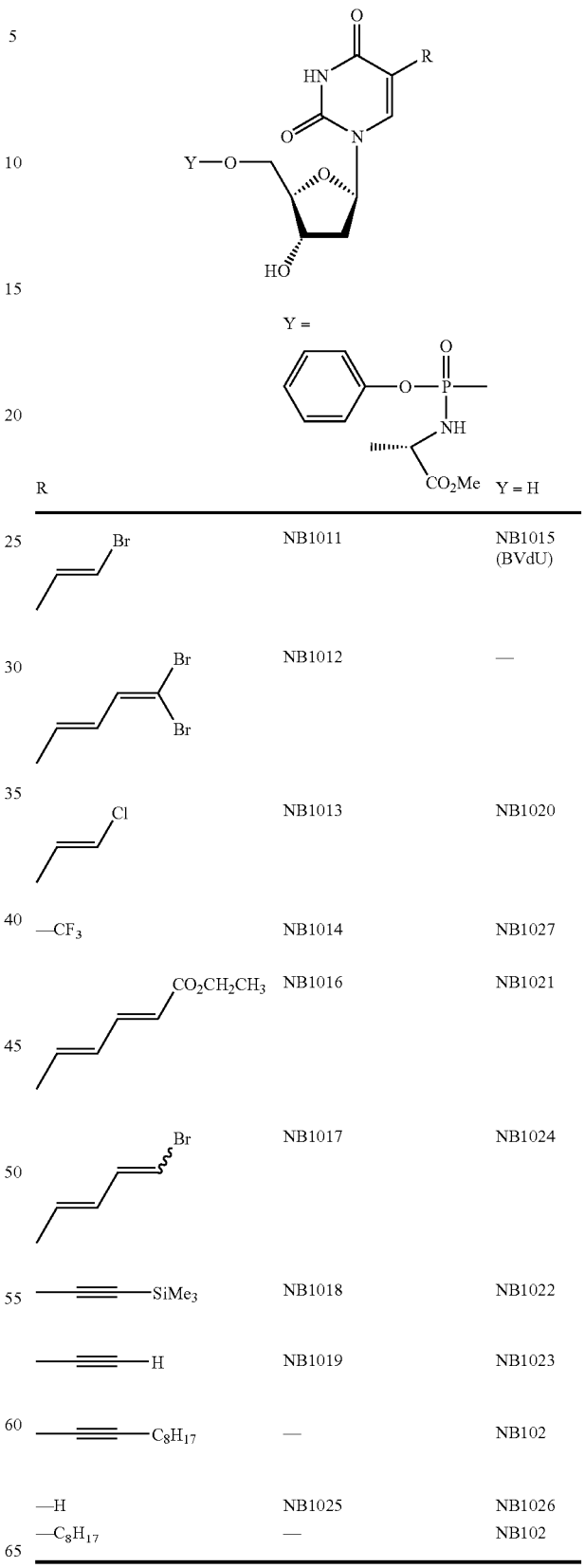

| R | | Y = (phenyl phosphoramidate) | Y = H |
|---|---|---|---|
| Br (vinyl) | | NB1011 | NB1015 (BVdU) |
| Br,Br (dibromo vinyl) | | NB1012 | — |
| Cl (vinyl) | | NB1013 | NB1020 |
| —CF$_3$ | | NB1014 | NB1027 |
| CO$_2$CH$_2$CH$_3$ (vinyl) | | NB1016 | NB1021 |
| Br (allyl) | | NB1017 | NB1024 |
| ≡—SiMe$_3$ | | NB1018 | NB1022 |
| ≡—H | | NB1019 | NB1023 |
| ≡—C$_8$H$_{17}$ | | — | NB102 |
| —H | | NB1025 | NB1026 |
| —C$_8$H$_{17}$ | | — | NB102 |

Preferred embodiments are shown below:
A compound having the structure:

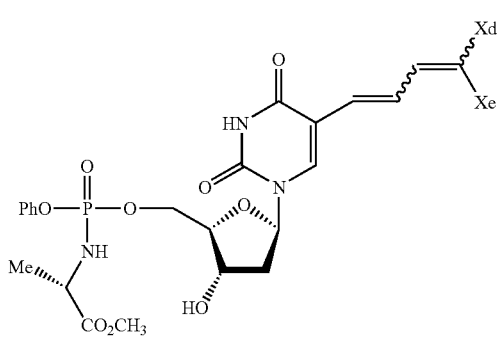

wherein $X_d$ and $X_e$, are independently the same or different and are selected from the group consisting of Cl, Br, I, and CN or the nucleoside analogs thereof. In a more preferred aspect, $X_d$ is Cl or Br and $X_e$ is H.

A compound having the structure:

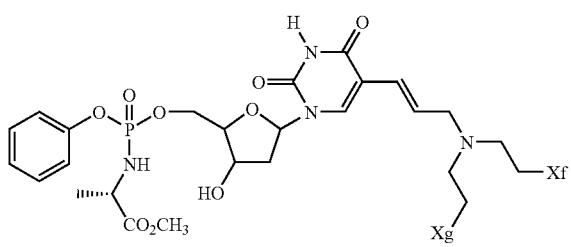

wherein $X_f$ and $X_g$ are independently the same or different and are selected from the group consisting of Cl, Br, I, and CN or the nucleoside analogs thereof. In a preferred embodiment, $X_f$ and $X_g$ are the same and are each is Cl or Br.

A compound having the structure of the formula:

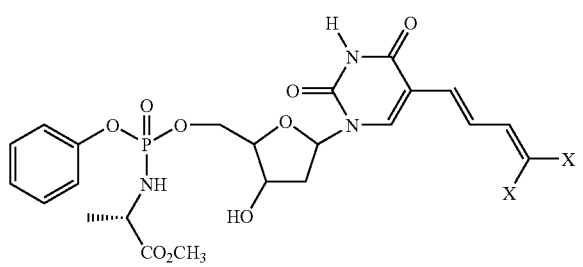

wherein each X is selected from the group consisting of Cl, Br, I, and CN;
or the nucleoside analogs thereof In a preferred embodiment, X is Cl or Br and in a more preferred embodiment, X is Br.

A compound having the structure:

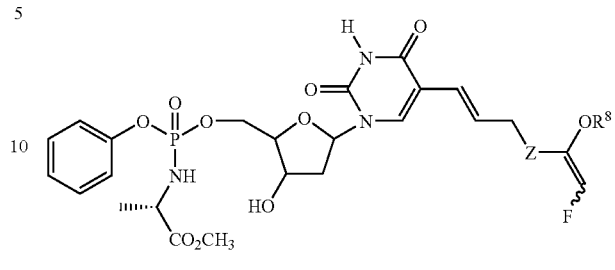

wherein $R^8$ is a lower straight or branched chain alkyl, or the nucleoside analogs thereof.

A compound having the structure:

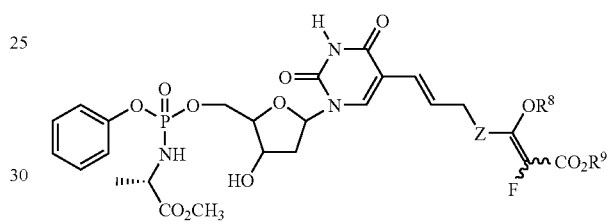

wherein $R^8$ and $R^9$ are lower straight or branched chain alkyls and $R^{10}$ is H or $CH_3$ or the nucleoside analogs thereof.

A compound having the structure:

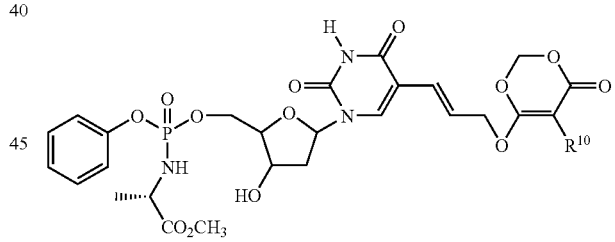

wherein $R^{10}$ is H or $CH_3$; or the nucleoside analog thereof.

A compound having the structure:

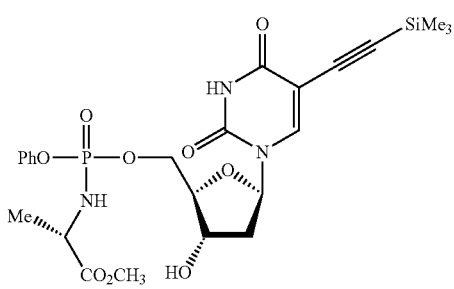

A compound having the struture:

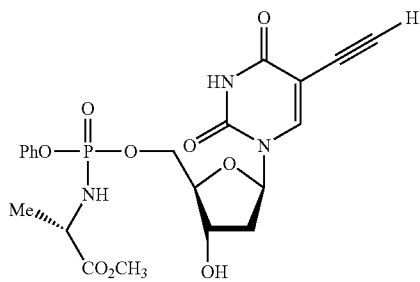

or the nucleoside analog thereof.

A compound as described herein, wherein the compound has the structure:

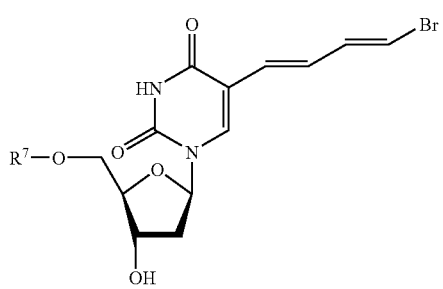

In one aspect, $R^7$=H. In another aspect, $R^7$ is a substituent having the structure:

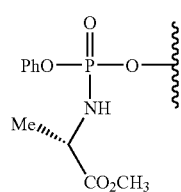

A compound as described herein wherein the compound has the structure:

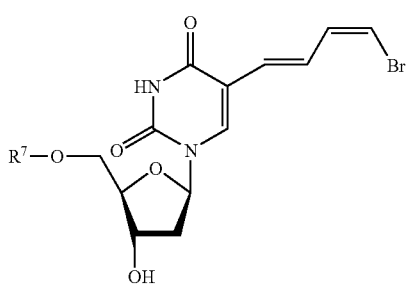

wherein $R^7$=H or $R^7$ is a substituent having the structure

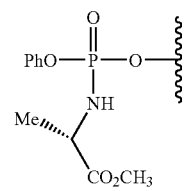

A compound having the structure:

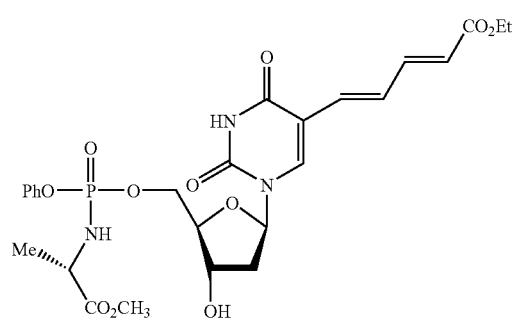

A compound having the structure:

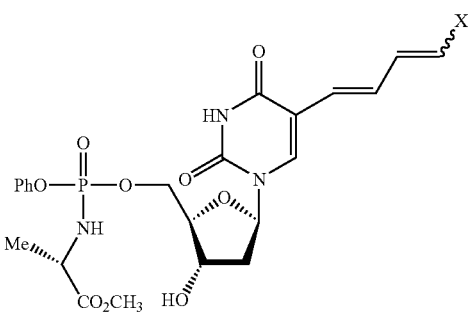

wherein each X is selected from the group consisting of $CO_2Et$, Cl, and Br, or the nucleoside analog thereof.

A compound having the structure:

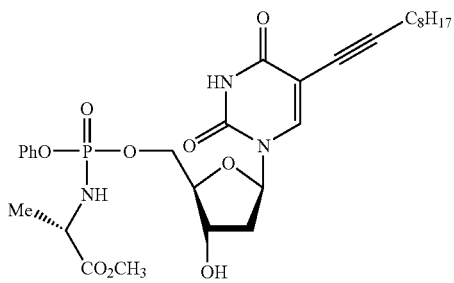

or the nucleoside analog thereof

A compound having the structure:

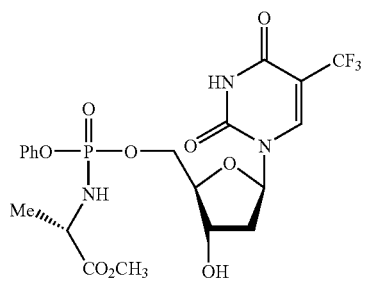

or the nucleoside analog thereof.

The prodrugs can be combined with a carrier, such as a pharmaceutically acceptable carrier, for use in vitro and in vivo.

Figure 2A:
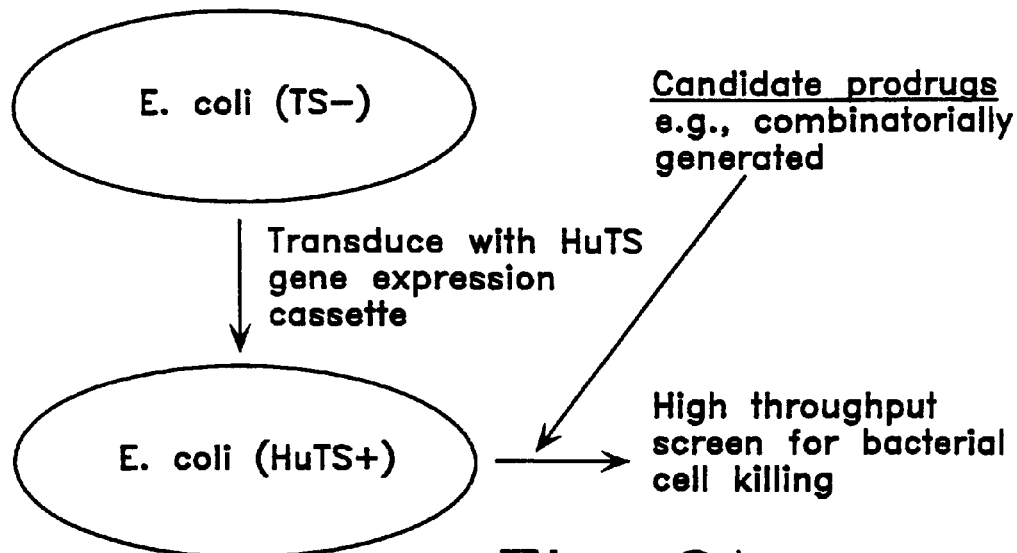
FIGS. 2A and 2B are flow charts illustrating a high throughput screen of this invention.
Figure 2B:
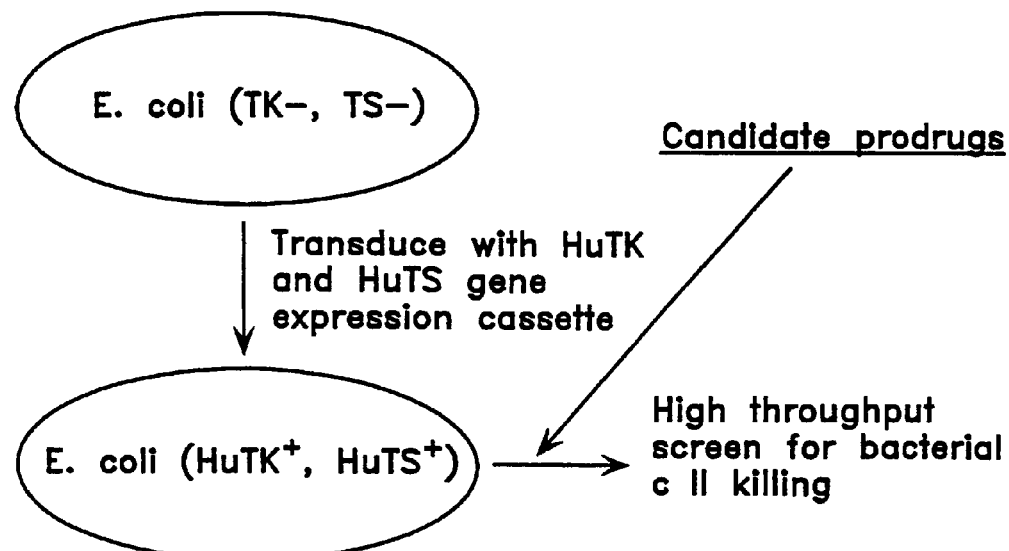

This invention also provides a quick and simple screening assay that will enable initial identification of novel compounds with at least some of the desired characteristics (see FIGS. 2A and 2B). The assay requires at least two cell types, the first being a control cell in which the target enzyme is not expressed or is expressed at a low level, e.g., a normal cell. The second cell type is the test cell in which the target enzyme is expressed at a detectable level, e.g., a high level. This cell can be a tumor cell line that is selected for enhanced levels of target enzymes. Alternatively, a cell genetically modified to differentially express the target enzyme or enzymes (containing the appropriate species of target enzyme) can be used. Transfection of host cells with polynucleotides encoding the target enzyme is either transient or permanent using procedures well known in the art and described in Chen, L. et al. (1996); Hudziak, R. M. et al. (1988); or Carter, P. et al. (1992), and in the experimental section below. The cells can be procaryotic (bacterial such as E. coli) or eucaryotic. The cells can be mammalian or non-mammalian cells, e.g., mouse cells, rat cells, human cells, fungi (e.g., yeast) or parasites (e.g., Pneumocystis or Leishmania) which cause disease.

Suitable vectors for insertion of the cDNA are commercially available from Stratagene, La Jolla, Calif. and other vendors. The amount of expression can be regulated by the number of copies of the expression cassette introduced into the cell or by varying promoter usage. The level of expression of enzyme in each transfected cell line can be monitored by immunoblot and enzyme assay in cell lysates, using monoclonal or polyclonal antibody previously raised against the enzyme for immuno-detection. (Chen, L. et al. (1996)). Enzymatic assays to detect the amount of expressed enzyme also can be performed as reviewed by Carreras, C. W. and Santi, D. V. (1995), or the method described in the experimental section below.

In a further aspect, more than one species of enzyme can be used to separately transduce separate host cells, so that the effect of the candidate drug on a target enzyme can be simultaneously compared to its effect on another enzyme or a corresponding enzyme from another species.

In another embodiment, a third target cell is used as a control because it receives an effective amount of a prodrug compound of this invention. This embodiment is particularly useful to screen for new agents that are activated by thymidylate synthase. In yet a further aspect, at least one additional test cell system is set up to test the synergistic potential of the test therapeutic in combination with a known therapy or agent.

For the purposes of this invention, the successful candidate drug will block the growth or kill the test cell type, but leave the control cell type unharmed. Growth assays can be performed by standard methods as described by Miller (1992); Sugarman, B. J. et al. (1985) and Spector, D. L. et al. (1998), or using the methods described in the experimental section below.

It will be understood by those skilled in the art that the screen can be applied broadly for the discovery of antibiotics. For example, thymidylate synthase from yeast could be substituted for that of human or E. coli forms of the enzyme. This would allow the discovery of specific antifungal antibiotics targeting yeast related pathogens. In addition, other enzymes can be subjected to this treatment. For example, prodrugs that target specifically the dihydrofolate reductase activity of infectious agents, like Pneumocystis carnii, could be selected. These agents will be selected for specificity for the target enzyme, and can be shown not to activate the enzyme of the natural host by employing the screening assay described herein. The control cellular constructs would contain the corresponding normal human enzyme, in order to show lack of toxicity when only the normal human enzyme is present.

FIGS. 2A and 2B show how one may conduct at least one embodiment of this aspect of the invention. A foreign gene, e.g., a human gene encoding TS, is inserted into the host cell such that human TS is expressed. The "control cell" does not express the target enzyme. In some embodiments it may be necessary to supplement the culture media with the protein product of the target enzyme.

The candidate prodrug can be directly added to the cell culture media and the target cell or the culture media is then assayed for the amount of label released from the candidate prodrug if the prodrug contains a detectable label. Alternatively, cellular uptake may be enhanced by packaging the prodrug into liposomes using the method described in Lasic, D. D. (1996) or combined with cytofectins as described in Lewis, J. G. et al. (1996).

An alternative embodiment for a prodrug taking advantage of TS overexpression in tumor cells is a deoxyuridine phosphoramidate, or other modifications (cited herein) conjugated with a therapeutic radionuclide. An example of a therapeutic radionuclide is rhenium 188. The isotope can be synthesized essentially as described by Callahan, et al. (1989). Alternatively, it can be obtained commercially, for example from Mallicrodt Medical BV, The Netherlands. The therapeutic radionuclide can be conjugated with deoxyuridine, or deoxyuridine 5'-phosphoramidate, or other derivative, by standard methods for example, as described by Lin, W. Y. et al. (1997). The radionuclide-containing deoxyuridine phosphoramidate will be preferentially taken up into the DNA of tumor cells overexpressing thymidylate synthase and cause their death via concentrated emission of beta and gamma radiation. Alternative radionuclides include rhenium-186, and others. (Troutner, D. A. (1987)).

The compounds are useful to predict whether a subject will be suitably treated by a prodrug of this invention by delivering to a sample containing the cell to be treated a prodrug and assaying for cell death or inhibition of cell proliferation. Applicants provide kits for determining whether a pathological cell or a patient will be suitably treated by this therapy by providing at least one prodrug of this invention and instructions for use.

This invention also provides a method for inhibiting the proliferation of a pathological or target cell in vitro or in vivo by delivering to the cell an effective amount of a prodrug of this invention. When practiced in vivo, the method is useful to treat a pathology characterized by target cells in a subject by delivering to the subject an effective amount of a prodrug of this invention.

When the target cell is target cell is resistant to a chemotherapeutic drug, the method can be further modified by contacting or administering to the cell or patient an effective amount of the drug to which the cell has developed resistance. Because the prodrugs of this invention can reverse resistance to the prior therapy, subsequent to successful treatment with a prodrug of this invention, administration of the previous therapy can again inhibit growth or metastasis of tumors. Examples where this may occur include, but are not limited to when the target cell expresses an enzyme that is amplified as a result of selection in vivo by chemotherapy or when the target enzyme is an endogenous intracellular enzyme that is overexpressed in the target cell. An example of such an enzyme is thymidylate synthase which has been shown to be overexpressed as a result of prior chemotherapy and confers a drug resistant phenotype on the cell to the prior drug.

The prodrugs of this invention can also be combined with other known therapies to enhance or synergize the therapeutic effects of either or both prior therapies or the therapeutic effect of the prodrug. Such prior therapies include, but are not limited to cancer chemotherapy, radiation therapy and surgery.

When delivered to an animal, the method also is useful to further confirm efficacy of the prodrug. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the prodrug is administered, for example, by intraperitoneal or intravenous routes. Tumor measurements to determine reduction of tumor size are made in two dimensions using venier calipers twice a week. Other animal models may also be employed as appropriate. (Lovejoy et al. (1997); Clarke, R. (1996); and Pegram, M. D. et al. (1997)).

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The prodrug, combinations of drugs, or compositions containing either can be used in the manufacture for medicaments for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

In general, a suitable dose for each of the above-named compounds, is in the range of about 1 to about 100 mg per kilogram body weight of the recipient per day, preferably in the range of about 1 to about 50 mg per kilogram body weight per day and most preferably in the range of about 1 to about 25 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 1 to about 100 mg, preferably about 1 to above about 25 mg, and most preferably about 5 to above about 25 mg of active ingredient per unit dosage form. It will be appreciated that appropriate dosages of the compounds and compositions of the invention may depend on the type and severity and stage of the disease and can vary from patient to patient. Determining the optimal dosage will generally involve the balancing of the level of therapeutic benefit against any risk or deleterious side effects of the treatments of the present invention.

Ideally, the prodrug should be administered to achieve peak concentrations of the active compound at sites of disease. This may be achieved, for example, by the intravenous injection of the prodrug, optionally in saline, or orally administered, for example, as a tablet, capsule or syrup containing the active ingredient. Desirable blood levels of the prodrug may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the prodrug ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the prodrug may be employed with either a paraffinic or a water-miscible ointment base. Alternatively, the prodrug ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the prodrug ingredient through the skin or other affected areas. Examples of such dermal penetration enhancers include dimethylsulfoxide and related analogues.

The oily phase of the emulsions of this invention may be constituted from known ingredients in a known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the prodrug ingredient. The prodrug ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as suppositories, tampons, creams, gels, pastes, foams or spray formulations containing in addition to the prodrug ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or ore organs. The formulations may be presented in unit-dose or multi-dose sealed containers, for example, ampoules and vials, and may be stored in a freeze-dried lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable of oral administration may include such farther agents as sweeteners, thickeners and flavoring agents.

Prodrugs and compositions of the formula of the present invention may also be presented for the use in the form of veterinary formulations, which may be prepared by methods that are conventional in the art.

The following examples are intended to illustrate, but not limit the invention.

Materials and Methods

Synthesis of Nucleoside ECTA Compounds

Synthesis of the above noted 5-substituted pyrimidine nucleosides can be accomplished by methods that are well-known in the art and briefly described above.

In one embodiment the present invention involves four classes of compounds. Each class is defined by the structure of the uracil base, or modified uracil base present. These classes are ECTA compounds where: 1) the base is a furano-pyrimidinone derivative of uracil; 2) the base is 6-fluorouracil; 3) the base is 4-hydrazone substituted uracil derivative; 4) the base is uracil. The uracil or modified uracil derived base is used to synthesize compounds substituted with toxic leaving groups at the 5 position, attached by an electron conduit tether at this 5 position, and including an appropriate spacer moiety between the electron conduit and the toxic leaving group. The ECTA compounds can be unphosphorylated, 5' monophosphate, 5' phosphodiester, or 5' protected ("masked") deoxyuridines or comparable derivatives of alternative carbohydrate moieties, as described below. Protected 5-substituted deoxyunridine monophosphate derivatives are those in which the phosphate moiety has been blocked through the attachment of suitable chemical protecting groups. Protection of 5-substituted deoxyuridine monophosphate derivatives can improve solubility, facilitate cellular penetration, facilitate passage across the blood-brain barrier, and prevent action of cellular or extracellular phosphatases, which might otherwise result in loss of the phosphate group. In another embodiment, 5-substituted uracil or uridine derivatives are administered to cells containing nucleoside kinase activity, wherein the 5-substituted uracil/uridine derivative is converted to a 5-substituted uridine monophosphate derivative. Uridine derivatives may also be modified to increase their solubility, cell penetration, and/or ability to cross the blood-brain barrier.

Action of thymidylate synthase upon 5-substituted uridine monophosphate derivatives can release the substituent attached to the 5-position ("leaving group") of the pyrimidine ring. The released substituent is then capable, either inherently or following reaction with another cellular component, of acting as a toxin or an inhibitor of cellular proliferation.

Synthesis of ECTA Compounds with Propargyl Tethers

The synthesis of propargylic and allylic alcohol-equipped 2'-deoxyuridines is straightforward. Many of these and their close derivatives are reported in the literature, and some have even been studied in connection with TS. For example, 5-alkynyl-dUMPs including the 5-(3-methoxy-1-propynyl) and 5-(3-hydroxy-1-propynyl) ones have been examined as TS inhibitors (Barr, and Robins (1981)) and some of these have been shown to become incorporated into the DNA of TS-deficient cancer cells (Balzarini, J. et al. (1985)).

Both 5-mercuri-(Ruth, J. L. et al. (1978)) and 5-iodouridines (Robins, M. J. et al. (1981)) readily condense with alkenes and alkynes in the presence of a palladium catalyst to afford C5 tether-equipped uridines. The latter route is the more often employed (Robins, M. J. et al. (1982)), Asakura, J. et al. (1988) and (1990)). High-yielding condensations of protected 5-iodo-2'-deoxyuridines with t-butyidimethylsilyl propargyl ether (Graham, et al. (1998); De Clercq, et al. (1983), methyl propargyl ether (Tolstikov, et al. (1997)) and even propargyl alcohol itself (Chaudhuri, et al. (1995) and Goodwin, et al. (1993)) have been achieved. The 3-hydroxy-1-propynyl substituent introduced by the latter reaction can also be accessed by DIBAL-H reduction of a methacrylate group (Cho, Y. M. et al. (1994)), itself arising from the same Heck reaction used in the synthesis of BVdU. These palladium-catalyzed reactions are so versatile that they can used to condense very long and elaborately-functionalized propargyl-based tethers to 5-iodo-2'-deoxyuridines. (Livak, et al. (1992) and Hobbs (1989)). (Z)-Allyl-based tethers are generated by the partial hydrogenation of a propargylic precursor over Undiar catalyst (Robins, M. J. et al. (1983)) whereas the (E)-allyl-based ones are best prepared by Heck coupling of an (E)-tributylstannylated ethylene (Crisp, (1989)).

Closely following the literature procedures, a t-butyldimethylsilyl propargyl ether-equipped 3',5'-di-O-protected 2'-deoxyuridine (Graham, et al. (1998), and De Clercq, et al. (1983)) is prepared and a portion of it, converted to the corresponding (Z)-allyl ether, (Robins and Barr (1983)) is reduced. Because the TBAF-mediated removal of a TBDMS group generates an oxyanion that can be functionalized in situ, these TBDMS-protected propargyl- and (Z)-allytic-tethered nucleosides will serve as convenient precursors to some of the toxophore-equipped targets. For the (E)-allyl alcohol equipped nucleoside, the known O-tetrahydropyranyl ether derivative is prepared by the literature Heck coupling of an (E)-tributylstannylated ethylene (Crisp (1989)).

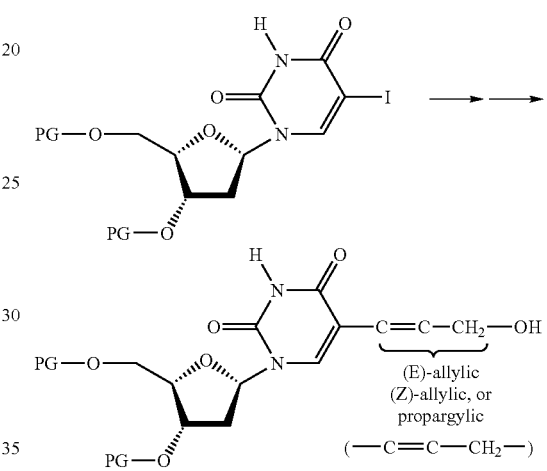

Using a two step literature protocol (Phelps et al. (1980) and Hsiao and Bardos (1981)), the propargylic and (E) and (Z)-allylic alcohols are converted to their corresponding bis-aziridinyl phosphoramidates or thiophosphoramidates so that TS processing of the 5'-mononucleotide versions will release an active metabolite of the cytostatic drugs TEPA or ThioTEPA (Dirven, et al. (1995)), respectively.

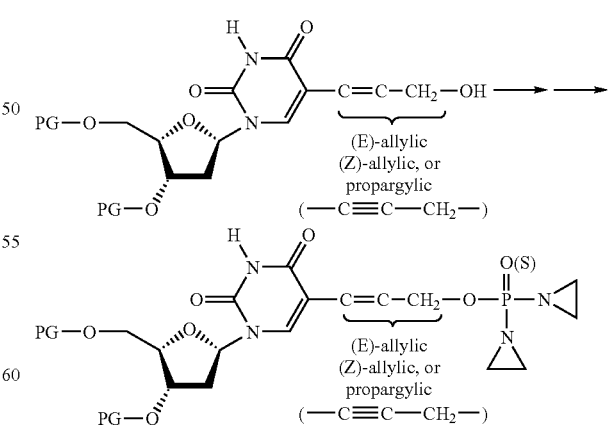

Synthesis of Furano-pyrimidinones

Synthesis of furano-pyrimidinones begins with synthesis of a C5 propargylic-alcohol-equipped 2'-deoxyuridine.

Furano-pyrimidinone compounds are then be formed from the O-tetrahydropyranyl ether derivative described above. Synthesis proceeds by reaction of the second carbon of the propargyl bond with the oxygen attached to the C4 position of the pyrimidine ring to yield a fluorescent furano-pyrimidinone which can be readily separated from the reaction mix. Such compounds provide an additional basis for synthesis of ECTA compounds through various combinations of specific electron conduits, spacers and toxic leaving groups.

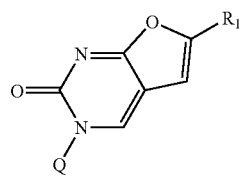

Figure 4:
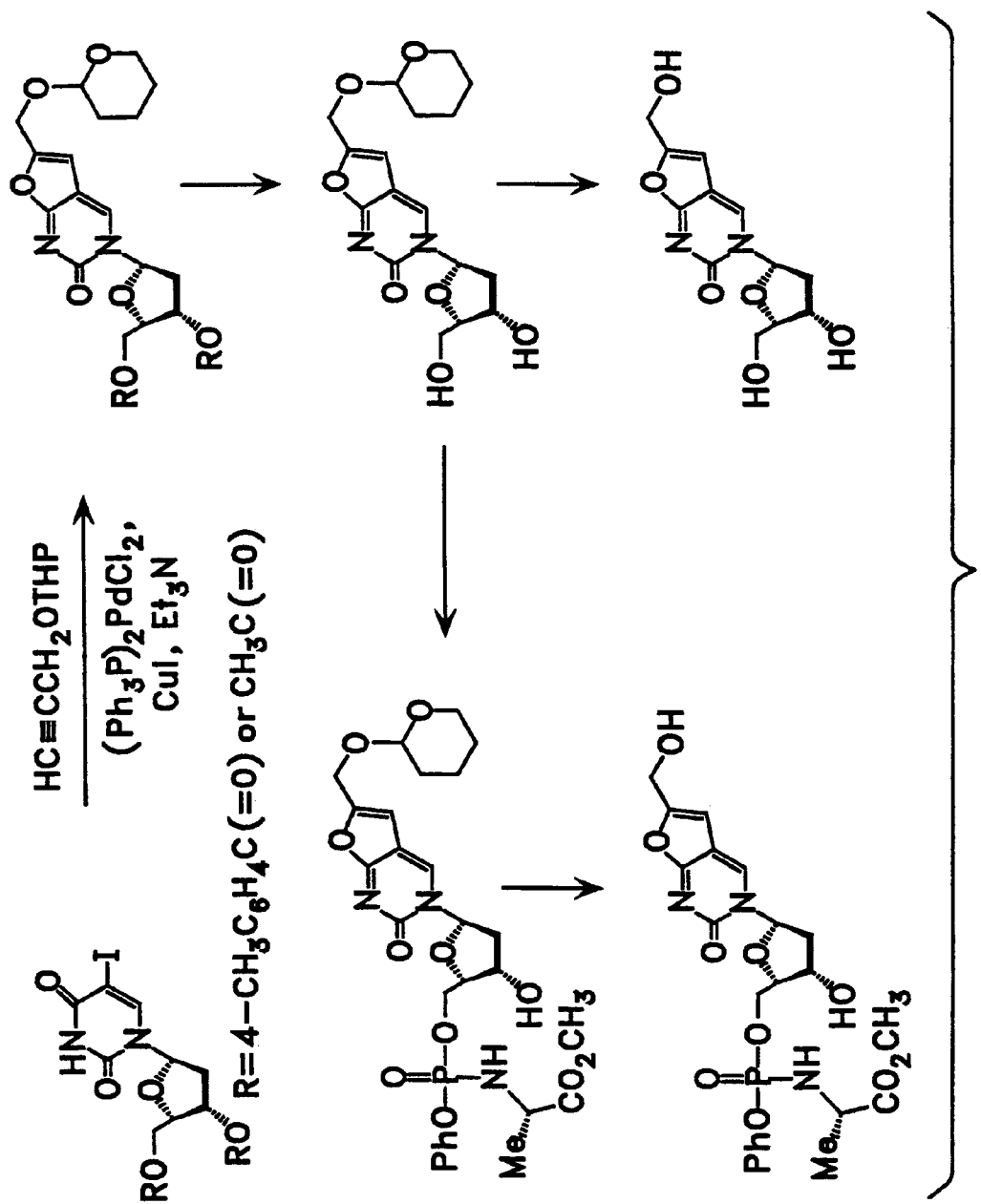
FIG. 4 shows the synthetic scheme for the furo[2,3-d] pyrimidinone nucleosides of this invention. The synthetic protocol is described in detail, infra.

The furo[2,3-d]pyrimidinone nucleosides were prepared by condensing 2',3'-di-O-p-toluoyl or 2',3'-di-O-acetyl-5-iodo-2'-deoxyuridine with 1-(tetrahydropyranyloxy)-2-propyne ("New methods of synthesis of δ-aminoethylpyrazoles" Jones, R. G. and Mann, M. J. (1953)) under conditions known to promote the formation of these fluorescent compounds (Robins, M. J. et al. (1983)). Base-catalyzed removal of the carbohydrate protecting groups gave the 6-(tetrahydropyran-2-yloxymethyl)-substituted bicyclic nucleoside which was either subjected to standard acidic THP group hydrolysis (TFA in $CH_2Cl_2$) or was regioselectively 5'-phosphoramidated by the same procedure used to prepare BVdU-PA and 5FUdR-PA. After the phosphoramidation, the THP group could be removed by acidic hydrolysis, as shown in FIG. 4.

TS ECTA Compounds Based on Furano-Pyrimidinones

Toxic $R^4$ leaving groups can be attached to the furan-2 methyl alcohol using methods similar to those employed to attach toxic leaving groups to the hydroxyl on the C5 propargyl uridine compound, as explained with the synthesis of the TEPA and ThioTEPA derivatives described above. A variety of alternative toxic leaving groups, apparent to one skilled in the art, are envisioned. In addition, modifications to the length and composition of the $R^2$ electron conduit component and of the composition of the $R^3$ spacer element are also envisioned.

TS ECTA compounds based on furano-pyrmidinones can also consist of variously modified "Q" moeities. Many 5-substituted 2'-deoxyuridines are not substrates for human TK, but interestingly 5-(4-hydroxy-1-butynyl)-2'-deoxyuridine was found to be an exception (Barr, P. J. et al. (1981)). The ECTA compounds can have a free 5' hydroxyl, a 5' monophosphate, or a 5' phosphoramidate group attached to alternative carbohydrate groups. A novel method for synthesis of such phosphoramidate compounds is accomplished by reacting a 2-deoxy 3'-hydroxy, 5'-hydroxy unprotected nucleotide with a phosphochloridate in the presence of an HCl scavenger. In a preferred embodiment, the phosphochloridate comprises a phosphorus substituent which is derived from an amino acid such as alanine. For example, the phosphochloridate can be phenyl-L-methoxyalanine phosphorochloridate.

C6 Fluoro Uridine and C4 Hydozone Based Compounds

The neutral thiol addition to the pyrimidine C5-C6 double bond proceeds as an exothermic reaction (3-9 kcal per mol; see review by Les, A. et al. (1998)) in the normal TS reaction with dUMP. Alternative substituents to the TS reactive hydrogen at the 6 position that can facilitate the formation of the sulfhydryl bond with the enzyme, via the active human TS cysteine (homologous with cys-198 of *L. casei*), include fluorine. Such substituents at other positions in the pyrimidine ring can also facilitate the reaction between the substrate and TS. For instance, a 4-hydrazone substitution on the uracil (as described by Les, A. et al. (1998) facilitates formation of the thiol with TS. It is important that the resulting nucleotide-thiol (TS) intermediate rearranges in such a way as to release the altered nucleotide which can be accomplished passively via hydrolysis.

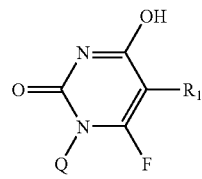

The introduction of fluorine at the C6 position has not been previously reported, but it can be synthesized by following the synthetic descriptions of Krajewskas and Shugar (1982), who describe the synthesis of a number of 6 substituted uracil and uridine analogues.

Chemistry facilitating substitutions at the C4 position of the pyrimidine base are well known by those skilled in the art. Examples of literature descriptions include Wallis et al. (1999); Negishi, et al. (1996), Barbato et al. (1991), Barbato, et al. (1989) and Holy et al. (1999). These synthetic techniques also enable combinations of substitutions, for instance at the C4 and C5 positions of the pyrimidine ring (Pluta, et al. 1999) or the C2 and C4 positions of the pyrimidine ring (Zeid, et al. (1999)).

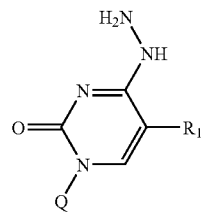

In another embodiment of the invention, ECTA compounds are synthesized by addition of alternative electron conduits, spacer moieties and toxic leaving groups to either the C6 fluoro-uridine base or the C4 hydrazone modified pyrimidine. Methods described above for synthesis of 2, deoxyuridine based ECTA compounds can again be employed for synthesis of such molecules.

Synthesis of Nucleoside Phenyl Methoxyalaninyl Phosphoramidates

The use of phosphoramidates as phosphate prodrugs for nucleotides was first reported by McGuigan, C. et al. (1993) and McGuigan, C. et al. (1994). These authors showed that phosphoramidate derivatives of antiviral 2',3'-dideoxynucleoside derivatives such as d4T retain their antiviral activities in thymidine-kinase deficient cells. Further studies showed that the phosphoramidate group was hydrolyzed to the phosphate group inside cells (McGuigan, C. et al. (1996); Balzarini, J. et al. (1996); and Saboulard, et al. (1999)). The phospharamidates were synthesized by reacting 2',3'-dideoxynucleosides with phenyl methoxyalaninyl phosphorochloridate (PMPC).

Since only one hydroxyl group is present, these reactions usually proceed smoothly. In compounds where more than one hydroxyl group is present, the appropriately protected nucleoside might be required. Since the 5'-OH group of 2'-deoxynucleosides is much less hindered than the 3'-OH group, selective phosphoramidation with PMPC is possible under carefully controlled conditions. Both BVdU and 5FUdR condensed with PMPC in the presence of N-methylimidazole in anhydrous $CH_2Cl_2$ to give the corresponding phosphoramidates. In both cases, the desired product was readily separable from the starting material using column chromatography on silica gel. The synthetic scheme is summarized below.

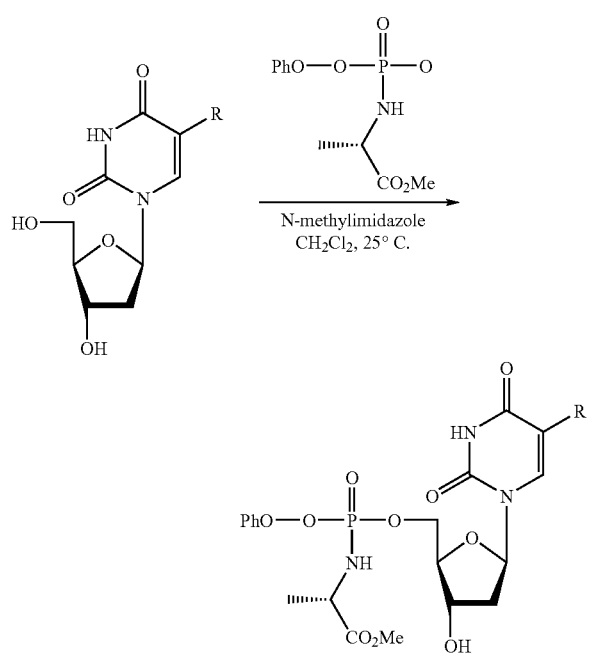

The following examples are intended to illustrate, but not limit the invention.

Examples 1 and 2

Synthesis of ECTA Compounds with Propargyl Tethers

Using the general synthetic procedure described supra, bis-aziridin-1-yl-phosphinic acid 3-[2-deoxyuridin-5-yl]-prop-2-ynyl ester was synthesized and analyzed by $^1$H NMR to yield the following result: $^1$H NMR (($CD_3$)$_2$SO) complicated due to noise. Salient features: δ 8.28 (d, 1, H6), 6.10 (pseudo-t, 1, H1'), 5.26 (m, changes with $D_2O$, 1, 3'-OH), 5.13 (m, exchanges with $D_2O$, 1, 5'-OH), 4.81 (q or dd, 2, propargyl-$CH_2$), 4.24 (m, 1, H3'), 3.57 (m, 2, 5'-$CH_2$), 2.15-2.0 (m, 8, aziridine-$CH_2$).

Bis-aziridin-1-yl-phosphinothioic acid 3-[2-deoxyuridin-5-yl]-prop-2-ynyl ester was also synthesized and analyzed by $^1$H NMR to yield the following result: $^1$H NMR (($CD_3$)$_2$SO) complicated due to noise. Salient features: δ 8.29 (d, 1, H6), 6.10 (pseudo-t, 1, H1'), 5.22 (m, exchanges with $D_2O$, 1, 3'-OH), 5.10 (m, exchanges with $D_2O$, 1, 5'-OH), 4.88 (q or dd, 2, propargyl-$CH_2$), 4.31 (m, 1, H3'), 3.52 (m, 2, 5'-$CH_2$), 2.15-2.0 (m, 8, aziridine-$CH_2$).

Examples 3 to 8

Synthesis of Furano-Pyrimidinones

Using the general synthetic procedure described supra, the following compounds were prepared.

Example 3

3-(2-Deoxy-β-D-ribofuranosyl)-6-(tetrahydropyran-2-yloxymethyl)furo[2,3-d]pyrimidin-2(3H)-one. $^1$H NMR (($CD_3$)$_2$SO) δ 8.80 (s, 1, H4), 6.74 (s, 1, H5), 6.16 (pseudo-t, 1, H1'), 5.27 (d, exchanges with $D_2O$, 1, 3'-OH), 5.12 (t, exchanges with $D_2O$, 1, 5'-OH), 4.72 (m, 1, THP-H2), 4.56 (q, 2, $CH_2$OTHP), 3.92 (m, 1, H4'), 3.64 (m, 2, 5'-$CH_2$), 2.40 (m, 1, H2'a), 2.03 (m, 1, H2'b), 1.68 and 1.50 (m, 8, THP). Low-resolution mass spectrum (DCI-$NH_3$) on bis-TMS derivative, m/z 323 (B+TMS+H$^+$), 511 (MH$^+$), 583 (M+TMS$^+$).

Example 4

3-(2-Deoxy-β-D-ribofuranosyl)-6-(hydroxymethyl)furo[2,3-d]pyrimidin-2(3H)-one. $^1$H NMR (($CD_3$)$_2$SO) δ 12.0 (bs, 1, OH), 8.24 (s, 1, H4), 6.53 (s, 1, H5), 5.51 (pseudo-t, 1, H1'), 4.42 (m, 2, $CH_2$OH). Low-resolution mass spectrum (DCI-$NH_3$), M/Z 167 (B+2H$^+$), 184 (B+NH4$^+$).

Example 5

1-[6-(tetrahydropyran-2-yloxymethyl)furo[2,3-d]pyrimidin-2(3H)-on-3-yl]-2-deoxy-β-ribofuranos-5-yl phenyl methoxy-L-alaninylphosphoramidate. 1H NMR ((CD3)2SO) complicated due to presence of diastereomers. Salient features: δ 8.62 and 8.59 (each s, each 1, H4), 7.4-7.1 (m, 5, PhO), 6.61 and 6.60 (each s, each 1, H5), 6.25 (m, 1, H1'), 4.56 (q, 2, propargyl-CH2), 3.56 and 3.54 (each s, each 3, CO2Me), 2.0 (m, 1, H2'b), 1.22 (m, 3, alaninyl-α-Me). Low-resolution mass spectrum (DCI-NH3), m/z 167 (B+2H$^+$), 184 (B+H$^+$+NH4+-TBP).

Example 6

1-[6(Hydroxymethyl)furo[2,3-d]pyrimidin-2(3H)-on-3-yl]-2-deoxy-D-ribofuranos-5-yl phenyl methoxy-L-alaninylphosphoramidate. $^1$H NMR (CDCl$_3$) complicated due to presence of diastereomers. Salient features: δ 8.5 (s, 1, H4), 7.4-7.1 (m, 5, PhO), 6.36 and 6.30 (each s, each 1, H5), 6.23 (m, 1, H1'), 3.67 and 3.65 (each s, each 3, CO$_2$Me), 2.69 (m, 1, H2'a), 2.10 (m, 1, H2b), 1.35 (m, 3, alaninyl-α-Me). Low-resolution mass spectrum (DCI-$NH_3$), m/z 525 (MH$^+$), 595 (MNH$_4^+$).

Example 7

The 4-nitrophenyl ether derivative of 5-(3-hydroxy-1-propynyl)-2'-deoxyuridine was prepared according to standard ether synthesis as shown below.

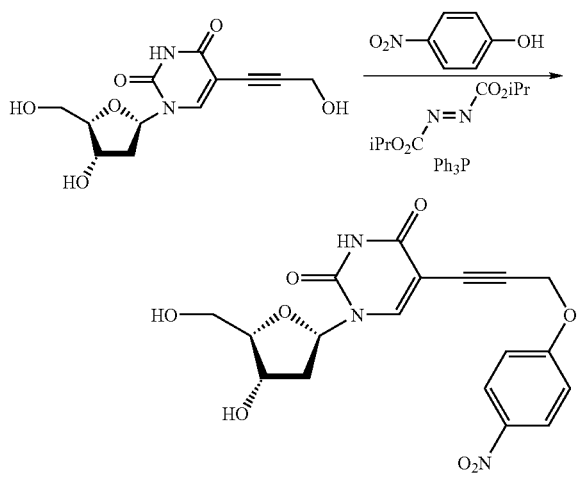

Example 8

5-[3-(4-Nitrophenoxy)-1-propynyl]-2'-deoxyuridine. A solution of pre-dried 5-(3-hydroxy-1-propynyl)-2'-deoxyuridine Robins, M. J. et al., (1983) (565 mg, 2 mmol) in 40 mL of anhydrous THF under argon was treated with 4-nitrophenol (696 g, 5 mmol), triphenylphosphine (787 mg, 3 mmol), and diisopropyl azodicarboxylate (590 L, 3 mmol), and the reaction mixture heated at 60° C. until the solution was clear, and then 1 h longer. The mixture was allowed to cool to 23° C. and then it was evaporated onto $SiO_2$ and purified by chromatography using $MeOH/CH_2Cl_2$ as eluent to afford 107 mg (13%) of the desired ether product: mp 112-118° C. $^1H$ NMR $((CD_3)_2SO)$ δ 11.65 (s, exchanges with $D_2O$, 1, NH), 8.29 (s, 1, H6), 8.24 (d, J=9.3 Hz, 2, m-ArH), 7.23 (d, J=9.3 Hz, 2, oArH), 6.09 (pseudo-t, 1, H1'), 5.17 (s, 2, propargyl-$CH_2$), 4.22 (m, 1, H3'), 3.80 (m, 1, H4), 3.59 (m, 2, 5'-$CH_2$), 2.13 (pseudo-t, 2, 2'-$CH_2$). Low-resolution mass spectrum (DCI-$NH_3$) on per-trimethylsilyated material, m/z 547 [M(TMS)$_2$H$^+$], 565 [M(TMS)$_2$NH$^+$], 620 [M(TMS)$_3$H$^+$]n.

Example 9

5-(4-Carbethoxy-1,3-butadienyl)-2'-deoxyuridine (a) 5Carbomethoxyvinyl)-2'-deoxyuridine-3',5'-bis(tetrahydro-2H-pyran-2-yl)ether (I)

A slurry of 5-(carbomethoxyvinyl)-2'-deoxyuridine (3.0 g, 9.6 mmol), 3,4-dihydro-2H-pyran (22 mL, 21.3 mmol) and pyridinium p-toluenesulfonate (PPTS, 0.242 g, 0.96 mmol) in dimethylformamide (DMF, 5 mL) was stirred at 50° C. for 18 h. The resulting solution was concentrated in vacuo (bath temperature 45° C.) to give a thick, pale yellow oil. The oil was dissolved in EtOAc and the solid was filtered. The solution was again concentrated. The oil obtained was purified by column chromatography on silica gel using 50-75% EtOAc/hexane as eluent to give 3.81 g (85%) of pure product as a colorless oil.

(b) 5-(3-Hydroxyprop-1-enyl)-2'-deoxyuridine-3',5'-bis(tetrahydro-2H-pyran-2-yl)ether (II)

A solution of (I) (3.5 g, 7.27 mmol) in $CH_2Cl_2$ (14 mL) was cooled to −78° C. in a dry ice/acetone bath. Diisobutylaluminum hydride (DIBAL-H) in toluene (1.0 M, 24 mL, 24.0 mmol) was added dropwise over 2 h while the temperature was maintained at −78° C. The solution was stirred at −78° C. for an additional 2 h and MeOH (2.5 mL) was added dropwise to destroy any excess DIBAL-H. The reaction mixture was cannulated into a mixture of 30% citric acid solution (50 mL), ice (25 g) and EtOAc (30 mL) over ca. 20 min. The phases were separated and the aqueous phase was extracted with EtOAc (2×25 mL). The combined organic phase was washed with saturated $NaHCO_3$ (20 mL) and brine (20 mL), dried over $MgSO_4$ and concentrated to give 3.288 g (100%) of colorless oil (c) 5-(3-Oxoprop-1-enyl)-2'deoxyuridine-3',5'-bis(tetrahydro-2H-pyran-2-yl)ether (III)

To a solution of crude (II) obtained from above (1.988 g, 4.4 mmol) in $CH_2Cl_2$ (9 mL) was added solid pyridinium dichromate (PDC; 1.82 g, 4.8 mmol) with water cooling. The suspension was stirred while acetic acid (0.4 mL) was added dropwise. The water bath was removed and the reaction was stirred at room temperature for 1 h. The crude product was filtered through a pad of florisil (2×2.5 cm) and the florisil washed with 35 mL EtOAc. The brown solution obtained was filtered through another column of florisil (3.5 cm diam×2.5 cm height). The filtrate was concentrated to give 1.273 g (64%) yield) of very light brown oil.

(d) 5-(4-Carbethoxy-1,3-butadienyl)-2'-deoxyuridine-3',5'-bis(tetrahydro-2H-pyran-2-yl)ether (IV)

(Carbethoxymethylene)triphenylphosphorane (0.32 mg, 0.92 mmol) was added to a solution of the crude aldehyde (III) (0.344 g, 0.77 mmol). The solution darkened and turned rust color. After 1 h, (III) was completely consumed as judged by thin layer chromatography. The solvent was evaporated and the crude product was purified by column chromatography on silica gel using 35-45% EtOAc/hexane as eluent. The pure product (0.310 g, 78% yield) was obtained as colorless oil.

(e) 5-(4-Carbethoxy-1,3-butadienyl)-2'-deoxyuridine (V)

5-(4-Carbethoxy-1,3-butadienyl)-2'-deoxyuridine-3',5'-bis(tetrahydro-2H-pyran-2-yl)ether (IV) (0.637 g, 1.22 mmol) was dissolved in MeOH (1.5 mL) and PPTS (0.049 g, 0.16 mmol) was added. The solution was stirred at 50° C. for 7.5 h and left at room temperature overnight. A white precipitate was formed. The reaction mixture was cooled to 0° C. and filtered to give pure (V) as a white solid (0.188 g). The filtrate was concentrated and chromatographed on silica gel using 50-100% EtOAc/hexane as eluent to give a further 0.180 g product. The total yield of the product was 0.368 g (86%).

$^1H$ NMR (DMSO-$d_6$): 1.22 (3H, t, J=7 Hz), 2.17 (2H, br t, J=5.5 Hz), 3.55-3.75 (2H, m), 3.81 (1H, m), 4.12 (2H, q, J=7 Hz), 4.25-4.28 (1H, m), 5.19 (1H, t, J=4.8 Hz), 5.27 (1H, d, J=4.1 Hz), 5.98 (1H, d, J=14.5 Hz), 6.14 (1H, t, J=6.75 (1H, d, J=14.5 Hz), 7.18-7.30 (2H, m), 8.30 (1H, s), 11.56 (1H, s).

Example 10

5-(4-Carbomethoxy-1,3-butadienyl)-2'-deoxyuridine (Va)

A solution of triethylamine (3.9 mL, 28.2 mmol) in dioxane (12 mL) was deareated by bubbling nitrogen through for 15 min. Palladium acetate (0.60 g, 0.26 mmol) and triphenylphosphine (0.183 g, 0.70 mmol) were added and the solution was heated at 70° C. for 20 min to give a dark brown solution. 5-Iodo-3'-deoxyuridine (5.0 g, 14.1 mmol) and methyl 2,4-pentadienoate (2.5 g, 22.3 mmol) was added and the mixture was heated under reflux for 15 h. The solvent and volatile components were evaporated in vacuo and the residue was partitioned between water (15 mL) and EtOAc (15 mL). The phases were separated and the aqueous phase was extracted twice with EtOAc (10 mL each). The combined organic phase was washed with brine and concentrated. The residue was dissolved in MeOH (15 mL) and allowed to cool to room temperature. The solid formed was collected by filtration, washed with a small quantity of MeOH and dried in vacuo to give 0.38 g brown powder.

$^1$H NMR (DMSO-$d_6$): 2.17 (2H, t, J=6.4 Hz), 3.55-3.70 (2H, m), 3.66 (3H, s), 3.82 (1H, q, J=3.6 Hz), 4.27 (1H, m), 5.18 (1H, t, J=4.9 Hz), 5.26 (1H, d, J=4.5 Hz), 5.99 (1H, d, J=14.4 Hz), 6.14 (1H, d, J=6.4 Hz), 6.74 (1H, d, J=14.8 Hz), 7.20-7.35 (2H, m), 8.30 (1H, s), 11.56 (1H, s).

The filtrate from above was concentrated and chromatographed on silica gel using 60-100% EtOAc/hexanes as eluent to give another 0.70 g of product as a brown foam. The combined yield was 1.08 g (22.6%).

Example 11

5-(4-Carboxy-1,3-butadienyl)-2'-deoxyuridine (VI)

5-(4-Carbethoxy-1,3-butadienyl)-2'-deoxyuridine (V, from Example 1) (0.449 g, 1.28 mmol) was dissolved in 2N NaOH (3 mL) and stirred at 25° C. After 20 mm, a precipitate was formed and TLC showed that the starting material was completely consumed. The mixture was cooled to 0° C. and acidified to pH 1 with 2N HCl. The resulting off-white solid was filtered off, washed with water and dried in vacuo to give 0.225 g (54%) product.

$^1$H NMR (DMSO-$d_6$): 2.12-2.19 (2H, m), 3.50-3.70 (2H, m), 3.75-3.85 (1H, m), 4.24-4.29 (1H, m), 5.19 (1H, t, J=4.8 Hz), 5.27 (1H, d, J=4.2 Hz), 5.80-5.95 (1H, m), 6.14 (1H, t, J=6.4 Hz), 6.60-6.75 (1H, m), 7.15-7.25 (2H, m), 8.26 (1H, s), 11.56 (1H, m), s), 12.16 (1H, br s).

The filtrate and washings were combined and evaporated to dryness. The resulting sticky yellow solid was dissolved in MeOH from which a white precipitate was formed. The solid was filtered off to give an additional 0.200 g of product.

Method II

The title compound can also be prepared from 5-(4-carbomethoxy-1,3-butadienyl)-2'-deoxyuridine (Va) (prepared according to the method in Example 2) in comparable yield as mentioned above.

Example 12

5-(4-Bromo-1E,3E-butadienyl)-2'-deoxyuridine (VIIa) and 5-(4-Bromo-1E,3Z-butadienyl)-2'-deoxyuridine (VIIb)

To a solution of 5-(4-carboxy-1,3-butadienyl)-2'-deoxyuridine (VI) (0.200 g, 0.62 mmol) in DMF (1 mL) was added KHCO$_3$ (0.185 g, 1.84 mmol) and the mixture was stirred for 20 mm at 25° C. A solution of N-bromosuccinimide (0.117 g, 0.65 mmol) in DMF (0.3 mL) was added dropwise. Smooth gas evolution (CO$_2$) occurred throughout the addition. The resulting brown suspension was stirred for 2 h at 25° C. at which time TLC showed that (VI) was completely consumed. Water (10 mL) was added to the suspension and the resulting solution was extracted with EtOAc (2×15 mL). The extract was dried over MgSO$_4$ and the solvent was evaporated in vacuc to give a yellow solid (178 mg, 80% yield) consisting of a mixture of two isomers as shown by $^1$H NMR. The crude product was separated by semi-preparative HPLC (reversed phase C18 column) using 20% acetonitrile in water as the mobile phase to give the following isomers:

5-(4-Bromo-1E,3Z-butadienyl)-2'-deoxyuridine: retention time 10.5 minutes; $^1$H NMR: (DMSO-$d_6$): 2.11-2.18 (2H, m), 3.50-3.70 (2H, m), 3.80 (1H, distorted q, J=3.5 Hz), 4.25 (1H, m), 5.08 (1H, br s), 5.25 (1H, br s), 6.15 (1H, t, J=6.5 Hz), 6.40 (1H, d, J=7 Hz), 6.53 (1H, d, J=15.6 Hz), 6.83 (1H, dd, J=7, 10 Hz), 7.39 (1H, dd, J=10, 15.6 Hz).

5-(4-Bromo-1E,3E-butadienyl)-2'-deoxyuridine: retention time 15.1 minutes; $^1$HNMR (DMSO-$d_6$): 2.12-2.16 (2H, m), 3.50-3.70 (2H, m), 3.80 (1H, q, J=3.2 Hz), 4.26 (1H, m), 5.13 (1H, br s), 5.25 (1H, br s), 6.14 (1H, t, J=6.5 Hz), 6.36 (1H, d, J=15.6 Hz), 6.67 (1H, d, J=13.1 Hz), 6.84 (1H, dd, J=11, 13.1 Hz), 7.04 (1H, dd, J=11, 15.6 Hz).

Example 13

Using the procedures mentioned in Example 11, Method II, the following compounds can be obtained in a similar fashion: 5-(4-chloro-1,3-butadienyl)-2'-deoxyuridine (using N-chlorosuccinimide in place of N-bromosuccinimide in Step B); 5-(4-iodo-1,3-butadienyl)-2'-deoxyuridine (using iodine in sodium iodide in place of N-bromosuccinimide).

Example 14

5(2-Bromovinyl)-2'-Deoxyuridine Phenyl Methoxy-L-alaninyl Phosphoramidate

Phenyl Methoxy-L-alaninyl Phosphorochloridate

L-alanine methyl ester hydrochloride (245.8 g; 1.76 mol) was placed in a 12 L three-neck round bottom flask (equipped with a mechanical stirrer and thermometer) followed by 4.0 L of dichloromethane. The mixture was stirred for 15 minutes at room temperature. Phenyl phosphorochloridate (370.0 g; 1.76 mol) was added to the mixture and stirring was continued for 15 min at room temperature. The flask was placed in the bath with dry ice and the stirring was continued for 20 minutes until a uniform suspension was formed.

Freshly distilled tri-n-butylamine (626.5 g; 3.38 mol) was added dropwise (~90 min) with vigorous stirring to the reaction mixture so that the temperature inside the flask was held at ~0° C. The bath was removed and the stirring was continued for 6 hours at room temperature. The solution was concentrated to ~2.84 L by evaporating several portions of the mixture on a rotary evaporator and the mixture was sealed under argon and stored at ~20° C. The product was 85% pure by phosphorus NMR to give an estimated concentration of phenylmethoxyalaninyl phosphochloridate of ~0.5 M.

Example 15

5-(2-Bromovinyl)-2'-Deoxyuridine Phenyl Methoxy-L-alaninyl Phosphoramidate (NB1011)

The reaction was performed under argon atmosphere. 5-(2-bromovinyl)-2'-deoxyuridine (BVdU) (204 g; 612 mmol) was placed in three-neck 3 L round bottom flask equipped with mechanical stirrer. The flask was placed in ice-water bath and 1600 mL (~800 mmol) of phenylmethoxyalaninyl phosphochloridate reagent were added using an addition funnel over 15 min with vigorous stirring of the reaction mixture, followed by the addition of 100 mL of N-methylimidazole over 5 minutes using syringe. After 5 minutes the mixture became clear and after 10 minutes the ice-water bath was removed to allow the mixture to warm up to room temperature while stirring was continued. The reaction was monitored by reversed phase HPLC and was complete in 3 hours. The reaction was quenched by the addition of 100 mL of methanol and the mixture was evaporated to an oil, re-dissolved in 6 L of dichloromethane and passed through 800 g of silica gel. The major portion of BVdU-PA referred to herein as NB1011, was passed through the column during the loading and finally the elution of NB1011 was completed by passing 5 L of 5% methanol in dichloromethane. All fractions containing NB1011 were combined and evaporated to an oil, the residue was dissolved in 4 L of ethyl acetate and the mixture was extracted with water (2×2 L). The organic layer was dried with sodium sulfate, filtered, and washed with ethyl acetate (3×300 mL). The combined filtrate and washings were evaporated to produce a lightly colored white foam; total weight ~540 g:

The crude product was purified by two silica gel chromatography using 0-5% MeOH in $CH_2Cl_2$ and 10% MeOH in $CH_2Cl_2$, respectively, as eluent. The yield of product (>98% pure) was 64 g.

Example 16

Using the methods described in Example 15, the phenyl methoxy-L-alaninyl phosphoramidates of the following nucleosides were prepared:
1. 5-(4,4-dibromo-1,3-butadienyl)-2'-deoxyuridine,
2. 5-(2-chlorovinyl)-2'-deoxyuridine,
3. 5-trifluoromethyl-2'-deoxyuridine,
4. 5-(4-carbethoxy-1,3-butadienyl)-2'-deoxyuridine,
5. 5-(4-carbomethoxy-1,3-butadienyl)-2'-dexoyuridine,
6. 5-(4-bromo-1E,3E-butadienyl)-2'-deoxyunridine,
7. 5-(4-bromo-1E,3Z-butadienyl)-2'-deoxyuridine,
8. 5-(trimethylsilylethynyl)-2'-deoxyuridine,
9. 5-(ethynyl)-2'-deoxyuridine,
10. 5-(1-decynyl)-2'-deoxyuridine,
11. 3-(2'-deoxy-β-D-ribofiuranosyl)-2,3-dihydrofuro[2,3-d]pyrimidin-2-one
12. 3-(2'-deoxy-β-D-ribofuranosyl)-6-octyl-2,3-dihydrofuro[2,3d]pyrimidin-2-one.

Derivatives

Salts, esters, and ethers of the above compounds disclosed herein are also within the scope of this invention. Salts of the prodrugs of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the prodrugs or compounds identified by the method of this invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously-contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl prodrug derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

In a further embodiment, the substrate may not be chemically related to pyrimidines or folates, but rather synthesized based upon known parameters of rational drug design See Dunn, W. J. et al. (1996).

Chemical assays for products, for example, where a reaction product is an anti-metabolite of the bromovinyl-derivatives of dUMP, are described in the Examples provided below or by Barr, P. J. et al. (1983).

Assays for Amount of Nucleoside and Monophosphate in Cells

This assay was performed with the compound NB 1011. However, it understood to those of skill in the art that the below method is easily modified for application or use with the prodrugs of this invention.

The cell lines MCF7 (breast cancer cell line); MCF7TDX (Tomudex resistant breast cancer cell line) and H630R10 (5-FU resistant colon cancer cell line obtained from Dr. S.

Copur, Yale University, see Copur, S. et al. (1995)) in RPMI medium supplemented with 10% FCS and antibiotics were plated in 100 mm Petri dishes at the amount of 750,000 cells per dish and were incubated overnight at 37° C. 100 μM of BVdU was added to each dish and the cells continued to grow for 2 days at 37° C. After that, the medium was aspirated and the cells were washed twice with phosphate buffered saline (PBS). Then 1 ml of PBS per dish was added and the dishes were placed in a −80° C. freezer. The cells were disrupted via freezing/thawing procedure, repeated twice. The cell debris in the resulting suspension were spun down (13,000 rpm, 10 minutes) and the supernatant was deproteinized by passing though a Centrifugal Filter Device (Centrifree, 30,000 cut-off, Amicon) by centrifugation at 5,000 rpm for 30 minutes on Sorvall Super T21 centrifuge (Rotor SL-50-T, 1,912 g) at 20° C. The pass-through was concentrated to the volume of 100 μl, and injected onto an HPLC column (Adsorbosphere HS, C18, 5 μn, 4.6 mm×150 mm, Alltech). The samples were analyzed using acetonitrile gradient in water containing trifluoroacetic acid. The peaks were detected at 300 mm, the maximum of absorption of BVdU-derivatives, and the amounts of compounds were expressed as peak area at 300 nm. The identification of compounds was done by comparison of their retention times and spectra with those of authentic standards.

AlamarBlue Cell Proliferation Assay

This assay was performed with the compound NB1011 and the prodrugs of this invention. Cells growing exponentially were transferred to 384-well flat bottom tissue culture plates. All cell types were plated at a density of 500 cells per well in 25 μL of complete medium (RPMI 1640+10% fetal bovine serum+antibiotics/antimycotics). After 24 hours (day 0), 25 μL of complete medium containing the compounds over the dose range of $10^{-3}$ to $10^{-10}$ M were added in triplicate. Drug exposure time was 120 hours (day 5), after which growth inhibition was assayed. 5 μL of the redox indicator, alamarBlue, was added to each well (10% v/v). After 4 hours incubation at 37° C., fluorescence was monitored at 535 nm excitation and 595 nm emission.

Crystal Violet Cell Proliferation Inhibition Assay

This assay was performed with the compound NB1011 and the prodrugs of this invention. The ability of the test compounds to block proliferation of cells was determined by the crystal violet procedure. (Sugarman, B. J. et al. (1985); and Antelman, D. et al. (1995)).

Compounds were dissolved in dimethyl sulfoxide to a concentration of 1M. They were further diluted as necessary into DMEM cell culture medium, and subsequently into the first wells of the 96-well microtiter plate. Each concentration was tested in triplicate on the target cell line. Compound concentrations from 1 μM to 3000 μM were tested. Cells were incubated with compound for 72 hours, the plates were washed, and the cells fixed with methanol and stained with crystal violet as described in Sugarman, B. J. et al. (1985); and Antelman, D. et al. (1995).

Western Blot Analysis of TK and TS Levels in Cell Lines

Western blot experiments were performed using human normal colon epithelium cell type CCD18co (obtained from ATCC, Manassas, Va.), colon adenocarcinoma cell line H630R10 resistant to 5-FU (obtained from Dr. S. Copur, Yale University, see Copur, S. et al. (1995), and a HER2-transfected breast cancer cell lines (Pegram, M. D. et al. (1997)). Cells were lysed in RIPA buffer (50 mM Tris-HCl, pH 7.5, 150 mM NaCl, 0.5% Triton X-100, 0.1% SDS and 0.5% deoxycholic acid, sodium salt and protease inhibitors). Protein concentrations were determined by using BCA-200 protein assay kit (obtained from Pierce, Rockford, Ill.). 10 μg of proteins from each cell line were resolved by 12% SDS-PAGE. The separated proteins were transferred onto PVDF membrane (obtained from Amersham, England), followed by immunoblot with human thymidylate synthase monoclonal primary antibody and anti-tubulin monoclonal antibody (manufactured by NeoMarkers, Fremont, Calif.). Horseradish peroxidase linked sheep anti-mouse Ig was used as secondary antibody (Amersham). The ECL plus kit (Amersham) was used for detection of immunoreactivity. The bands corresponding to thymidylate synthase were quantified and normalized to that of tubulin by image analysis (Molecular Dynamics Storm).

RT-PCR Analysis of TS mRNA in Cell Lines

Expression level of human thymidylate synthase transcripts in different cell lines were quantified by using RT-PCR Oligonucleotide primers for amplification of the human thymidylate synthase and B-actin were designed as follows: Thymidylate synthase sense primer (SEQ ID NO:1) 5'-GGGCAGATCCAACACATCC-3'(corresponding to bases 208-226 of thymidylate synthase cDNA sequence, Genbank Accession No. X02308), antisense primer (SEQ ID NO:2) 5'-GGTCAACTCCCTGTCCTGAA-3' (corresponding to bases 564-583), β-actin sense primer (SEQ ID NO:3) 5'-GCCAACACAGTGCTGTCTG-3' (corresponding to bases 2643-2661 of β-actin gene sequence, Genbank Accession No. M10277) and antisense primer (SEQ ID NO:4) 5'-CTCCTGCTTGCTGATCCAC-3' (corresponding to bases 2937-2955).

Total RNAs were isolated from cells using Rneasy mini kit (obtained from Qiagen, Valencia, Calif.). To monitor for possible DNA contamination, the primers for amplification of β-actin were designed to span the exon4/intron5/exon5 junction. Genomic DNA template leads to a 313 bp β-actin fragment, and cDNA template generates a 210 bp product.

Reverse transcription reactions were performed, using SuperScript preamplification system (Gibco/BRL, Gaithersburg, Md.). 3 μg total RNA was applied in a volume of 20 μl buffer to conduct reverse transcription reaction, followed manufacturer's protocol.

PCR reactions were performed in a volume of 48 μl, containing 3 μl of cDNA mixture from reverse transcription reaction, 3 mM $MgCl_2$, 50 mM KCL 20 mM Tris-Cl, pH 8.4, 0.2 mM of each dNTP, 0.4 TM of thymidylate synthase sense and antisense primers and 3 units of Taq DNA polymerase (obtained from Promega, Madison, Wis.). The reaction mixtures were incubated at 94° C. for 3 min, followed by 10 cycles of 1 min incubation at 94° C., 1 min incubation at 58° C., and then 1 min incubation at 72° C. After 10 cycles, human β-actin primers in 2 μl were added to achieve a final concentration of 0.2 μM, bringing the final reaction volume to 50 μl. PCR reaction was continued to a total of 28 cycles, followed by a 7 min incubation at 72° C.

5 μL of PCR products were resolved by electrophoresis in 2% agarose gel, followed by sting with SYBR Gold nucleic acid gel stain (obtained from Molecular Probes, Eugene, Oreg.). The DNA bands corresponding to thymidylate synthase were quantified and normalized to that of β-actin by Molecular Dynamics Storm.

Northern Blot Analysis

Northern blots were obtained from Invitrogen (Carlsbad, Calif.) and hybridized to a cloned TS cDNA probe. Hybridization signals were normalized vs. ribosomal protein S9 as a housekeeping transcript. A tumor was considered to overexpress TS mRNA if the normalized signal was enhanced at least 2-fold as compared to the normal tissue control.

Cloning, Expression and Purification of Human Thymidylate Synthase

For expression in E. coli the complete human TS ORF was subcloned into the T7 promoter expression vector pET28a (Novagen, Inc.). The resulting plasmid vector encodes the synthesis of human TS as a recombinant fusion protein with a six histidine followed by a thrombin cleavage site. This fusion protein adds a total of 20 extra amino acids to the amino terminus of human TS. To produce recombinant protein, the human TS expression vector was introduced into the E. coli strain BL21(DE3), a strain with the T7 RNA polymerase gene inserted into the chromosome under the control of the lac operator.

The human TS-poly-His fusion protein was purified using a metal chelating affinity resin (Novagen, Inc.). Protein purification was followed by electrophoresis on 10% SDS polyacrylamide gels. Protein concentrations were determined using the Pierce BCA protein assay. Approximately 10 mg of human TS fusion protein was recovered from a 500 ml culture of E. coli. When visualized with silver stain only the band corresponding to human TS was apparent. The identity of the human TS band was confirmed by performing a Western blot with the anti-TS monoclonal antibody TS 106 (NeoMarkers).

Thymidylate Synthase (TS) Enzyme Activity Assay

TS activity was measured using the spectrophotometric assay of Wahba, et al. (1961). In this assay, TS activity is monitored by measuring the increase in absorbency at 340 nm that occurs when the co-factor 5,10 methylene tetrahydrofolte is oxidized to dihydrofolate as dUTP is converted to dTTP. Enzyme prepared by this method has a specific activity of 0.5-0.65 units/mg protein. One unit is defined as the production of one micromole of dTMP per minute. This value is similar to that reported by Pedersen-Lane, J. et al. (1997).

Determination of Intracellular Products of TS Prodrug Metabolism

It is important to determine the intracellular products of TS prodrug metabolism in order to substantiate proposed mechanism of activation and action and to define agents that are candidate therapeutics. One acceptable view of intracellular metabolism of aryl phosphodiester amidates involves enzymatic conversion into a carboxylic acid, intramolecular rearrangement of the phosphomonoester amidate into to a 5'-monophosphoryl nucleoside. See, Valette et al. (1996). However, this mechanism is unlikely to describe intracellular processing of all phosphoramidate-based pronucleotides. For example, a different mechanism was proposed for aryl phosphomonoester amidate processing, one involving the simple direct conversion of the phosphoramidate to the monophosphate species by a phosphoramidate hydrolates. See, McIntee et al. (1997) and Fries et al. (1995). Regardless of the mechanism for unmasking the nucleoside monophosphate, this assay will detect products of TS conversion of the intracellular monophosphate to cytotoxic compounds within the cell.

Cells are incubated with an amount of prodrug compounds that induces 50% growth inhibition of high TS expressing cell lines (in the 72H assay, supra). Both low and high TS expresser cells are used (e.g., CCD18co vs. H630R10). Time course studies are performed in which treated cells are processed according to the method described by McIntee, E. J. et al. (1997). Cells are lysed with 60% methanol in water at −20° C., and particulate residue removed by centrifugation. The supernatants are dried and stored at −20° C. The aliquots are evaluated initially by RP-HPLC and then by LC-MS to document the intracellular conversation of the phosphoramidate to the monophosphate and also the ensuring transformation of the monophosphate by thymidylate synthase.

Documentation of Substrate Activity Utilizing Purified Thymidylate Synthase

This assay determines the specific activities of future TS enzyme preparations, to assure the activity of such preparations over time, and to determine whether compounds screened for suitable activity do inactivate the TS enzyme under in vitro reaction conditions.

To determine what reaction products are produced when prodrug compounds are incubated together with purified recombinant TS enzyme, reaction conditions similar to those employed with the TS activity assay are used to generate reaction products in vitro. These reaction products will are then analyzed by GC-mass spectrometry to identify the actual molecules formed.

Results

TS is Highly Expressed in Several Tumor Cell Lines and Primary Tumors

Figure 3A:
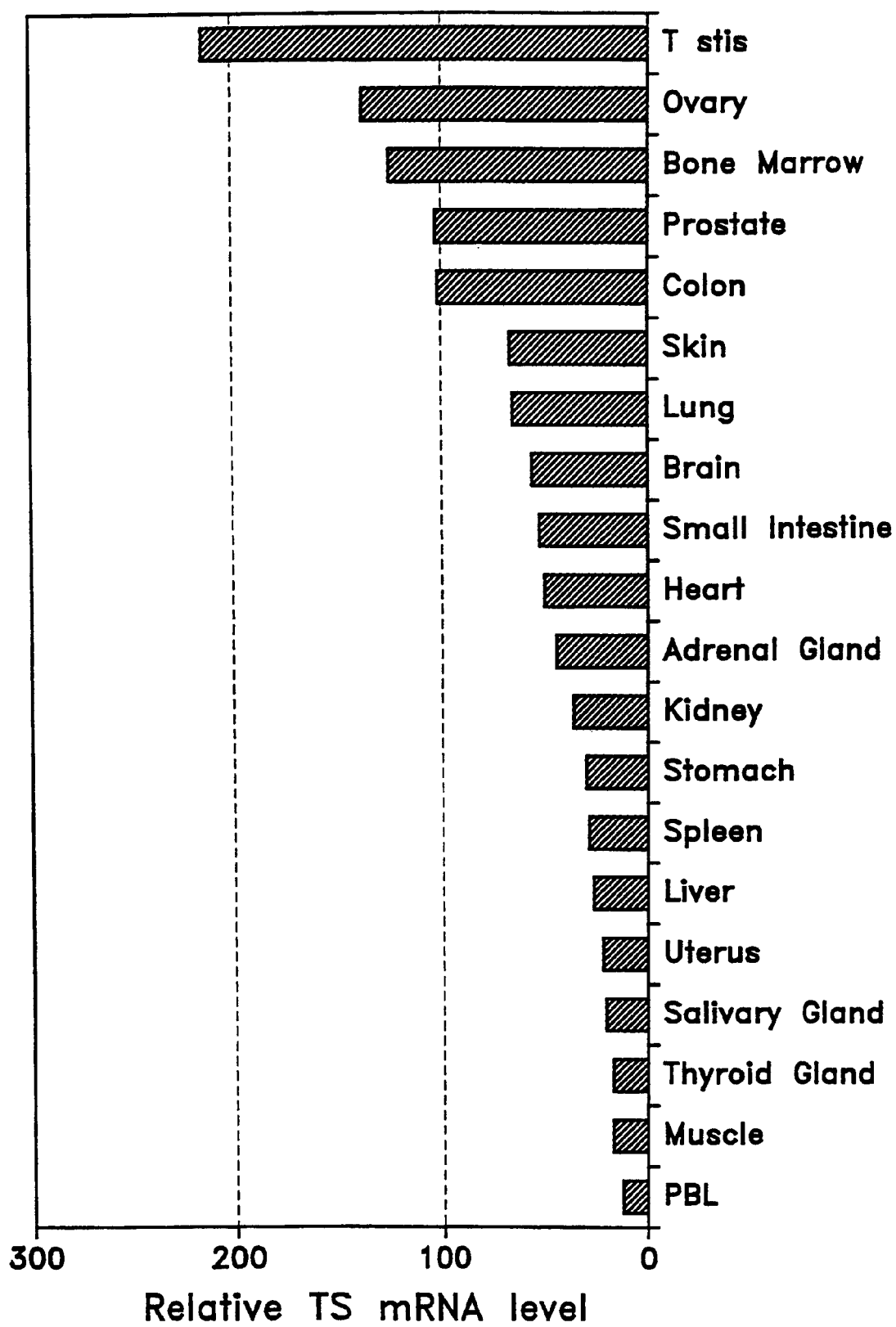
FIG. 3A shows relative TS levels in various human tissues.
Figure 3B:
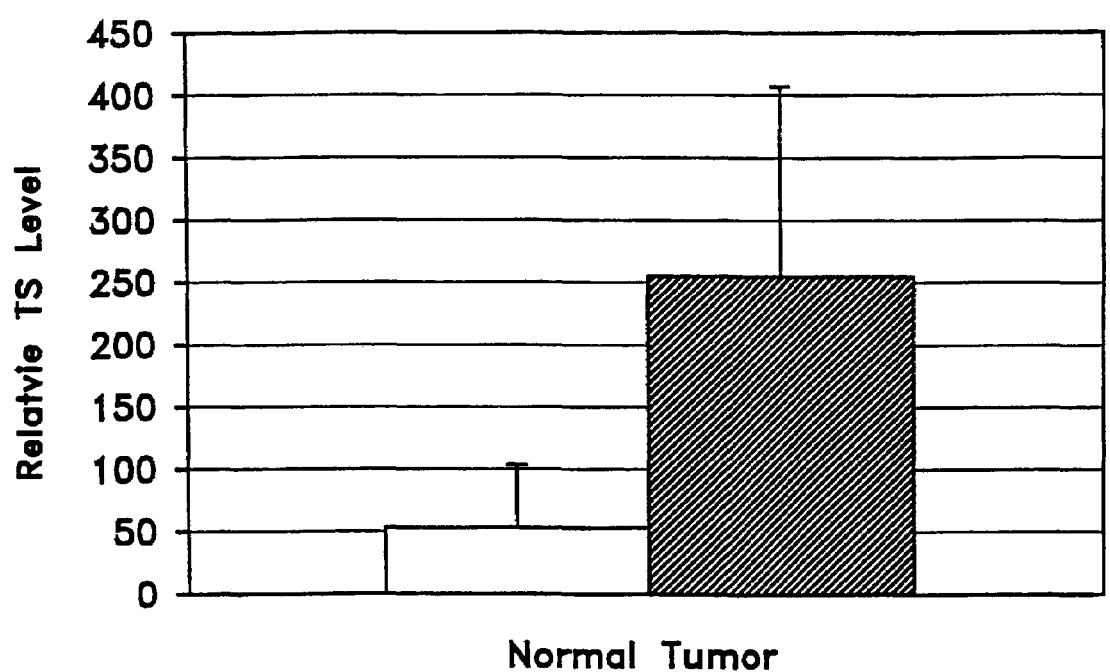
FIG. 3B shows a comparison of average TS mRNA levels between normal and human colon tumor tissues.

Thymidylate synthase expression levels in normal human brain, heart, kidney, spleen, liver, colon, lung, small intestine, stomach muscle, testis, ovary, uterus, prostate, thyroid gland, salivary gland, adrenal gland, skin, peripheral blood lymphocytes, bone marrow and from human colon and matched human normal tissues were determined using qualitative RT-PCR, as described above. Primers for β-actin were designed to span the exon4/intron5/exon5 junction to monitor for possible DNA contamination. Therefore, results reported in FIG. 3 are shown as relative TS mRNA levels. FIG. 3A shows relative TS mRNA in the multiple normal human tissues. FIG. 3B is a comparison of average TS mRNA between normal and tumor human colon tissues.

Thymidylate synthase (TS) protein levels in various cultured normal and tumor cell lines were determined following procedures described above. Protein levels were measured by Western blot analysis; the results are shown below.

TABLE 3

TS protein level in human normal and tumor cell types

| Cell strains | Description | TS level[1] |
|---|---|---|
| NHOST | Bone, osteoblast | 51 |
| NPRSC | Prostate, stroma | 98 |
| CCD18co | Colon epithelium, fibroblast | 100 |
| WI38 | Lung, embryonic | 150 |
| DET551 | Skin, fibroblast-like, embryonic | 177 |
| MRC9 | Lung, fibroblast-like, embryonic | 211 |
| NHDF | Skin, fibroblast | 224 |
| NHLF | Lung, fibroblast | 236 |
| Average | | 156 ± 24[2] |

[1]Thymidylate Synthase (TS) - TS levels were determined by using Western blot analysis, the quantified expression levels were expressed as values relative to that of cell strain CCD 18co.
[2]Standard error Tumor Cells (≧4X TS)

| | | |
|---|---|---|
| H630/TDX | Colon, carcinoma, TDX[2] resistant | 671 |
| HCTC(+) | Colon, carcinoma, increased TS | 1276 |

TABLE 3-continued

| | | |
|---|---|---|
| MCF7/TDX | Breast, adenocarcinoma, TDX[2] resistant | 1980 |
| H630R10 | Colon, carcinoma, 5-FU[3] resistant | 2305 |
| Average | | 1558 ± 354[4] |

[1]Thymidylate Synthase (TS) - TS levels were determined by using Western blot analysis, the quantified expression levels were expressed as values relative to that of cell strain CCD 18co.
[2]Tomudex
[3]5-Fluorouracil
[4]Standard Error The Amounts of BVdUMP and BVdU Measured in Cells The amounts of BVdUMP or BVdU present in lysates cell lines MCF7, MCF7TDX, and H630R10 each treated with BVdU, are expressed as an area of a corresponding HPLC peak at 300 nm. Note that extinction coefficients of these compounds at 300 nm are the same, therefore the comparison of the peak areas allows direct comparison of the amounts formed.

Table 4, below, shows the level of BVdUMP and BVdU measured inside the cells after 2 days treatment. Cells were incubated in complete media with 100 μm BVdU. Lysates were prepared and BVdUMP and BVdU levels were determined.

MCF7TDX cell lyzate as compared to H630R10 cell lysate. Tumor lysates prepared as described (Look, K. Y. et al. (1997)) can be prepared and used in this assay with BVdU (or other candidate nucleoside) to determine whether a given patient is a candidate for nucleoside versus phosphoramidate therapy.

These results show that in MCF7TDX cells BVdU can be phosphorylated to yield the corresponding monophosphate, a substrate for subsequent TS reaction whereas in H630R10 cells such phosphorylation goes on significantly slower than in MCF7TDX. It is important to mention that MCF7TDX is a breast tumor cell line. It has been reported that in breast tumor cells a TK with properties different from human TK from other tissue is found. (Madec, A. et al. (1988)). This TK might be responsible for BVdU phosphorylation. Based on the results presented above it is expected that nucleosides, such as BVdU, might be especially useful for treatment of certain types of cancer, including breast cancer, where BVdU can be phosphorylated. Moreover, the experimental procedure described above, allows in vitro determination of feasibility of using BVdU or other nucleosides for a given cancer type using the following approach. If a tissue sample is available the cells may be treated in vitro with BVdU and possible formation of BVdUMP can be monitored. Should BVdUMP formation be registered the tumor type must be considered as a candidate for successful nucleoside treatment as opposed to phosphoramidate derivatives.

TABLE 5

Alamar Blue Cytotoxicity Assay f Normal and Tumor Cells

| | IC50 (μM) | | | Mean | IC50 (μM) | | Mean |
|---|---|---|---|---|---|---|---|
| | MCF7TDX | H630R10 | HT1080 | Tumor | CCd18co | Det551 | Normal |
| NB1011 | 2 | 82 | 182 | 88.7 | 414 | 398 | 406 |
| BVDU | 0.02 | 201 | 719 | 306.7 | 1000 | ND | 1000 |
| NB1012 | 127 | 82 | — | 104.5 | ND | 110 | 110 |
| NB1013 | 26 | 92 | ND | 59.0 | ND | 570 | 570 |
| NB1020 | 0.48 | 326 | 1000 | 442.2 | 1000 | ND | 1000 |
| NB1014 | 396 | 287 | ND | 341.5 | ND | 239 | 239 |
| NB1016 | 877 | 337 | ND | 607.0 | ND | 338 | 338 |
| NB1021 | 637 | 141 | 1000 | 592.7 | 1000 | ND | 1000 |
| NB1017 | 55 | 52 | ND | 53.5 | ND | 137 | 137 |
| NB1024 | 4 | 14 | 258 | 92.0 | 1000 | ND | 1000 |
| NB1018 | 115 | 164 | ND | 139.5 | ND | 412 | 412 |
| NB1022 | 8 | 0.03 | 3 | 3.7 | 9 | ND | 9 |
| NB1019 | 251 | 95 | ND | 173.0 | ND | ND | — |
| NB1023 | 5 | 0.11 | 2 | 2.4 | 11 | ND | 11 |
| NB1026 | 1000 | 1000 | 1000 | 1000.0 | 1000 | ND | 1000 |
| NB1025 | 49 | 192 | 454 | 231.7 | 378 | ND | 378 |

TABLE 4

| Cell Lines | BVdUMP | BVdU | BvdUMP/(BVdUMP + BVdU) × 100 |
|---|---|---|---|
| MCF7 | 63.7 | 90.8 | 44.2 |
| MCF7TDX | 10.9 | 39.0 | 21.2 |
| H630R10 | <1 | 26.3 | <4 |

The table shows that BVdU can penetrate all three cell types, but appears as BVdUMP most prominently in MCF7 and MCF7TDX cell lines. Little conversion occurs in the H630R10 cell line.

In a separate experiment, MCF7TDX and H630R10 cell lysates were used to catalyze BVdU phosphorylation in a cell free system with ATP added as a phosphate donor method. This confirmed the much higher rate of this reaction in

TABLE 6

Crystal Violet Assay of Normal and Tumor Cells

| | IC50 (uM) | | | IC50 (uM) | | Mean |
|---|---|---|---|---|---|---|
| | H630R10 | #12 | Tumor | CCD18co | Det551 | Normal |
| NB1011 | 130 | 1.2 | 65.6 | 408 | 356 | 382 |
| BVDU | 405 | 7 | 206.0 | 1000 | 625 | 812.5 |
| NB1017 | 111 | 17 | 64.0 | 206 | 253 | 229.5 |
| NB1024 | 92 | 3.3 | 47.7 | 784 | 460 | 622 |
| NB1018 | 248 | 20 | 134.0 | 254 | 431 | 342.5 |
| NB1022 | 3.8 | 0.3 | 2.1 | 0.7 | 3.6 | 2.15 |

TABLE 6-continued

Crystal Violet Assay of Normal and Tumor Cells

| | IC50 (uM) | | | | | |
|---|---|---|---|---|---|---|
| | H630R10 | HT1080 #12 | Mean Tumor | IC50 (uM) CCD18co | Det551 | Mean Normal |
| NB1019 | 220 | 24 | 122.0 | 162 | 824 | 493 |
| NB1023 | 2.7 | 0.2 | 1.5 | 0.9 | 3.3 | 2.1 |

Numbering in Tables 5 and 6 refer to the structures, shown infix Results from testing using the alamarBlue assay are shown in Table 5, and results from crystal violet based assays are shown in Table 6. MCF7-TDX was derived from MCF7 breast tumor cells via selection in cell culture in the presence of Tomudex, a direct inhibitor of TS. Such selection often results in high intracellular levels of TS (Freemantle, S. J. et al. (1995)). Similarly, H630R10 is a 5FU (fluoropyrimidine) resistant colon cancer epithelial cell line derived from H630 colon cancer cells. See, Copur, S. et al. (1995). HT1080, #12, is a fibrosarcoma tumor cell line that expresses high levels of TS via a transgene introduced into HT1080 tumor cells. Normal cell lines used in these assays include CCD18co (normal colon epithelium) and Det551 (normal skin).

The data in both Tables 5 and 6 indicate that most compounds are active as phosphoramidates and nucleosides. One exception is NB1026™, which has little detectable activity as a phosphoramidate, but is active as a nucleoside (NB1025™). This result indicates that NB1026™ may not be activated similar to NB1011™. Cytotoxicity results with the nucleosides, especially BVdU, NB1020™ (ClVdU) and NB1024™, are surprising since the literature teaches that 5-substituted compounds like BVdU are not efficiently monophosphorylated by human cells unless they express viral thymidine kinase. See, Balzarini, J. et al. (1985) and De Clerq, E. et al. (1997). These authors have proposed that once phosphorylated by the herpesvirus-encoded TK, the 5-substituted nucleotide derivative can bind to the TS enzyme and inactivate it. The results in Tables 4-6 demonstrate, for the first time, that at least some tumor cells may have an unusual thymidine kinase activity capable of phosphorylating 5-substituted uridine molecules similar to BVdU, and the other nucleosides shown herein. Alternatively, some tumor cells may have an unusually high amount, or form the normal TK enzyme (Suki, S. et al. (1995); and Romain, S. et al. (1995)), leading to a low, but sufficient activation of nucleosides to their corresponding monophosphates.

The compound NB1024™ as tested above consists of a mixture of two isomers, 5-(4-Bromo-1E,3E-butadienyl)-2'-deoxyuridine (VIIa), (Isomer 2), and 5-(4-Bromo-1E,3Z-butadienyl-2'-dexoyuridine (VIIb), (Isomer 1). These two compounds were separated by semi-preparative HPLC (reversed phase C18 column) using 20% acetonitrile in water as the mobile phase as described above (Example 12). The ability of each isolated compound to block cell proliferation was then determined by the crystal violet procedure. Results are shown in Table 7. The two isomers display markedly different activities with the Z isomer, showing significantly greater growth inhibiting activity in comparison with the E isomer.

TABLE 7

Cytotoxic Activity of NB1024 Isomers

| | TS HT1080 #12 | MCF7TDX | CCD18co | Det551 |
|---|---|---|---|---|
| NB1011 | 4.3 | 4.2 | 461 | 263 |
| BVdU | ND | <0.8 | >1000 | >1000 |
| NB1024 Mixture | 10.7 | 6.4 | >300 | >300 |
| NB1024 Isomer 1 | 10.1 | 9.8 | >300 | >300 |
| NB1024 Isomer 2 | >300 | >300 | >300 | >300 |

The first two cell lines, TS HT1080 #12 and MCF7TDX express high levels of TS, while the other two, CCD18co and Det551, are normal cells.

While the invention has been described in detail and with reference to specific embodiments thereof, it will be apparent to one skilled in the art that various changes and modifications can be made therein without departing from the spirit and scope thereof.

REFERENCES

Literature

Abraham et al. (1996) *J. Med. Chem.* 39: 4569-4575
Akdas, A. et al. (1996) *Eur. Urol.* 29(4):483-486
Almasan, A. et al. (1995a) *Proc. Natl. Acad. Sci. USA* 92:5436-5440
Almasan, A. et al. (1995b) *Cancer Metastases Rev.* 14:59-73
Antelman, D. et al. (1995) *Oncogene* 10:697
Asakura, J. et al. (1988) *Tetrahedron Lett.* 29:2855-2858
Asakura, J. et al. (1990) *J. Org. Chem.* 55:4928-4933
Aschele, C. et al. (1999) *J. Chem. Oncol.* 17(6):1760-1770
Baizarini, J. et al. (1985) *Methods Find. Exp. Clin. Pharmacol.* 7:19-28
Balzarini, J. et al. (1996) *Proc. Natl. Acad. Sci. USA* 93:7295-7299
Banerjee, D. et al. (1995) *Acta Biochem Pol.* 42:457
Banerjee, D. et al. (1998) *Cancer Res.* 58:4292-4296
Barbour, K. W. et al. (1992) *Molec. Pharmacol.* 42:242-248
Barbato, et al. (1989) Nucleosides Nucleotides 8(4):515-528
Barr and Robins (1981) *J. Med. Chem.* 24(12):1385-1388
Barr, P. J. et al. (1983) *Biochemistry* 22:1696-1703
Barrett, J. E. (1998) *J. Am. Chem. Soc.* 120:449-450
Benzaria et al. (1996) *J. Med. Chem.* 39:4958
Bergstrom, D. E. et al. ((1981) & (1984) *J. Med. Chem.* 27:279-284
Bertino, J. R. et al. (1996) *Stem Cells* 14:5
Bigge, et al (1980) *J. Amer. Chem. Soc.* 102:2033-2038
Callahan, A. P. et al. (1989) *Comm. Nucl. Med.* 20:3-6
Carreras and Santi (1995) *Annu. Rev. Biochem.* 64:721-762
Carter, P. et al. (1992) *Proc. Natl. Acad. Sci. USA* 89:4285-4289
Chadhuri, N. C. et al. (1995) *J. Am. Chem. Soc.* 117:10434-10442
Chen, L. et al. (1996) *Cancer Res.* 56:1331-1340
Cho, Y. M. et al. (1994) *Tetrahedron Lett.* 25:1149-1152
Clarke, R. (1996) *Breast Cancer Res. Treat.* 39:1-6
Cobleigh, M. A et al. (1999) *J. Clin. Oncol.* 17(9):2639-2648
Connors, T. A. and Knox, R. J. (1995) *Stem Cells* 13:501-511
Copur, S. et al. (1995) *Biochem. Pharm.* 49(10):1419-1426
Crisp, G. T. (1989) *Synth. Commun.* 19:2117-2123
Cruickshank, K. A. et al. (1988) *Tetrahedron Lett.* 29:5221-5224
Dale, et al. (1973) *Proc. Natl. Acad. Sci. USA* 70:2238-2242
DeClercq, E. et al. (1983) *J. Med. Chem.* 26:661-666

DeClercq, E. et al. (1997) *Clin. Micro. Revew* 10(4):674-693
Dicken, A. P. et al. (1993) *Proc. Natl. Acad. Sci. USA* 90:11797-11801
Dirven, H. A. et al. (1995) *Cancer Res.* 55:1701-1706
Dorr, R. T. and Von Hoff, D D., eds. (1994) "Cancer Chemotherapy Handbook" 2nd ed. (Appleton and Lange), pp. 768-773
Dyer, R. L. et al. (1991) *Nucl. Acids Chem.* 4:79-83
Edler, D. et al. (2000) *Clin. Cancer. Res.* 6(2):488-492
Fan, J. and Berino, J. (1987) *Oncogene* 14:1191-1200
Farquhar et al. (1994) *J. Med. Chem.* 37:3902-3909
Farquhar, J. et al. (1995) *J. Med. Chem.* 38:488-495
Freed, et al. (1989) *Biochem. Pharmacol.* 38:3193-3198
Freemantle, S. J. et al. (1995) *Br. J. Cancer* 71:925-930
Fries, K. M., et al. (1995) *J. Med Chem.* 38:2672-2680
Funk, J. O. (1999) *Anticancer Res.* 19(6A):4772-4780
Goodwin, J. T. et al. (1993) *Tetrahedron Lett.* 34:5549-5552
Gottesman, M. M. et al. (1995) *Annu. Rev. Genet.* 29:607
Graham, D. et al. (1998) *J. Chem. Soc. Perkin Trans.* 1:1131-1138
Haskell, C. M. ed., (1995) *Cancer Treatment* 4th Ed., W.B. Saunders Co., Philadelphia, Pa.
Hobbs, F. W. Jr. (1989) *J. Org. Chem.* 54:3420-3422
Holy, et al. (1999) *J. Med. Chem.* 42(12):2064-2086
Hostetler, et al. (1997) *Biochem. Pharmacol.* 53:1815
Houze, T. A. (1997) *Tumour Biol.* 18:53-68
Hsiao and Bardos (1981) *J. Med. Chem.* 24:887-889
Hudziak, R. M. et al. (1988) *Proc. Natl. Acad. Sci. USA* 85:5102
Husain, et al. (1994) *Cancer. Res.* 54:539
Jackman, A. L. et al. (1995a) *Ann. Oncol.* 6(9):871-881
Jackman, A. L. et al. (1995b) *Anticancer Drug Des.* 10:573
Johnson, P. G. et al. (1997) *J. Clin. Oncol.* 15:1923-1931
Jones, R. G. and Mann, M. J. (1953) *J. Am. Cancer Soc.* 75:4048-4052
Kashani-Sabet et al. (1988) *Cancer Res.* 48:5775-5778
Kobayashi, H. et al. (1995) *Japan. J. Cancer Res.* 86:1014-1018
Krajewskas and Snugar (1982) *Biochem. Pharmacol.* 31(6):1097-1102
Lasic, D. D. (1996) *Nature* 380:561-562
Lee, V. et al. (1997) *Exp. Cell Res.* 234:270-276
Lenz, H. J. et al. (1998) *Clin. Cancer Res.* 4:1227-1234
Les, A. et al. (1988) *Bio. Structure and Dynamics* 15(4):703-715
Lewis, J. G. et al. (1996) *Proc. Natl. Acad Sci. USA* 93:3176-3181
Lin, W-Y. et al. (1997) *Eur. J. Nucl. Med.* 24:590-595
Livak, K. J. et al. (1992) *Nucleic Acids Res.* 20:4831-4837
Lönn, U. et al. (1996) *Cancer* 77(1):107-112
Look, K. Y. et al. (1997) *Anticancer Res.* 17:2353-2356
Lovejoy, et al. (1997) *J. Pathol.* 181:130-135
Madec, A. et al. (1988) *Bull Cancer* 75:187-194
Mader, R. M. et al. (1998) *Gen. Pharmacol.* 31(5):661-666
McGuigan, C. (1993) *J. Med. Chem.* 36:1048-1052
McGuigan, C. (1996) *J. Med. Chem.* 39:1748-1753
McGuigan, C. et al. (1994) *FEBS Lett.* 351:11-14
McIntee, E. J. (1997) *J. Med. Chem.* 40:3323-3331
Melton, R. G. and Sherwood, R. E. (1996) *J. Natl. Cancer Inst.* 88:153-165
Meier, et al. (1997) *Bioorg. Med. Chem. Lett.* 7:1577
Meier, et al. (1997) *Bioorg. Med. Chem. Lett.* 7:99
Meier, et al., (1997) *International Antiviral News.* 5:183
Miller, J. H., "A short course in bacterial genetics: A laboratory manual and handbook for *E. coli* and related bacteria" Cold Spring Harbor Press (1992)
Morgan, A. S. et al. (1998) *Cancer Res.* 58:2568-2575
Negishi, et al. (1996) *Nuc. Acids Symp. Ser.* 35:137-138
Paradiso, A. et al. (2000) *Br. J. Cancer* 82(3):560-567
Pederson-Lane, J. (1997) *Protein Expression and Purification* 10:256-262
Pegram, M. D. et al. (1997) *Oncogene* 15:537-547
Phelps, M. E. et al. (1980) *J. Med. Chem.* 23:1229-1232
Pluta, et al. (1999) *Boll. Chim. Farm.* 138(1):30-33
Robins, M. J. et al. (1981) *Tetrahedron Lett.* 22:421-424
Robins, M. J. et al. (1982) *Can. J. Chem.* 60:554-557
Robins, M. J. et al. (1983) *J. Org. Chem.* 48:1854-1862
Romain, S. et al. (1995) *Intl. J. Cancer* 61(1):7-12
Roth, J. A. et al. (1999) *Oncology* 13(10 Supp. 5):148-154
Ruth, J. L. et al. (1978) *J. Org. Chem.* 43:2870-2876
Saboulard, L. et al. (1999) *Mol. Pharm.* 56:693-704
Santi, D. V. (1980) *J. Med. Chem.* 23:103-111
Sastry, et al., (1992) *Mol. Pharmacol* 41:441-445
Schaechter, M. et al., eds. (1993) Mechanisms of Microbial Disease, $2^{nd}$ Ed., Williams and Wilkins
Shepard, H. M. et al. (1988) *J. Clin. Immunol.* 8:353-395
Simon, S. M. and Schindler, M. (1994) *Proc. Natl. Acad. Sci. USA* 91:3497
Smith, K. A. et al. (1995) *Philos. Trans. R. Soc. Lon. B. Biol. Sci.* 347:49-56
Spector, D. L. et al. (1998) Cells, A Laboratory Manual, Vols I to III, Cold Spring Harbor Press
Stühlinger, M. et al. (1994) *J. Steroid. Biochem.* 49:39
Sugarman, B. J. et al. (1985) *Science* 230:943-945
Suki, S. et al. (1995) *Leukemia Lymphoma* 18(1-2):87-92
Tannock, I. F. (1996) *J. Clin. Oncol.* 14(12):3156-3174
Teh, B. T. (1999) *Anticancer Res.* 19(6A):4715-4728
Tolstikov, V. V. et al. (1997) *Nucleosides Nucleotides* 16:215-225
Troutner, D. A. (1987) *Nucl. Med. Biol.* 14:171-176
Valette, et al. (1996) *J. Med. Chem.* 39:1981
Voet, et al. (1995) *Biochemistry* $2^{nd}$ Ed., John Wiley & Sons, Inc.
Wahba, A. J. et al. (1961) *J. Biol. Chem.* 236(3):C11
Wallis, et al. (1999) *Farmaco* 54(1-2):83-89
Wataya, Y. (1979) *J. Med. Chem.* 22:339-340
Wettergren, Y et al. (1994) *Mol. Genet.* 20:267-285
Whalen and Boyer (1998) *Semin. Liver Dis.* 18(4):345-358
Wilson, J. D., et al. (eds.) "Harrison's Principles of Internal Medicine" $12^{th}$ ed., McGraw-Hill, Inc., pp. 21-76 (1991)
Yen, Y et al. (1994) *Cancer Res.* 54:3686-3691
Zeid, et al. (1999) *Nucleosides Nucleotides* 18(1):95-111

What is claimed is:

1. A compound or a pharmaceutically acceptable salt of the compound, wherein the compound has the structure:

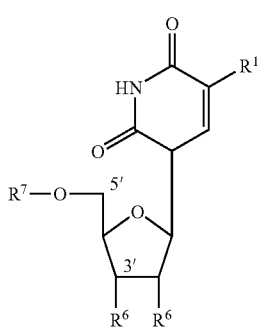

wherein:

(i) $R^1$ is a group:

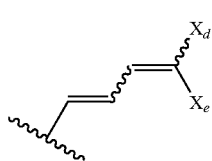

wherein $X_d$ is H; and, $X_e$ is Cl, I or Br;

or:

(ii) $R^1$ is a group:

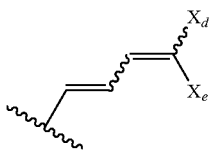

wherein $X_d$ and $X_e$ are independently the same or different and are selected from Cl, Br, and I;

and wherein each $R^6$ is independently the same or different from the other and is selected from the group consisting of —H, and —OH $R^7$ is —H, a monophosphate or the structure:

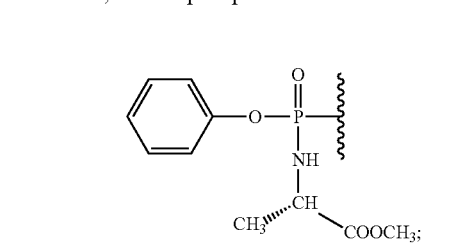

with the proviso that when $R^7$ is H, then $X_d$ is not H and $X_e$ is not Br; and wherein the compound has a D-ribofuranosyl moiety.

2. A compound according to claim 1, wherein:
R$^1$ is a group:

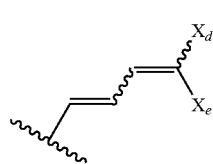

wherein X$_d$ is H; and, X$_e$ is Cl or Br.

3. A compound according to claim 1, wherein:
R$^1$ is a group:

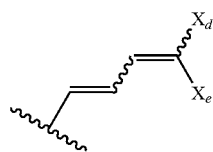

wherein X$_d$ and X$_e$ is Cl, I or Br.

4. A compound according to claim 3, wherein X$_d$ and X$_e$ is Cl or Br.

5. A compound according to claim 3, wherein X$_d$ and X$_e$ are each Br.

6. A compound according to claim 1, having the structure:

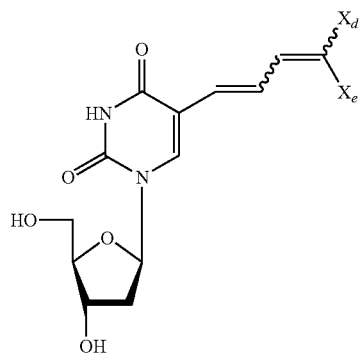

wherein X$_d$ is H; and, X$_e$ is Cl or I.

7. A compound according to claim 1, having the structure:

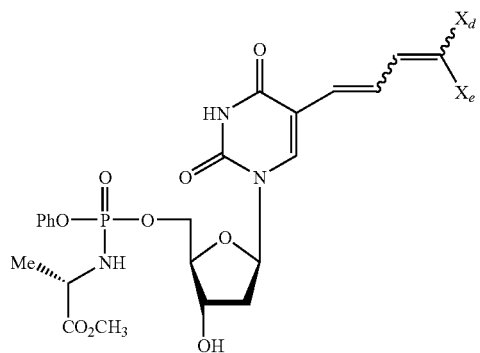

wherein X$_d$ is H; and, X$_e$ is Cl, I or Br.

8. A compound according to claim 1, having the structure:

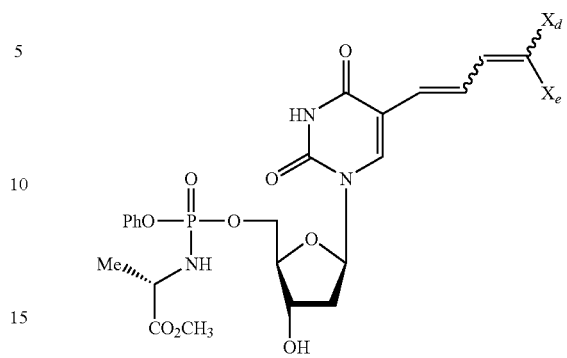

wherein X$_d$ and X$_e$ are independently the same or different and are selected from Cl, Br, and I.

9. A composition comprising a compound according to any one of claims 1, 2, 3-5, 6, 7 and 8 and a carrier.

10. A pharmaceutical composition comprising a compound according to any one of claims 1, 2, 3-5, 6, 7 and 8, and a pharmaceutically acceptable carrier.

11. A method for screening for a therapeutic agent, comprising:
(a) contacting a sample containing a target cell with a compound according to any one of claims 1, 2, 3-5, 6, 7 and 8;
(b) contacting a separate sample of the target cell with a potential therapeutic agent; and
(c) comparing the samples for inhibition of cellular proliferation or cell killing.

12. A method according to claim 11, wherein the target cell is characterized as resistant to a chemotherapeutic drug.

13. A method according to claim 11, wherein the target cell is characterized as expressing a target enzyme that is amplified as a result of selection in vivo by chemotherapy.

14. A method according to claim 11, wherein the target enzyme is an endogenous intracellular enzyme that is overexpressed in the target cell.

15. A method for inhibiting the growth of a cancer cell selected from the group consisting of a colon cancer cell, a breast cancer cell, and a fibrosarcoma cell and wherein said cell overexpresses thymidylate synthase, comprising contacting the cell with an effective amount of the compound of any of claims 1, 2, 3-5, 6, 7 and 8.

16. The method of claim 15, wherein the cancer cell is a breast cancer cell or a colon cancer cell.

17. A method for treating a cancer in a subject, wherein the cancer is selected from the group consisting of colon cancer, breast cancer and fibrosarcoma, comprising administering an effective amount of a compound of any of claims 1, 2, 3-5, 6, 7 and 8 to the subject.

18. The method of claim 17, wherein the cancer is breast cancer or colon cancer.

19. The method of claim 17, wherein the subject is a human patient.

20. The method of claim 18, wherein the subject is a human patient.

* * * * *

SEQUENCE LISTING

<160> NUMBER OF SEQ ID NOS: 4

<210> SEQ ID NO 1
<211> LENGTH: 19
<212> TYPE: DNA

```
                                  -continued
<213> ORGANISM: Homo sapiens

<400> SEQUENCE: 1
gggcagatcc aacacatcc                                                19

<210> SEQ ID NO 2
<211> LENGTH: 20
<212> TYPE: DNA
<213> ORGANISM: Homo sapiens

<400> SEQUENCE: 2
ggtcaactcc ctgtcctgaa                                               20

<210> SEQ ID NO 3
<211> LENGTH: 19
<212> TYPE: DNA
<213> ORGANISM: Homo sapiens

<400> SEQUENCE: 3
gccaacacag tgctgtctg                                                19

<210> SEQ ID NO 4
<211> LENGTH: 19
<212> TYPE: DNA
<213> ORGANISM: Homo sapiens

<400> SEQUENCE: 4
ctcctgcttg ctgatccac                                                19
```